US008388979B2

(12) United States Patent
Fushikida et al.

(10) Patent No.: US 8,388,979 B2
(45) Date of Patent: Mar. 5, 2013

(54) POLYPEPTIDE HAVING AFFINITY FOR ENVELOPE VIRUS CONSTITUENT AND USE THEREOF IN TRANSFERRING SUBSTANCE INTO CELL

(75) Inventors: Kuni Fushikida, Kusatsu (JP); Yoshitaka Kondo, Kusatsu (JP)

(73) Assignee: Ishihara Sangyo Kaisha, Ltd., Osaka (JP)

( * ) Notice: Subject to any disclaimer, the term of this patent is extended or adjusted under 35 U.S.C. 154(b) by 0 days.

(21) Appl. No.: 13/546,359

(22) Filed: Jul. 11, 2012

(65) Prior Publication Data

US 2012/0301961 A1 Nov. 29, 2012

Related U.S. Application Data

(62) Division of application No. 12/223,464, filed as application No. PCT/JP2007/051587 on Jan. 31, 2007.

(30) Foreign Application Priority Data

Jan. 31, 2006 (JP) .................................. 2006-21882
Aug. 28, 2006 (JP) ................................ 2006-230513

(51) Int. Cl.
*A61K 39/00* (2006.01)
*A61K 39/12* (2006.01)
*A61K 39/385* (2006.01)
*C12Q 1/70* (2006.01)
*G01N 33/53* (2006.01)
*G01N 33/567* (2006.01)
*C12P 1/00* (2006.01)

(52) U.S. Cl. ............. 424/196.11; 424/192.1; 424/193.1; 424/204.1; 435/5; 435/7.2; 435/7.8; 435/41

(58) Field of Classification Search ........................ None
See application file for complete search history.

(56) References Cited

U.S. PATENT DOCUMENTS

| | | | |
|---|---|---|---|
| 6,913,923 B2 | 7/2005 | Kaneda | |
| 2004/0028687 A1* | 2/2004 | Waelti | 424/178.1 |

FOREIGN PATENT DOCUMENTS

| | | |
|---|---|---|
| JP | 2001-286282 | 10/2001 |
| WO | 95/19374 | 7/1995 |
| WO | 98/44132 | 10/1998 |
| WO | 2004/010935 | 2/2004 |

OTHER PUBLICATIONS

F. Kato et al., "HVJ Envelope Vector Kit (GenomONE)", Medical Science Digest, vol. 29, No. 3, pp. 38-41, 2003 (in Japanese).
Ishihara Sangyo Kaisha, Ltd., "HVJ Envelope Vector Kit Protocol", pp. 1-20, May 25, 2005 (in Japanese).
H. Kotani et al., "The HVJ-Envelope as an Innovative Vector System for Cardiovascular Disease", Current Gene Therapy, vol. 4, No. 2, pp. 183-194, 2004.
Schödel et al. "Hepatitis B Virus Nucleocapsid/pre-S2 Fusion Proteins Expressed in Attenuated *Salmonella* for Oral Vaccination", The Journal of Immunology, vol. 145, 1990, pp. 4317-4321.
Sakaguchi et al., "Expression of the HN, F, NP and M proteins of Sendai virus by recombinant vaccinia viruses and their contribution to protective immunity against Sendai virus infections in mice", Journal of General Virology, vol. 74, 1993, pp. 479-484.
D. Mottershead et al., "Baculoviral Display of Functional scFv and Synthetic IgG-Binding Domains", Biochem. and Biophys. Res. Comm., Aug. 2000, vol. 275, No. 1, pp. 84-90.
I. Bergman et al., "Vesicular stomatitis virus expressing a chimeric Sindbis glycoprotein containing an Fc antibody binding domain targets to Her2/neu overexpressing breast cancer cells", Virology, Nov. 2003, vol. 316, No. 2, pp. 337-347.
R. Masood et al., "Retroviral vectors bearing IgG-binding motifs for antibody-mediated targeting of vascular endothelial growth factor receptors", International Journal of Molecular Medicine, Oct. 2001, vol. 8, No. 4, pp. 335-343.
T. Myers et al., "A Highly Conserved Region of the Sendai Virus Nucleocapsid Protein Contributes to the NP-NP Binding Domain", Virology, Mar. 1997, vol. 229, No. 2, pp. 322-335.
S. Horikami et al., "The Sendai Virus V Protein Interacts with the NP Protein to Regulate Viral Genome RNA Replication", Virology, 1996, vol. 222, No. 2, pp. 383-390.
Y. Kondo et al., "Efficient delivery of antibody into living cells using a novel HVJ envelope vector system", Journal of Immunological Methods, Jan. 2008, vol. 332, No. 1-2, pp. 10-17.
Neubert et al., "Sendai Virus NP ene Codes for a 524 Amino Acid NP Protein", Virus Genes, vol. 5, No. 1, 1991, pp. 25-32.

* cited by examiner

*Primary Examiner* — Louise Humphrey
(74) *Attorney, Agent, or Firm* — Wenderoth, Lind & Ponack, L.L.P.

(57) ABSTRACT

Delivery proteins are provided for transferring a protein, antibody or foreign substance into a cell without impairing the function or structure thereof. Further, methods of transferring a foreign substance into a cell at a high efficiency by using the delivery protein or an envelope virus or inactivated envelope virus in combination with said delivery protein are provided. The inventors discovered that a protein containing a polypeptide having an affinity for a constituent of the envelope virus contributes to the efficient enclosure of the foreign substance in the envelope. Moreover, the inventors discovered that use of the delivery protein enables foreign substances to be included in an envelope virus or inactivated envelope virus and therefore makes it possible to efficiently transfer the substances into cells without damaging the physiological function thereof.

16 Claims, 5 Drawing Sheets

(1)     (2)

Lane:1   2   3   4   5   6   7   8   9   10  11  12  13 14 15 16 17

(1) (2)

POLYPEPTIDE HAVING AFFINITY FOR ENVELOPE VIRUS CONSTITUENT AND USE THEREOF IN TRANSFERRING SUBSTANCE INTO CELL

This application is a divisional of Ser. No. 12/223,464, filed Jul. 31, 2008, which is a 371 U.S. national stage of International Application No. PCT/JP2007/051587 filed Jan. 31, 2007, herein incorporated by reference in their entirety.

FIELD OF THE INVENTION

The present invention relates to proteins which allow foreign substances to be enclosed within the envelope of envelope viruses or inactivated envelope viruses, and to methods for the introduction of foreign substances into target cells by means of envelope viruses or inactivated envelope viruses into which the foreign substance is incorporated with said protein.

BACKGROUND OF THE INVENTION

Based on introduction of genes into cells, it is difficult to control the levels of expressed proteins in each cell. Based on function inhibition represented by siRNA and the antisense method, it is also impossible to repress the function of already-expressed proteins. Especially, when a protein has a long half-life, it is hard to expect its inhibitory effects. Therefore, various attempts have been made to introduce proteins and antibodies into cells.

The known technique for introducing proteins into cells includes methods utilizing cationic liposomes and membrane-permeable peptides. Since the cationic liposome-based delivery performs transfection into cells using charges, it is frequently hard to make preparations because the charge varies from protein to protein, and it is often difficult to perform introduction due to protein charges. The known membrane-permeable peptide-based delivery techniques are those utilizing HIV-derived basic TAT peptides. The reported method of introducing antibodies into cells is a method utilizing a fusion protein consisting of TAT which functions as the membrane-permeable peptide and an antibody-binding region such as Protein A (Patent Document 1). However, the basic membrane-permeable peptide-based introduction of proteins still have problems in scenes wherein intracytoplasmic localization is demanded since basic peptides have nuclear import activity and TAT peptides are known to be transported into the nucleus.

The microinjection-based introduction of proteins and antibodies into cells needs special machinery and tools and also requires extremely complicated operations.

Although, on the basis of inactivated envelope virus delivery for introducing substances into cells, it is known that it is possible to introduce a nucleic acid such as a gene (Patent Document 2) and a protein such as RNase T1 and β-Galactosidase (Non-Patent Documents 1 & 2), it is not said to have enough efficiency to introduce antibodies into cells (Non-Patent Documents 3 & 4).

[Patent Document 1] JP 2005-052083, A
[Patent Document 2] US 2003/0013195 A
[Non-Patent Document 1] European Journal Biochemistry vol. 271, No. 17, 3567-3572, 2004
[Non-Patent Document 2] Neurosci. Lett., 378(1), 18-21, 2005 Apr. 11, 2005
[Non-Patent Document 3] Medical Science Digest vol. 29 (3), 38-41, 2003
[Non-Patent Document 4] Current Gene Therapy, vol. 4, 183-194, 2004

SUMMARY OF THE INVENTION

The present invention provides proteins for introducing one or more proteins, antibodies or other foreign substances (non-self or exogenous substances) into one or more cells without impairing the function, property or structure thereof; and methods of introducing the foreign substance into the cell in a time- and quantity-controllable manner with high efficiency by using the above-described delivery protein or an envelope virus or inactivated envelope virus in combination with said delivery protein.

The present inventors have conducted an extensive research on methods of enclosing foreign substances within the envelope of envelope viruses. As a result, the present inventors have succeeded in finding that a protein containing a polypeptide having an affinity for (or compatible to) a constituent of the envelope virus contributes to the efficient enclosure of the foreign substance in the envelope.

Further, the present inventors have succeeded in finding that use of the above-described proteins enables foreign substances to be included in an envelope virus or inactivated envelope virus and the resultant foreign substance-containing envelope viruses or inactivated envelope viruses make it possible to efficiently transfer the substance into cells without damaging the physiological function thereof. Therefore, the present invention has been achieved.

The present invention provides the following:

[1] A protein comprising (a) a polypeptide having an affinity for one or more envelope viral components in combination with (b) a polypeptide capable of binding to one or more foreign substances to be introduced into a cell.

[2] The protein according to the above [1], wherein the protein comprising said polypeptide (a) in combination with the polypeptide (b) is a fusion protein.

[3] The protein according to the above [1] or [2], wherein said polypeptide (a) is a polypeptide having an affinity for one or more components existing in the inner space of an envelope.

[4] The protein according to the above [1] or [2], wherein said polypeptide (a) is
 (1) a polypeptide of an amino acid sequence of SEQ ID NO: 2,
 (2) a polypeptide having an amino acid sequence substantially equivalent to the amino acid sequence of SEQ ID NO: 2, or
 (3) a peptide fragment (partial peptide) thereof.

[5] The protein according to the above [1] or [2], wherein said polypeptide (b) is an antibody-binding polypeptide.

[6] The protein according to the above [5], wherein said antibody-binding polypeptide is a polypeptide that can bind to an antibody Fc region or kappa (κ) light chain.

[7] The protein according to the above [5], wherein said antibody binding polypeptide is
 (1) a polypeptide of an amino acid sequence selected from the group consisting of SEQ ID NOs: 4, 49 and 51,
 (2) a polypeptide having an amino acid sequence substantially equivalent to the aforementioned amino acid sequence (1), or
 (3) a peptide fragment (partial peptide) thereof.

[8] A DNA encoding a fusion protein consisting of a polypeptide having an affinity for one or more envelope viral components and a polypeptide capable of binding to an antibody wherein said fusion protein is a polypeptide selected from the group consisting of:

(1) a fusion polypeptide consisting of a polypeptide of an amino acid sequence of SEQ ID NO: 2, a polypeptide substantially equivalent to the amino acid sequence of SEQ ID NO: 2, or a peptide fragment thereof, fused with a polypeptide of an amino acid sequence selected from the group consisting of SEQ ID NOs: 4, 49 and 51, a polypeptide having an amino acid sequence substantially equivalent to the aforementioned amino acid sequence of SEQ ID NO: 4, 49 or 51, or a peptide fragment thereof, (2) a polypeptide of an amino acid sequence selected from the group consisting of SEQ ID NOs: 6, 13, 55 and 59, and (3) a polypeptide having an amino acid sequence substantially equivalent to a polypeptide of an amino acid sequence selected from the group consisting of SEQ ID NOs: 6, 13, 55 and 59.

[9] An envelope virus or inactivated envelope virus containing a protein comprising (a) a polypeptide having an affinity for one or more envelope viral components in combination with (b) a polypeptide capable of binding to one or more foreign substances to be introduced into a cell.

[10] The envelope virus or inactivated envelope virus according to the above [9], wherein said virus contains a fusion protein consisting of a polypeptide having an affinity for one or more envelope viral components and an antibody-binding polypeptide wherein said fusion protein is a polypeptide selected from the group consisting of:

(1) a fusion polypeptide consisting of a polypeptide of an amino acid sequence of SEQ ID NO: 2, a polypeptide substantially equivalent to the amino acid sequence of SEQ ID NO: 2, or a peptide fragment thereof, fused with a polypeptide of an amino acid sequence selected from the group consisting of SEQ ID NOs: 4, 49 and 51, a polypeptide having an amino acid sequence substantially equivalent to the aforementioned amino acid sequence of SEQ ID NO: 4, 49 or 51, or a peptide fragment thereof, (2) a polypeptide of an amino acid sequence selected from the group consisting of SEQ ID NOs: 6, 13, 55 and 59, and (3) a polypeptide having an amino acid sequence substantially equivalent to a polypeptide of an amino acid sequence selected from the group consisting of SEQ ID NOs: 6, 13, 55 and 59.

[11] An envelope virus or inactivated envelope virus containing a complex constituted of (i) a protein comprising (a) a polypeptide having an affinity for one or more envelope viral components in combination with (b) a polypeptide capable of binding to one or more foreign substances to be introduced into a cell, and (ii) one or more foreign substances.

[12] The envelope virus or inactivated envelope virus according to the above [11], wherein said foreign substance is an antibody.

[13] The envelope virus or inactivated envelope virus according to the above [12], wherein said virus contains a complex constituted of (i) a fusion protein consisting of a polypeptide having an affinity for one or more envelope viral components, fused to an antibody binding polypeptide, and (ii) an antibody, wherein said fusion protein is a polypeptide selected from the group consisting of:

(1) a fusion polypeptide consisting of a polypeptide of an amino acid sequence of SEQ ID NO: 2, a polypeptide substantially equivalent to the amino acid sequence of SEQ ID NO: 2, or a peptide fragment thereof, fused with a polypeptide of an amino acid sequence selected from the group consisting of SEQ ID NOs: 4, 49 and 51, a polypeptide having an amino acid sequence substantially equivalent to the aforementioned amino acid sequence of SEQ ID NO: 4, 49 or 51, or a peptide fragment thereof, (2) a polypeptide of an amino acid sequence selected from the group consisting of SEQ ID NOs: 6, 13, 55 and 59, and (3) a polypeptide having an amino acid sequence substantially equivalent to a polypeptide of an amino acid sequence selected from the group consisting of SEQ ID NOs: 6, 13, 55 and 59.

[14] A process for preparing an envelope virus or inactivated envelope virus containing a foreign substance within an envelope, which comprises the steps consisting of (1) mixing an envelope virus or inactivated envelope virus with a protein comprising (a) a polypeptide having an affinity for one or more envelope viral components in combination with (b) a polypeptide capable of binding to one or more foreign substances to be introduced into a cell, (2) subjecting the resultant mixture from the above step (1), to a treatment affecting the permeability of envelopes, and (3) mixing the resultant product from the above step (2), with one or more foreign substances.

[15] A process for preparing an envelope virus or inactivated envelope virus containing a foreign substance within an envelope, which comprises the steps consisting of (1) mixing a protein comprising (a) a polypeptide having an affinity for one or more envelope viral components in combination with (b) a polypeptide capable of binding to one or more foreign substances to be introduced into a cell, with one or more foreign substances to form a complex, (2) mixing the resultant mixture from the above step (1), with an envelope virus or inactivated envelope virus, and (3) subjecting the resultant mixture from the above step (2), to a treatment affecting the permeability of envelopes.

[16] The process according to the above [14] or [15], wherein the protein comprising said polypeptide (a) in combination with the polypeptide (b) is a fusion protein.

[17] The process according to the above [14] or [15], wherein said foreign substance is an antibody.

[18] A method for introducing one or more foreign substances into a cell with an envelope virus or inactivated envelope virus, which comprises the steps consisting of (1) mixing an envelope virus or inactivated envelope virus with a protein comprising (a) a polypeptide having an affinity for one or more envelope viral components in combination with (b) a polypeptide capable of binding to one or more foreign substances to be introduced into a cell, (2) subjecting the resultant mixture from the above step (1), to a treatment affecting the permeability of envelopes, (3) mixing the resultant product from the above step (2) with one or more foreign substances, and (4) contacting the resulting foreign substance-containing envelope virus or inactivated envelope virus from the above step (3), with one or more cells.

[19] A method for introducing one or more foreign substances into a cell with an envelope virus or inactivated envelope virus, which comprises the steps consisting of (1) mixing a protein comprising (a) a polypeptide having an affinity for one or more envelope viral components in combination with (b) a polypeptide capable of binding to one or more foreign substances to be introduced into a cell, with one or more foreign substances to form a complex, (2) mixing the resultant mixture from the above step (1), with an envelope virus or inactivated envelope virus, (3) subjecting the resultant mixture from the above step (2), to a treatment affecting the permeability of envelopes and (4) contacting the resulting foreign substance-containing envelope virus or inactivated envelope virus from the above step (3), with one or more cells.

[20] The process according to the above [18] or [19], wherein the protein comprising said envelope viral component-affinity polypeptide (a) in combination with the foreign substance-binding polypeptide (b) is a fusion protein.

[21] The process according to the above [18] or [19], wherein said foreign substance is an antibody.

[22] A complex composed of (i) a protein comprising (a) a polypeptide having an affinity for one or more envelope viral components in combination with (b) a polypeptide capable of binding to one or more foreign substances to be introduced into a cell, and (ii) one or more foreign substances to be introduced into one or more cells.

ADVANTAGEOUS PROFILES OF THE INVENTION

In accordance with the present invention, proteins, antibodies and other foreign substances (non-self or exogenous substances) can be introduced into cells via simple operations without damaging their function, property and structure. When the foreign substance is an antibody, a variety of substances bound to the antibodies can be transferred into cells. Antibodies against various intracellular materials can also be introduced and the function of such intracellular materials can be regulated. Further, antibodies against substances to be administered from the outside of cells as well as metabolites thereof and others can be introduced and therefore the intracellular physiological activity of said substance can also be regulated.

The above objects and other objects, features, advantages, and aspects of the present invention are readily apparent to those skilled in the art from the following disclosures. It should be understood, however, that the disclosures in the specification including the following best modes of carrying out the invention, examples, and others are illustrating preferred embodiments of the present invention and given for purposes of illustration only. It will become apparent to the skilled in the art that a great number of variations and/or alterations (or modifications) of this invention may be made based on knowledge from the disclosure in the following parts and other parts of the specification without departing from the spirit and scope thereof as disclosed herein. All of the patent publications and reference documents cited herein for illustrative purposes are hereby incorporated by reference into the present disclosure.

BEST MODES OF CARRYING OUT THE INVENTION

Figure 1:
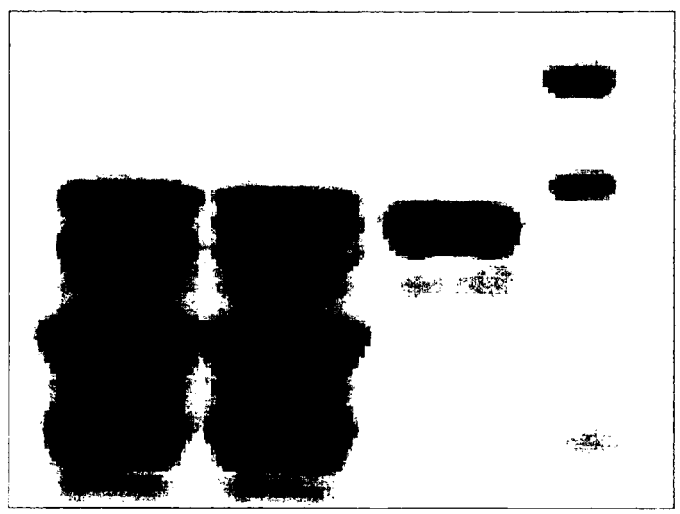
FIG. 1 shows SDS-PAGE patterns for ZZ-NP-containing inactivated HVJ envelope (lane 2), inactivated HVJ envelope alone (lane 1), ZZ-NP alone (lane 3), and molecular markers (lane 4).

The envelope viruses that can be used herein include a variety of viruses as long as they have an envelope. It is known that the envelope virus delivers nucleic acid molecules, nucleocapsid proteins and others into host cells. Such viruses include those belonging to a viral family selected from the group consisting of Retroviridae, Togaviridae, Coronaviridae, Flaviviridae, Paramyxoviridae, Orthomyxoviridae, Bunyaviridae, Rhabdoviridae, Poxviridae, Herpesviridae, Baculoviridae and Hepadnaviridae. Preferable viruses are those in the family Paramyxoviridae or Orthomyxoviridae, more preferably Paramyxoviridae. Still more preferred viruses are those belonging to the subfamily Paramyxovirinae. The virus of the Paramyxovirinae includes those of the genus *Respirovirus*, the genus *Rubulavirus*, and the genus *Morbillivirus*. Among them, viruses of the genus *Respirovirus* are preferable, more preferably Sendai virus. The terms "Sendai virus" and "HVJ" (Hemagglutinating virus of Japan) are interchangeably used herein.

The "inactivated" as used herein refers to inactivation of genomes when stated in connection with viruses. The inactivated virus is replication-defective. The genome inactivation can be achieved by, for example, UV or alkylating agent treatments. Any of envelope viruses and inactivated envelope viruses can be used herein, and the inactivated envelope viruses are more desirable. The phrases inactivated envelope viruses and inactivated viral envelopes are interchangeably used herein.

The inventive proteins are those each comprising (a) a polypeptide having an affinity for (compatible to) one or more envelope viral components (or viral constituents) in combination with (b) a polypeptide capable of binding to one or more foreign substances (or exogenous molecules) to be introduced (or transferred) into one or more cells. The polypeptide (a) is a polypeptide facilitating, through binding to the polypeptide (b), the state wherein said foreign substance is "enclosed within an envelope" or "incorporated into the inner space of an envelope". The polypeptide (a) is also a polypeptide elevating the level of said foreign substance enclosed within the envelope. The aforementioned polypeptides (a) and (b) may be in the form of a complex wherein each polypeptide (a) is interacted with each polypeptide (b) to form a subunit, or in the form of a single fusion protein. The fusion proteins are more desirable.

The "envelope" as used herein refers to a lipid bilayer-based membrane (or membranous structure) which surrounds the nucleocapsid existing in the envelope virus. The phrase, a specific substance (or specific molecule) is "enclosed within an (or the) envelope", means that such a specific substance (or specific molecule) is present in an aqueous phase with which the inner space surrounded by the aforementioned lipid bilayer-based membranous structure is filled up, and/or, in the lipid of the membranous structure, being considered to be dependent on the surface properties (such as hydrophilicity or hydrophobicity) of proteins or foreign substances to be transferred into cells. It is desired that said substances are placed mainly in the aqueous layer inside the envelope of the inactivated virus. Further, the "incorporated in the envelope" as used herein means that a substance becomes "enclosed within the envelope" as aforementioned.

The above-described envelope viral components include proteins existing on or in the surface of the envelope, phosphorylated (P) proteins, matrix (M) proteins, nucleic acids, proteins associated with the nucleic acid, etc. Embodiments of the above-described polypeptide (a) are proteins, or peptide fragments thereof, which have an affinity for (or are compatible to) one or more members selected from the group consisting of proteins existing on or in the surface of the envelope, phosphorylated proteins, matrix proteins, nucleic acids, and proteins associated with the nucleic acid. Preferably, the above-described polypeptide (a) is a protein, or a peptide fragment thereof, which is compatible to (or has an affinity for) one or more virus components existing in the inside of the envelope, more preferably a protein, or a peptide fragment thereof, which has an affinity for (or is compatible to) one or more members selected from the group consisting of the phosphorylated protein, the matrix protein, the nucleic acid, and the protein associated with the nucleic acid. A more preferred embodiment of the polypeptide (a) is an envelope viral nucleocapsid protein, or a peptide fragment thereof.

The nucleocapsid protein (abbreviated to "NP"), derived from Sendai virus which is a preferred example of the envelope virus, has an affinity for the protein existing in the inside of the virus envelope and the virus nucleic acid (RNA). The NP has also an affinity for interactions between the nucleocapsid proteins and allows the formation of complexes within the virus wherein the NP is closely associated with the nucleic acid. The Sendai virus nucleocapsid protein includes preferably polypeptides of an amino acid sequence of SEQ ID NO: 2 or an amino acid sequence substantially identical thereto, or peptide fragments (partial peptides) thereof. The peptide fragments are those each having an amino acid sequence selected from SEQ ID NOs: 27, 29, 31, and 33.

The above described (b) polypeptide capable of binding to one or more foreign substances (foreign substance-binding polypeptide (b)) may be any as long as it is a polypeptide comprising an amino acid sequence capable of binding to the foreign substance, and can be suitably selected, depending on the foreign substances to be treated. The foreign substance to be transferred into one or more cells includes nucleic acid molecules, proteins, polysaccharides and lipids, preferably proteins, and more preferably antibodies. For instance, when the foreign substance is nucleic acid, the polypeptide (b) includes basic amino acid-rich polypeptides, polypeptides which can bind to the specific sequence of genes and others. Embodiments of such polypeptides are DNA-binding sequences such as GAL4. When the foreign substances are materials labeled with a biotin-related molecule having an imidazoline ring, the polypeptide (b) includes avidins such as egg white-derived avidin, and streptavidin derived from bacteria. When the foreign substances are antibodies, the polypeptide (b) includes polypeptides capable of binding to an antibody (Ab) (antibody-binding polypeptides) or peptide fragments thereof. Desirable embodiments of the Ab-binding polypeptide are immunoglobulin-binding proteins and peptide fragments thereof. More preferable examples of the antibody-binding polypeptide are proteins capable of binding to an antibody Fc region or kappa (κ) light chain and peptide fragments thereof. These proteins or peptide fragments thereof can be suitably selected depending on antibodies to be bound. Where the antibody (Ab) is a single-chain antibody or a molecule wherein the variable domains of the light and heavy chains are joined by a flexible peptide linker, κ light chain-binding molecules will be selected. More specifically, they include Fc region-binding molecules, Protein A, Protein G, and Protein A/G; κ light chain-binding molecules, Protein L; amino acid sequences substantially identical thereto or peptide fragments thereof. These immunoglobulin-binding proteins used herein may be whole protein units, or immunoglobulin-binding sequence fragments of such proteins. It is desirable that the aforementioned binding sequences are amino acid sequences which bind to an Fc region or κ light chain. The Fc region-binding sequence includes amino acid sequences for the A, B, C, D, and E regions of Protein A, said B region-derived Z region, and the C1, C2, and C3 regions of Protein G, and amino acid sequences substantially identical thereto. It is possible to use the member of such species alone or in combination with one or more sequences selected from the aforementioned sequences. More desirable examples thereof are the Z region having an amino acid sequence of SEQ ID NO: 4, the Protein G C1 region having an amino acid sequence of SEQ ID NO: 49, the Protein L B1 region having an amino acid sequence of SEQ ID NO: 51, and amino acid sequences substantially identical thereto.

As above-described, the polypeptide (a) may be joined with the polypeptide (b) to form a fusion protein. Alternatively, they may be in the form of a complex wherein each polypeptide (a) is associated with each polypeptide (b) to form a subunit. The fusion proteins are more preferable. Such fusion proteins are molecules each comprising (a) the polypeptide having an affinity for one or more envelope viral components in combination with (b) the foreign substance-binding polypeptide, as aforementioned, wherein the polypeptide (b) may be positioned at either the N-terminal end (amino-terminal side) or the C-terminal end (carboxyl-terminal side) of the polypeptide (a). More desirable embodiments are fusion proteins wherein the polypeptide (b) is positioned at the N terminal end of the polypeptide (a). The fusion protein may contain a spacer region between the polypeptides (a) and (b) for avoiding interference due to steric hindrance. The spacer region may be a glycine spacer, or composed of glycine and serine.

More specific embodiments of the fusion proteins include the following:
(1) molecules each comprising a basic amino acid-rich polypeptide at the N-terminal end of the amino acid sequence of SEQ ID NO: 2, or an amino acid sequence substantially identical thereto.
(2) molecules each comprising a DNA-binding sequence, such as GAL4, at the N-terminal end of the amino acid sequence of SEQ ID NO: 2, or an amino acid sequence substantially identical thereto.
(3) molecules each comprising any amino acid sequence of avidins at the N-terminal end of the amino acid sequence of SEQ ID NO: 2, or an amino acid sequence substantially identical thereto.
(4) molecules each comprising an antibody-binding protein or a peptide fragment thereof at the N-terminal end of the amino acid sequence of SEQ ID NO: 2, or an amino acid sequence substantially identical thereto.

Preferable examples of the fusion protein molecule (4) are proteins each comprising an amino acid sequence of SEQ ID NO: 6, 13, 15, 17, 19, 53, 55, 57 or 59, or an amino acid sequence substantially identical thereto, more preferably proteins each comprising an amino acid sequence of SEQ ID NO: 6, 13, 55 or 59, or an amino acid sequence substantially identical thereto.

The phrase "amino acid sequence substantially identical" as used herein refers to amino acid sequences that have at least about 70%, preferably about 80%, more preferably about 90%, most preferably about 95% or higher amino acid residue identity (or homology).

As used herein, the term "identity" or "homology" means the percentage (%) of identical amino acid and similar amino acid residues as compared to all overlapped amino acid residues in optimal alignment of two amino acid sequences, when aligned using one of mathematical algorithms known in the art (preferably, said algorithm can take into account the presence of gaps, which need to be introduced into one or both sequences for the optimal alignment). The "similar amino acid" refers to amino acids of like characteristics (e.g., physical and chemical properties), which include those classified into the same group, such as aromatic amino acids (Phe, Trp, Tyr), aliphatic amino acids (Ala, Leu, Ile, Val), polar amino acids (Gln, Asn), basic amino acids (Lys, Arg, His), acidic amino acids (Glu, Asp), hydroxyl group-containing amino acids (Ser, Thr), and small-sized side chain amino acids (Gly, Ala, Ser, Thr, Met). Replacements among such similar amino acids will be likely to be phenotypically silent in a protein (i.e., conservative amino acid substitutions). Embodiments of the conservative amino acid substitution are well known in the art and found in a variety of documents (see, for instance, Bowie et al., Science, 247: 1306-1310 (1990)).

An example of algorithm that is suitable for determining amino acid sequence homology is the algorithm described in Karlin et al., Proc. Natl. Acad. Sci. USA, 90: 5873-5877 (1993), but not limited to.

Preferred examples of the "protein comprising an amino acid sequence substantially identical thereto" herein are proteins that are substantially identical in both amino acid sequence levels and qualitative activities, and the like.

The proteins according to the present invention encompass modified proteins (so-called "muteins") comprising any of (1) deleted amino acid sequences which have one or more deletions of one or more amino acid residues (preferably about 1 to 30, still preferably about 1 to 10, and further preferably several (1 to 5) amino acid residues); (2) added amino acid sequences which have one or more additions of one or more amino acid residues (preferably about 1 to 30, still preferably about 1 to 10, and further preferably several (1 to 5) amino acid residues); (3) inserted amino acid sequences which have one or more insertions of one or more amino acid residues (preferably about 1 to 30, still preferably about 1 to 10, and further preferably several (1 to 5) amino acid residues); (4) substituted amino acid sequences which have one or more substitutions of one or more amino acid residues (preferably about 1 to 30, still preferably about 1 to 10, and further preferably several (1 to 5) amino acid residues) with one or more other amino acid residues; and (5) combinations wherein the aforementioned one or more amino acid deletions, additions, insertions and substitutions are associated one another. Where the amino acid sequence is inserted, deleted or substituted as aforementioned, a position modified by the insertion, deletion, or substitution is not limited to, as long as the resultant modified molecule retains the activity of the unmodified protein.

Herein, protein or peptide sequences are written in the N-terminal end to C-terminal end direction from left to right according to the conventional peptide notation. The protein of the present invention is any of molecules having a carboxyl (—COOH), carboxylate (—COO$^-$), amide (—CONH$_2$) or ester (—COOR) group at the C-terminal end. For the ester used herein, R is a $C_{1-6}$ alkyl group such as methyl, ethyl, n-propyl, isopropyl, and n-butyl; a $C_{3-8}$ cycloalkyl group such as cyclopentyl and cyclohexyl; a $C_{6-12}$ aryl group such as phenyl and α-naphtyl; a $C_{7-14}$ aralkyl group including a phenyl-$C_{1-2}$ alkyl group such as benzyl and phenethyl, and an α-naphtyl-$C_{1-2}$ alkyl group such as α-napthylmethyl; a pivaloyloxymethyl group, etc. When the protein of the present invention has a carboxyl (or carboxylate) group at a site other than the C-terminal end, protein molecules wherein the carboxyl group is amidated or esterified are also included therein. In such cases, the ester as used herein is selected from those listed in connection with the aforementioned C-terminal end ester. Further, the proteins of the present invention also encompass protein molecules wherein the amino group of the N-terminal amino acid residue is protected with a protective group (for example, $C_{1-6}$ acyl including $C_{1-6}$ alkanoyl such as formyl and acetyl), those molecules wherein the N-terminal glutamine residue generated through in vivo cleavage is pyroglutamated, those molecules wherein a substituent on an intermolecular amino acid side chain (e.g., —OH, —SH, an amino group, an imidazole group, an indole group, a guanidino group and the like) is protected with a suitable protective group (e.g., $C_{1-6}$ acyl including $C_{1-6}$ alkanoyl such as formyl and acetyl), conjugated proteins such as so-called glycoproteins having one or more saccharide chains.

The subject protein-encoding DNA includes, for example, DNA molecules having a nucleotide sequence of SEQ ID NO: 5, 12, 14, 16, 18, 48, 50, 52, 54, 56 or 58, or DNA molecules that not only have a nucleotide sequence capable of hybridizing to said nucleotide sequence under high-stringent conditions but also encode a protein with the substantially same nature of activity, and others. The DNA molecule, used herein, that is capable of hybridizing to said nucleotide sequence under high-stringent conditions includes DNA comprising a nucleotide sequence with at least about 50%, preferably at least about 60%, more preferably at least about 70%, particularly preferably at least about 80%, most preferably at least about 90% or higher homology to said nucleotide sequence. The hybridization can be performed according to methods known per se or equivalent techniques, for instance, the method disclosed in J. Sambrook et al., Molecular Cloning, Second Edition, Cold Spring Harbor Lab. Press, 1989, etc. When commercially available libraries are used, the hybridization can be carried out according to methods described in manuals attached thereto. Preferably, the hybridization can be achieved under high-stringent conditions. High-stringent hybridization conditions referred to herein are conditions in about 19 to 40 mM, preferably about 19 to 20 mM, sodium salt at about 50 to 70° C., preferably about 60 to 65° C. Particularly, preferable high-stringent conditions are those in about 19 mM sodium salt at about 65° C.

DNA sequences can be converted with any of known kits including, for instance, Mutan™-Super Express Km (Takara Shuzo, Tokyo, Japan), Mutan™-K (Takara Shuzo, Tokyo, Japan) and other kits, based on methods known per se, such as ODA-LA PCR method, Gapped duplex method, and Kunkel method, or equivalent techniques. Cloned DNA can be used without any modification, or after, as desired, digestion with restriction enzymes and/or addition of linkers, depending on targeted subjects. The DNA may include the ATG translation initiation codon at the 5'-end and the translation stop codon, TAA, TGA or TAG, at the 3'-end. These translation initiation and stop codons can be added using suitable synthetic DNA adaptors.

Expression vectors that comprise DNA coding for a protein within the scope of the present invention can be constructed, for example, as follows: a DNA molecule that encodes the protein of the present invention is cut to give a target DNA fragment which is then inserted into a suitable expression vector downstream of a promoter in the vector. The expression vector used herein includes $E.$ $coli$-derived plasmids (e.g., pBR322, pBR325, pUC12, pUC13, and pET28a); $Bacillus$ $subtilis$-derived plasmids (e.g., pUB110, pTP5, and pC194); yeast-derived plasmids (e.g., pSH19, and pSH15); insect cell expression plasmids (e.g., pFast-Bac); animal cell expression plasmids (e.g., pA1-11, pXT1, pRc/CMV, pRc/RSV, and pcDNAI/Neo); bacteriophages such as λ phage; insect viral vectors such as baculoviral vectors (e.g., BmNPV, and AcNPV); viral vectors derived from animal viruses such as retro-viruses, vaccinia viruses, and adeno-viruses.

Any promoter may be employed as long as it serves as a suitable promoter for hosts used in gene expression. When hosts are animal cells, examples of such promoters used herein are the SRα promoter, the SV40 or LTR promoter, the CMV (cytomegalovirus) and RSV (Rous sarcoma virus) promoters, MoMuLV (Moloney murine leukemia virus) LTR, the herpes simplex virus thymidine kinase promoter (HSV-TK), etc. Among them, the CMV promoter, the SRα promoter and the like are preferable.

When hosts are members of the genus $Escherichia$, trp promoter, lac, recA, $\lambda_{PL}$, lpp, T7 promoters and others are preferable. When hosts are members of the genus $Bacillus$, SPO1, SPO2, penP promoters and others are preferable. When hosts are yeast members, PHO5, PGK, GAP, ADH promoters and others are preferred. For insect host cells, the polyhedrin promoter, the P10 promoter and others are preferable.

The expression vector which can be used herein includes, in addition to the above, those comprising, if desired, an enhancer, a polyadenylation signal, a selectable marker, the SV40 origin of replication (hereinafter, often abbreviated to SV40 ori) and the like. The selectable marker includes, for example, a dihydrofolate reductase gene (hereinafter, often abbreviated to dhfr, resistant to methotrexate (MTX)), ampicillin-resistant gene (hereinafter, often abbreviated to ampr), neomycin-resistant gene (hereinafter, often abbreviated to neor, resistant to G418) and others. Particularly, when dhfr gene-deficient Chinese hamster cells are used together with the dhfr gene as a selectable marker, the target gene may also be selected with a thymidine-free medium. If necessary, a nucleotide sequence coding for a signal sequence (signal codons) suitable for a host may be added to the 5'-terminal side of DNA encoding the protein or peptide fragment according to the present invention (or the native signal codons may be replaced with signal codons compatible with the host). For example, a PhoA signal sequence, an OmpA signal sequence, or the like, can be used for $Escherichia$ sp. hosts; an α-amylase signal sequence, a $subtilis$ in signal sequence, or the like, for $Bacillus$ sp. hosts; an MFα signal sequence, a SUC2 signal sequence, or the like, for yeast hosts; and an insulin signal sequence, an α-interferon signal sequence, an antibody molecule signal sequence, or the like, for animal cell hosts, respectively.

The $Escherichia$ sp. used herein includes, for example, $Escherichia$ $coli$ K12.DH1 [Proc. Natl. Acad. Sci. USA, Vol. 60, 160 (1968)], $Escherichia$ $coli$ JM103 [Nucleic Acids Research, Vol. 9, 309 (1981)], $Escherichia$ $coli$ JA221 [Journal of Molecular Biology, Vol. 120, 517 (1978)], $Escherichia$ $coli$ HB101 [Journal of Molecular Biology, Vol. 41, 459 (1969)], $Escherichia$ $coli$ C600 [Genetics, Vol. 39, 440 (1954)], and $Escherichia$ $coli$ Rosetta (DE3) [Novagen]. The $Bacillus$ sp. used herein includes, for example, $Bacillus$ $subtilis$ MI114 [Gene, Vol. 24, 255 (1983)], $Bacillus$ $subtilis$ 207-21 [Journal of Biochemistry, Vol. 95, 87 (1984)]. The yeast used herein includes, for example, $Saccharomyces$ $cerevisiae$ AH22, AH22R⁻, NA87-11A, KDK-5D, 20B-12, $Schizosaccharomyces$ $pombe$ NCYC1913, NCYC2036, and $Pichia$ $pastoris$ KM71. The insect cells used herein include, for example, when a virus is AcNPV, established insect cell lines, $Spodoptera$ $frugiperda$ cells (Sf cells), derived from a larva of cabbage army worm ($Spodoptera$ $frugiperda$), MG1 cells, derived from the midgut of $Trichoplusia$ $ni$, High Five™ cells, derived from an egg of $Trichoplusia$ $ni$, cells derived from $Mamestra$ $brassicae$, cells derived from $Estigmena$ $acrea$ and others. When a virus is BmNPV, the insect cells used herein are established cell lines derived from silkworm ($Bombyx$ $mori$ N cells; BmN cells) and the like. Examples of the Sf cells used herein are Sf9 cells (ATCC CRL1711), and Sf21 cells (both, Vaughn, J. L. et al., In Vivo, 13, 213-217 (1977)). Examples of the insects used herein are silkworm larva [Maeda et al., Nature, Vol. 315, 592 (1985)] and the like.

The animal cells used herein include, for example, monkey COS-7 cell lines, monkey Vero cells, Chinese hamster ovary (CHO) cells (hereinafter, abbreviated to CHO cells), dhfr gene-deficient Chinese hamster cell CHO (hereinafter, abbreviated to CHO (dhfr⁻) cell), mouse L cells, mouse AtT-20 cells, mouse myeloma cells, rat GH3 cells, human FL cells and other cells.

Transformation (transfection) can be performed according to known methods, depending on a variety of hosts. *Escherichia* sp. bacteria can be transformed according to the methods disclosed in, for example, Proc. Natl. Acad. Sci. USA, Vol. 69, 2110 (1972) and Gene, Vol. 17, 107 (1982). *Bacillus* sp. bacteria can be transformed according to the methods disclosed in, for example, Molecular & General Genetics, Vol. 168, 111 (1979). Yeast cells can be transformed according to the methods disclosed in, for example, Methods in Enzymology, Vol. 194, 182-187 (1991); Proc. Natl. Acad. Sci. USA, Vol. 75, 1929 (1978) and others. Insect cells and insects can be transformed according to the method disclosed in, for example, Bio/Technology, Vol. 6, 47-55 (1988). Animal cells can be transformed according to the methods disclosed in, for example, Saibo Kougaku Bessatsu 8 Shin-Saibo Kougaku Jikken Purotokoru (Cell Technology Separate Volume 8 Novel Experimental Protocols for Cell Technology), 263-267 (1995, Shujunsha Co., Ltd., Tokyo, Japan), and Virology, Vol. 52, 456 (1973).

Cultivation of transformants or transfectants can be performed according to conventional techniques depending on a variety of hosts. For example, the transformant (transfectant) in which the host is *Escherichia* sp. or *Bacillus* sp. can be cultivated suitably in a liquid culture medium. A preferred culture medium may contain carbon sources, nitrogen sources, minerals, and other elements, necessary for growing the transformant. The carbon source may include, for example, glucose, dextrin, soluble starch, sucrose, etc. The nitrogen source may include, for example, organic or inorganic substances such as ammonium salts, nitrates, corn steep liquor, peptone, casein, meat extracts, soybean-cakes, potato extracts. Examples of the minerals are calcium chloride, sodium dihydrogen phosphate, magnesium chloride, etc. It may also be supplemented with yeast extracts, vitamins, growth promoting factors, etc. The pH of the medium is desirably about 5 to 8. A preferable example of the medium for culturing transformants wherein the host is *Escherichia* sp. is an M9 medium containing glucose and casamino acid (Miller, Journal of Experiments in Molecular Genetics, 431-433, Cold Spring Harbor Laboratory, New York 1972). If necessary, the medium may be supplemented with a drug such as 30-indolyl acrylic acid in order to make a promoter work efficiently. When the host is *Escherichia* sp., the transformant is usually cultured at about 15 to 43° C. for about 3 to 24 hr. If necessary, aeration and stirring may be optionally applied.

When the host is *Bacillus* sp., the transformant is usually cultured at about 30 to 40° C. for about 6 to 24 hr. If necessary, aeration and stirring may be optionally applied.

When the host is yeast, examples of the medium for culturing the transformant are Burkholder minimum medium [Bostian, K. L. et al., Proc. Natl. Acad. Sci. USA, Vol. 77, 4505(1980)], SD medium containing 0.5% casamino acid [Bitter, G. A. et al., Proc. Natl. Acad. Sci. USA, Vol. 81, 5330 (1984)], and others. The pH of the medium is desirably about 5 to about 8. Culturing is performed usually at about 20° C. to 35° C. for about 24 to 72 hr. If necessary, aeration and stirring may be optionally applied.

The medium used herein for culturing the transformant whose host is an insect cell or insect includes, for example, Grace's Insect Medium [Grace, T. C. C., Nature, Vol. 195, 788 (1962)] appropriately supplemented with an additive such as 10% inactivated bovine serum. The pH of the medium is desirably about 6.2 to 6.4. Cultivation is usually carried out at about 27° C. for about 3 to 5 days. If necessary, aeration and stirring may be optionally applied.

The medium used herein for culturing the transformant whose host is an animal cell includes, for example, about 5 to 20% fetal bovine serum-containing minimum essential medium (MEM) [Science, Vol. 122, 501 (1952)], Dulbecco's modified Eagle's medium (DMEM) [Virology, Vol. 8, 396 (1959)], RPMI 1640 medium [The Journal of the American Medical Association, Vol. 199, 519 (1967)], 199 medium [Proceeding of the Society for the Biological Medicine, Vol. 73, 1 (1950)] and others. The pH of the medium is desirably about 6 to 8. Cultivation is usually carried out at about 30° C. to 40° C. for about 15 to 60 hr. If necessary, aeration and stirring may be optionally applied.

The protein of the present invention can be extracted, isolated and/or purified from the resulting culture of said transformant according to methods known per se. For example, when the proteins of the present invention are extracted from cultured bacteria or cell cytoplasms, the following techniques are appropriately used: the bacteria or cells are collected by a known method, next suspended in a suitable buffer, and then disrupted by sonication, lysozyme digestion and/or freeze-thawing, followed by centrifugation or filtration to afford a crude soluble protein extract. Other conventional extraction or isolation methods can also be applied. The buffer may contain a protein-denaturing agent such as urea or guanidine hydrochloride, or a detergent such as Triton X-100. When the proteins of the present invention are extracted from the membrane fraction, the following processes are used: the bacteria or cells are disrupted in the same manner as aforementioned, and centrifuged at low speed to remove precipitated cell debris. The resultant supernatant is then centrifuged at high speed to precipitate a cell membrane-containing fraction (if necessary, the cell membrane fraction may be purified by density gradient centrifugation). When the proteins of the present invention are secreted outside of the microorganism (cell), culture supernatants are separated from the culture by centrifugation or filtration, and the resulting supernatants are collected.

The protein of the present invention contained in the resultant soluble fraction, membrane fraction or culture supernatant can be separated, isolated and/or purified according to methods known per se. Such techniques used herein include methods of utilizing solubility such as salting-out and solvent precipitation; methods of utilizing mainly differences in molecular size such as dialysis, ultrafiltration, gel filtration and SDS-polyacrylamide gel electrophoresis (SDS-PAGE); methods of utilizing differences in electrical charge such as ion exchange chromatography; methods of utilizing specific affinity such affinity chromatography; methods of utilizing hydrophobic differences such as reversed-phase high-performance liquid chromatography (HPLC); methods of utilizing different isoelectric points such as isoelectric focusing; and other methods. These methods can be appropriately combined.

When the protein or peptide is in a free form, it can be converted into its salt by methods known per se or modifications thereof. When the protein or peptide is obtained in the form of a salt, it can be converted into the free form or the form of another salt by methods known per se or modifications thereof.

The protein of the present invention produced by the transformant may be subjected to treatment with a suitable protein-modifying enzyme, before or after purification, to modify it appropriately or to partly remove a polypeptide fragment. Examples of the protein-modifying enzyme used herein include trypsin, chymotrypsin, arginyl endopeptidase, protein kinase, and glycosidase. The presence of the resultant protein of the present invention is determined by enzyme immunoassay or western blot with a specific antibody.

Further, the protein of the present invention can be in vitro synthesized using, as a template, RNA corresponding to DNA coding for said protein in a cell-free protein translation system selected from the group consisting of rabbit reticulocyte lysate, wheat germ lysate, and others. Alternatively, it can be synthesized using, as a template, DNA coding for the protein of the present invention in a cell-free transcription/translation system containing RNA polymerase.

The resultant proteins, peptide fragments thereof, antibodies and other molecules obtained herein can also be labeled, if necessary. Labeling techniques are not limited to as long as they are conventionally known methods, but include preferably fluorescent labels, autoradiography, electron-dense materials, and insoluble pigment producing enzymes. Preferably, the labeling is a method of covalently binding with a fluorescent label. Fluorescent substances to be used for the fluorescent label are not limited to, but include, for example, compounds having a fluorescent group such as pyrene, an anthraniloyl group, a dansyl group, fluorescein, rhodamine, and a nitrobenzoxadiazol group. The compounds having the aforementioned fluorescent group are well known (see, for example, HIRATSUKA Toshiaki, "Tanpakushitsu Kakusan Kozo" (Protein Nucleic Acid and Enzyme), Vol. 42, No. 7 (1997), etc.), and can be incorporated into a protein molecule or peptide according to conventional methods.

The method of incorporating a foreign substance (non-self substance) into the envelope of an envelope virus or inactivated envelope virus with the protein of the present invention comprises the steps consisting of:

incorporating the protein of the present invention into the envelope, and then contacting the foreign substance (non-self substance) with the above-described virus or inactivated virus; or forming a complex consisting of the protein of the present invention and the foreign substance (non-self substance), and then incorporating the resultant complex into the envelope of said virus or inactivated virus.

1. In the case where the protein of the present invention is incorporated into the envelope virus, followed by contacting the resulting virus with the foreign substance (non-self substance), foreign substance-containing envelope viruses and inactivated envelope viruses can be obtained by the steps consisting of:

(1) mixing the envelope virus or inactivated envelope virus with a protein containing (a) a polypeptide having an affinity for an envelope viral component and (b) a polypeptide having the ability to bind to the foreign substance to be incorporated into a cell, (2) subjecting the resultant mixture from the above step (1) to a treatment affecting the permeability of the envelope, and (3) mixing the resultant product from the above step (2) with the foreign substance.

2. In the case where the protein of the present invention is admixed with the foreign substance (non-self substance) to form a complex, followed by incorporating the resultant complex into the envelope virus or inactivated envelope virus, foreign substance-containing envelope viruses and inactivated envelope viruses can be obtained by the steps consisting of:

(1) mixing a protein containing (a) a polypeptide having an affinity for an envelope viral component and (b) a polypeptide having the ability to bind to the foreign substance to be incorporated into a cell, with said foreign substance to form a complex, (2) mixing the resulting mixture from the above step (1) with the envelope virus or inactivated envelope virus, and (3) subjecting the resulting mixture from the above step (2) to a treatment affecting the permeability of the envelope.

In the above methods 1 and 2, the treatment affecting the permeability of envelopes includes freeze-thawing, sonication, surface active agent addition and others. The addition of surface active agents is more preferable. The surface active agents used herein include octylglycoside, Triton-X 100, CHAPS, NP-40, etc. They can be used alone or in the form of combinations of two or more surface active agents. When the aforementioned surface active agent addition is applied for the treatment affecting the permeability of envelopes, the final concentration of surface active agents varies depending on kinds thereof but is 0.002 to 20%, desirably 0.02 to 2%. When the surface active agent is used, it is preferable to remove the surface active agent 1 min to 1 hr later. In the application of the above method 1, it is desirable to remove the surface active agent prior to the step (3) of admixing with the foreign substance. In the application of the above method 2, it is desirable to remove the surface active agent after the step (3). The removal of surface active agents includes methods of subjecting a mixture to centrifugation and discarding supernatants. The surface active agent treatment is preferably conducted at low temperature, more preferably under ice-cooling.

Use of envelope viruses and inactivated envelope viruses that contain foreign substances (non-self substances) within their envelopes, obtained by using the proteins of the present invention, allows the incorporation of said foreign substances into one or more cells. Said foreign substances can be incorporated into one or more cells by contacting the cell or cells to be targeted for the incorporation with the envelope viruses and inactivated envelope viruses that contain the foreign substance (non-self substance) within their envelopes.

Cells to be targeted for the incorporation of foreign substances in the present invention are any of cultured cells and cells which compose tissues. Preferred target cells are cultured cells. Embodiments of the cells are any cell of mammals (e.g., human, bovine, simian, equine, swine, ovine, caprine, canine, feline, guinea pig, rat, mouse, rabbit, hamster, etc.). Examples of such cells are hepatocytes, splenocytes, neurons, gliacytes, pancreatic β cells, myelocytes, mesangial cells, Langerhans' cells, epidermic cells, epithelial cells, goblet cells, endothelial cells, smooth muscle cells, fibroblasts, fibrocytes, myocytes, fat cells (adipocytes), immune cells (e.g., macrophages, T cells, B cells, natural killer cells, mast cells, neutrophils, basophils, eosinophils, monocytes), megakaryocytes, synovial cells, chondrocytes, bone cells (osteocytes), osteoblasts, osteoclasts, mammary gland cells and interstitial cells (Leydig's cells), precursor cells of these cells, stem cells and cancer cells and other cells. The targets for the incorporation of said foreign substances may be any tissue wherein one or more members of such cells exist, including, for example, brain, any part thereof (e.g., olfactory bulb, amygdaloid nucleus, cerebral basal ganglia, hippocampus, thalamus, hypothalamus, cerebral cortex, medulla oblongata, cerebellum), spinal cord, hypophysis, stomach, pancreas, kidney, liver, gonad, thyroid, gallbladder, bone marrow, adrenal gland, skin, lung, gastrointestinal tract (e.g., large intestine and small intestine), blood vessel, heart, thymus, spleen, submandibular gland, peripheral blood, prostate, testis, ovary, placenta, uterus, bone, joint, adipose tissue (e.g., brown adipose tissue, white adipose tissue), skeletal muscle and other tissues.

The present invention will be more specifically illustrated by the following Examples, but such examples are not intended to limit the scope of the present invention.

Details of the present invention are described by the following examples but such examples are provided only for illustrative purposes, and for referential embodiments of the present invention. These examples have been described herein for the purpose of illustrating specific embodiments of the present invention but should not be construed as in any sense limiting the scope of the invention disclosed herein. It should be understood in the present invention that various embodiments can be made or executed within the spirit, scope and concept disclosed herein. All the examples were carried out or can be carried out, unless otherwise disclosed herein specifically, by standard techniques which are well known and conventional to those skilled in the art.

Example 1

Construction of Vector for Expressing Antibody-Binding ZZ Protein (Synthetic Peptide ZZ Region)

In order to utilize the antibody-binding Z region, a DNA fragment coding for the ZZ region, which is the tandem repeat dimer of said region, was inserted into the site downstream of the T7 promoter of inducible expression vector pET28a (Novagen). The above-described ZZ region DNA fragment was prepared by performing PCR using pEZZ18 (Amersham Biosciences) as a template.

Primers used in PCR were primer 1 (5'-GCAAATGC-CATGGAACACGATGAAGCCGTAGACAA-3'; SEQ ID NO: 7) and primer 2 (5'-GGATCACCAAGCTTTTAGCTC-GAATTCGCGTCTAC-3'; SEQ ID NO: 8), for generating NcoI and Hind III restriction sites at the upstream and downstream ends of the ZZ region in the resulting DNA fragment, respectively. The PCR was done using Ex Taq™ (Takara), in 50 µl of reaction solution (a reaction buffer attached to Ex Taq™, 200 KM each of dATP, dTTP, dCTP and dGTP, and 400 nM each of said primers) admixed with about 1 ng of pEZZ18. The amplification was performed using GeneAmp PCR system 9700 (PE Applied Biosystems) set to repeat steps at 94° C. for 30 sec, at 60° C. for 30 sec and at 72° C. for 30 sec, for a total of 30 cycles. The resultant DNA fragment was digested with restriction enzymes, NcoI and Hind III, and then inserted into the site derived by cleavage with NcoI and Hind III from pET28a (Novagen) to create inducible expression vector pETZZ.

Example 2

Preparation of DNA Coding for HVJ Nucleocapsid Protein

DNA coding for HVJ nucleocapsid protein was RT-PCR amplified from genome RNA of HVJ Z strain (furnished by courtesy of Professor Kaneda, Osaka University, Japan). The aforementioned virus which can be used herein is HVJ virus in HVJ-inoculated chicken egg chorioallantoic fluid obtainable in the same manner as disclosed in Example 1 of US Patent Application Publication No. 2004/0253272 A1. Purification of total RNA was done with Viral RNA Mini (Viogene) from virus-infected chicken egg chorioallantoic fluid.

Reverse transcription was carried out with Ready-To-Go™ You-Prime First-Strand Beads (Amersham Biosciences) using purified total RNA in combination with virus genome RNA-specific primers, primer 3 (5'-ACCAAACAA-GAGAAAAAACATGTAT-3'; SEQ ID NO: 9). In the RT reaction step, 20 µl of RNase free water was added to 10 µl of total RNA solution (16 ng/µl) and the resultant mixture was allowed to stand at 65° C. for 10 min, and then put on ice for 2 min. The resulting mix was added to First-Strand Reaction Mix Beads, admixed with 3 µl of primer 3 (10 µM), and then allowed to stand at 37° C. for 1 hr to give a virus genome cDNA solution.

PCR was performed using as a template the resulting virus genome cDNA from the above reaction in combination with primers, primer 4 (5'-TGCCAAAGGATCCGATGGC-CGGGTTGTTGAGCACC-3'; SEQ ID NO: 10) and primer 5 (5'-GCCTCGTCTCGAGCTAGATTCCTCCTAC-CCCAGCT-3'; SEQ ID NO: 11), for generating BamH I and Xho I restriction sites at the upstream and downstream ends of the DNA region coding for the nucleocapsid protein in the resulting DNA fragment, respectively. The PCR was done using Ex Taq™ (Takara) in 49 µl of reaction solution (a reaction buffer attached to Ex Tag™, 200 µM each of dATP, dTTP, dCTP and dGTP, and 400 nM each of said primers) admixed with 1 µl of the virus genome cDNA solution. The amplification was performed using GeneAmp PCR system 9700 (PE Applied Biosystems) set to repeat steps at 94° C. for 30 sec, at 60° C. for 30 sec and at 72° C. for 2 min, for a total of 30 cycles. As a result, a DNA sample (1 µg) containing DNA coding for the nucleocapsid protein was obtained.

Example 3

Preparation of Plasmid for Expressing Fusion Protein Composed of ZZ Protein and HVJ Nucleocapsid Protein HVJ nucleocapsid protein-encoding DNA was inserted into the downstream site of the ZZ protein-encoding DNA sequence of pETZZ, obtained in the above Example 1, to create plasmid pETZZNP for expressing fusion proteins. The DNA fragment, obtained in the above Example 2, was cleaved with BamH I and Xho I, and then inserted into the site, derived by cleavage with BamH I and Xho I from pETZZ, to create plasmid pETZZNP for expressing a fusion protein (ZZ-NP) with HVJ nucleocapsid protein on the C-terminal end of ZZ protein.

Example 4

Preparation of Fusion Protein Composed of ZZ Protein and HVJ Nucleocapsid Protein Fusion protein ZZ-NP was inducibly expressed in *E. coli* using T7 expression system. *E. coli* Rosetta (DE3) (Novagen) was transformed with pETZZNP, obtained in the above Example 3, and the resulting transformants (transformed cells) were incubated in LB culture medium (30 ml) containing kanamycin (final concentration: 20 µg/ml) and chloramphenicol (final concentration: 34 µg/ml) at 37° C. overnight. The resultant culture was used as a preculture solution. This preculture solution was transferred in 1 L of LB culture medium containing kanamycin (final concentration: 20 µg/ml) and chloramphenicol (final concentration: 34 µg/ml), and incubated. When the culture was grown to $OD_{600}$=0.6, expression was induced by adding 1 ml of 1M IPTG solution. After further incubation at 37° C. for 4 hr, the culture was centrifuged (at 4° C., 6,000 rpm for 15 min), and cells were collected and stored overnight at −20° C. The resultant cells were suspended in 20 ml of TST solution (50 mM Tris, pH7.6, 150 mM NaCl, 0.05% Tween 20) and then disrupted by sonication. The crude extract was centrifuged (at 4° C., 20,000 g for 30 min), and the resulting supernatant was subjected to affinity purification using IgG Sepharose™ 6 Fast Flow (Amersham Biosciences) according to attached manuals. The column was equilibrated with 0.5M acetic acid (pH3.4), TST (50 mM Tris buffer, pH7.6, 150 mM NaCl, 0.05% Tween 20) and loaded with the above supernatant. The column was washed with TST, 5 mM $NH_4Ac$ (pH5.0), and then eluted with 0.5M acetic acid (pH3.4). The fusion protein containing eluate (2 ml) was dialyzed against 300 mL of PBS for 2 hr, and further against 300 ml of PBS overnight, with dialysis membrane, Spectra/Por Membrane MWCO: 1,000 (Spectrum). After the dialysis, the resulting fusion protein solution (2 ml) was sterilized by filtration through a 0.22 μm filter. A fusion protein ZZ-NP solution (2 ml) with the fusion protein ZZ-NP concentration of 2 mg/mL was obtained.

Example 5

Preparation of Fusion Protein ZZ-NP-Containing Inactivated HVJ Envelope

To 20 μl of a 25HAU/μl inactivated HVJ envelope (GenomONE™, Ishihara Sangyo Kaisha, Ltd., Japan) solution was added 20 μl of fusion protein ZZ-NP solution (adjusted to 2 mg/ml), obtained in the above Example 4, and the resultant solution was mixed. To the mixture was added 4 μl of 2% Triton X-100 solution, and centrifuged immediately (at 4° C., 10,000 g, for 5 min). After the centrifugation, supernatants were removed, PBS was gently added at a dose of 20 μl, and the mixture was recentrifuged (at 4° C., 10,000 g, for 5 min). After the centrifugation, supernatants were removed, and free ZZ-NP was removed. To the resultant pellets was added 10 μl of PBS to form a suspension. To the above suspension was also added 10 μl of 2×sample buffer and the mixture was boiled for 5 min. The resulting mixture was applied to SDS-PAGE (10% acrylamide gel), and CBB staining was done after the electrophoresis (FIG. 1, Lane 2). For control groups, inactivated HVJ envelope wherein the same operations were done except that no ZZ-NP is used (FIG. 1, lane 1) and ZZ-NP alone (FIG. 1, lane 3) were electrophoresed.

On lane 1, no band corresponding to ZZ-NP is observed. In contrast, a band corresponding ZZ-NP is verified on lane 2, indicating that fusion protein ZZ-NP containing inactivated HVJ envelopes have been obtained by the above treatment.

Example 6

Preparation of Mouse IgG-Containing Inactivated HVJ Envelope

Figure 2:
FIG. 2 shows Western blotting patterns for mouse IgG-containing inactivated HVJ envelopes. Lane 4 to 6: mouse IgG enclosed within ZZ-NP-containing inactivated HVJ envelopes. Lane 1 to 3: mouse IgG Ab alone (⅓ µg, 1 µg, and 3 µg, respectively).

To 10 μl of a 25HAU/μl inactivated HVJ envelope (GenomONE™, Ishihara Sangyo Kaisha, Ltd., Japan) suspension was added 10 μl of ZZ-NP solution (predetermined ZZ-NP concentration: 0.08 to 2 mg/ml) and the resultant solution was mixed. To the mixture was added 2 μl of 2% Triton X-100 solution, and centrifuged immediately (at 4° C., 10,000 g, for 5 min) to remove supernatants. The resulting ZZ-NP-containing inactivated HVJ envelope was suspended in 10 μl of antibody solution (1 mg/ml Mouse IgG (SIGMA), PBS) and then allowed to stand on ice for 5 min. The suspension was centrifuged (at 4° C., 10,000 g, for 5 min) and supernatants were removed. To the resultant pellets was gently added 20 μl of PBS, the mixture was centrifuged (4° C., 10,000 g, 5 min), and supernatants were removed. To the resultant pellets was added 10 μl of PBS to form a suspension. To the above suspension was also added 10 μl of 2×sample buffer and the mixture was boiled for 5 min. The resulting mixture was applied to SDS-PAGE (10% acrylamide gel). After the electrophoresis, samples were electroblotted (60 min, 2 mA/cm²) onto a PVDF membrane (ATTO). After the blotting, blocking was done by dipping this PVDF membrane into TBS-T solution (0.1% Tween 20-containing TBS) containing 5% skim milk for 1 hr. Next, this blocked PVDF membrane was washed with TBS-T for 5 min, and then dipped into a TBS-T solution containing anti-mouse Ig antibody solution (Anti-Mouse Ig HRP-Linked Whole Ab, Amersham Biosciences) and 0.1% BSA for 1 hr. Thereafter, 5 min washing with TBS-T was repeated 3 times and mouse IgG was then detected with ECL PLUS western blotting detection reagents kit (Amersham Biosciences) (FIG. 2). It has been disclosed that mouse IgG is present in inactivated HVJ envelope pellets receiving the above treatment. ZZ-NP used increased the amounts of incorporated antibodies in a dose-dependent manner (lane 4: 0.8 μg, lane 5: 4 μg, lane 6: 20 μg).

Example 7

Preparation of Anti-NPC (Nuclear Pore Complex) Antibody-Containing Inactivated HVJ Envelope To 10 μl of a 25HAU/μl inactivated HVJ envelope (GenomONE™, Ishihara Sangyo Kaisha, Ltd., Japan) suspension was added 10 μl of 2 mg/ml ZZ-NP solution and the resultant solution was mixed. To the mixture was added 2 μl of 2% Triton X-100 solution, and centrifuged immediately (at 4° C., 10,000 g, for 5 min) to remove supernatants. The resultant pellets were suspended in 10 μl of 1 mg/ml Anti-NPC antibody (SIGMA) solution. After standing on ice for 5 min, the mixture was centrifuged (4° C., 10,000 g, 5 min) and supernatants were removed. To the resulting Anti-NPC (Nuclear Pore Complex) antibody-containing inactivated HVJ envelope was added 11.25 μl of PBS, and next 1.25 μl of 10 mg/ml protamine sulfate solution, to form a suspension.

Example 8

Figure 3:
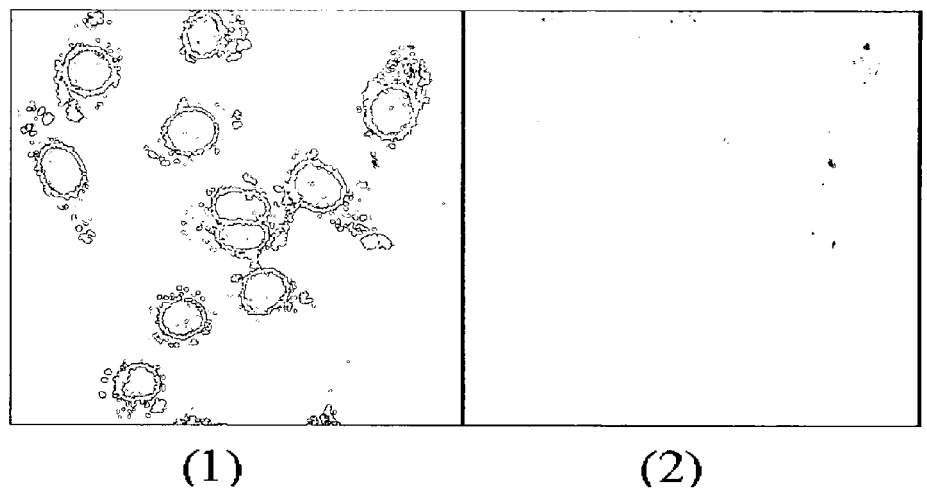
FIG. 3 shows photos for Anti-NPC (Nuclear Pore Complex) antibody, incorporated into HeLa S3 cell with inactivated HVJ envelope and, stained with Alexa 488-labeled goat Anti-Mouse IgG F(ab')$_2$ fragment. Fluorescence image (1). Bright-field image (2).

Inactivated HVJ Envelope-Mediated Introduction of Anti-NPC Antibodies into Cultured Cells HeLa S3 cells (furnished by courtesy of Professor Kaneda, Osaka University, Japan) were seeded at 1×10⁴ cells/0.7 cm², and incubated in a carbon dioxide gas incubator overnight. To the resulting cultured cells was added 5 μl of Anti-NPC antibody-containing inactivated HVJ envelope suspension, obtained in the above Example 7, and the cells were placed in a carbon dioxide gas incubator. Four hours later, the cells were washed twice with PBS, and fixed by treatment with a PBS solution containing 4% paraformaldehyde for 15 min. Next, the cells were washed twice with PBS, and then perfused in a PBS solution containing 0.2% Triton X-100 for 5 min. After the treatment, the cells were washed twice with PBS for 5 min, and then treated with a PBS solution containing 1% BSA for 10 min. Next, the cells were allowed to stand in a PBS solution containing 1% BSA and 4 μg/ml Alexa Fluor 488-labeled Goat Anti-Mouse IgG, F(ab')₂ fragment (Invitrogen) for 1 hr. After washing 3 times with PBS for 5 min at the final step, the cells were observed using confocal laser microscope FV300 (OLYMPUS, Japan) equipped with an Argon laser (FIG. 3). In cytoplasms transfected with Anti-NPC antibody-containing inactivated HVJ envelopes, nuclear membranes were discriminated with labeled secondary antibodies [FIG. 3 (1)]. It has been disclosed that Anti- NPC antibodies incorporated into cells retain the property of recognizing nucleic membranes.

Example 9

Preparation of Plasmid for Expressing Fusion Protein Composed of ZZ Protein and partly deficient Nucleocapsid Protein Nucleocapsid-encoding DNA of pETZZNP, obtained in the above Example 3, was partly deleted to construct pET-ZZK1 to 4.
(1) Construction of pET-ZZK1, pET-ZZK2 and pET-ZZK3
PCR was performed using as a template pET-ZZNP and each primer set, primer 6 (5'-TAGCTCGAGCACCACCAC-3'; SEQ ID NO: 20) in combination with primer 7 (5'-GTTTGCCAGATGATGTCT-3'; SEQ ID NO: 21); primer 6 (5'-TAGCTCGAGCACCACCAC-3'; SEQ ID NO: 20) in combination with primer 8 (5'-AAGGTATGTCCTCCCTGT-3'; SEQ ID NO: 22); and primer 6 (5'-TAGCTCGAGCAC-CACCAC-3'; SEQ ID NO: 20) in combination with primer 9 (5'-AACTATCTGGATGTTCTT-3'; SEQ ID NO: 23), respectively. The PCR was done using Pyrobest™ DNA Polymerase (Takara), in 50 µl of reaction solution (a reaction buffer attached to Pyrobest™ DNA Polymerase, 200 µM each of dATP, dTTP, dCTP and dGTP, and 400 nM each of said primers) admixed with about 1 ng of pETZZNP. The amplification was performed using GeneAmp PCR system 9700 (PE Applied Biosystems) set to repeat steps at 98° C. for 10 sec, at 60° C. for 30 sec and at 72° C. for 7 min, for a total of 30 cycles. The resultant DNA fragments were subjected to self-ligation to form pET-ZZK1, pET-ZZK2 and pET-ZZK3.
(2) Construction of pET-ZZK4
PCR was performed using as a template pET-ZZK1 in combination with primers, primer 10 (5'-CGGATC-CCCGGGTACCGAGCTCGAATT-3'; SEQ ID NO: 24) and primer 11 (5'-GGGAACTACATCCGAGATGCAG-3'; SEQ ID NO: 25) in the same fashion as in the above (1) to create pET-ZZK4.

Example 10

Preparation of Fusion Proteins (ZZ-NPK1, ZZ-NPK2, ZZ-NPK3 and ZZ-NPK4) Composed of ZZ Protein and Partly Deficient Nucleocapsid Protein Fusion proteins ZZ-NPK1, ZZ-NPK2, ZZ-NPK3, and ZZ-NPK4 were inducibly expressed in *E. coli* using T7 expression system. Specifically, *E. coli* Rosetta (DE3) (Novagen) was transformed with pET-ZZK1, pET-ZZK2, pET-ZZK3, and pET-ZZK4, respectively, obtained in the above Example 9, and the resulting transformants (transformed cells) were incubated in LB culture medium (30 ml) containing kanamycin (final concentration: 20 µg/ml) and chloramphenicol (final concentration: 34 µg/ml) at 37° C. overnight. Each of the resultant cultures was used as a preculture solution. This preculture solution was transferred in 1 L of LB culture medium containing kanamycin (final concentration: 20 µg/ml) and chloramphenicol (final concentration: 34 µg/ml), and incubated. When the culture was grown to $OD_{600}$=0.6, expression was induced by adding 1 ml of 1M IPTG solution. After further incubation at 37° C. for 4 hr, the culture was centrifuged (at 4° C., 6,000 rpm for 15 min), and cells were collected and stored overnight at -20° C. The resultant cells were suspended in 20 ml of TST solution (50 mM Tris, pH7.6, 150 mM NaCl, 0.05% Tween 20) and then disrupted by sonication. The crude extract was centrifuged (at 4° C., 20,000 g for 30 min), and the resulting supernatant was subjected to affinity purification using IgG Sepharose™ 6 Fast Flow (Amersham Biosciences) according to attached manuals. Briefly, the column was equilibrated with 0.5M acetic acid (pH3.4), TST (50 mM Tris buffer, pH7.6, 150 mM NaCl, 0.05% Tween 20) and loaded with the above supernatant. The column was washed with TST, 5 mM $NH_4Ac$ (pH5.0), and then eluted with 0.5M acetic acid (pH3.4) to obtain target products. The fusion protein containing eluate (2 ml) was dialyzed against 300 mL of PBS for 2 hr, and further against 300 ml of PBS overnight, with dialysis membrane, Spectra/Por Membrane MWCO: 1,000 (Spectrum). After the dialysis, the resulting fusion protein solution (2 ml) was sterilized by filtration through a 0.22 µm filter to give target fusion protein, ZZ-NPK1, ZZ-NPK2, ZZ-NPK3, or ZZ-NPK4. For each sequence of partly deleted nucleocapsid protein products, obtained in this experiment, NPK1 is shown in SEQ ID NO: 26 and 27, NPK2 in SEQ ID NO: 28 and 29, NPK3 in SEQ ID NO: 30 and 31, NPK4 in SEQ ID NO: 32 and 33, respectively.

Example 11

Figure 4:
FIG. 4 shows Western blotting patterns for mouse IgG antibody-containing inactivated HVJ envelopes. Mouse IgG antibodies incorporated into inactivated HVJ envelopes (lane 1, 2). Mouse IgG antibodies incorporated into inactivated HVJ envelopes containing the proteins of the present invention (ZZ-NP: lane 3, 4; ZZ-NPK1: lane 5, 6; ZZ-NPK2: lane 7, 8, ZZ-NPK3: lane 9, 10; ZZ-NPK4: lane 11, 12). Lane 13 to 17: Mouse IgG Ab alone (1/16 µg, ⅛ µg, ¼ µg, ½ µg, and 1 µg, respectively).

Fusion Protein (ZZ-NPK1, ZZ-NPK2, ZZ-NPK3, ZZ-NPK4 or ZZ-NP)-Mediated Preparation of Mouse IgG-Containing Inactivated HVJ Envelope To 10 µl of a 25HAU/µl inactivated HVJ envelope (GenomONE™, Ishihara Sangyo Kaisha, Ltd., Japan) suspension was added 10 µl of ZZ-NPK1, ZZ-NPK2, ZZ-NPK3, ZZ-NPK4 (all obtained in Example 10) or ZZ-NP (obtained in Example 4) solution (adjusted to 1 mg/ml) and the resultant solution was mixed. Next, to the mixture was added 2 µl of 2% Triton X-100 solution, and centrifuged immediately (at 4° C., 10,000 g, for 5 min) to remove supernatants. The resulting respective ZZ fusion protein-containing inactivated HVJ envelope was suspended in 10 µl of antibody solution (1 mg/ml Mouse IgG (SIGMA), PBS) and then allowed to stand on ice for 5 min. The suspension was centrifuged (at 4° C., 10,000 g, for 5 min) and supernatants were removed. To the resultant pellets was gently added 10 µl of PBS, the mixture was recentrifuged (4° C., 10,000 g, 5 min), and supernatants were removed. To the resultant pellets was added 10 µl of PBS to form a suspension. To the above suspension was also added 10 µl of 2×sample buffer and the mixture was boiled for 5 min. The resulting mixture was applied to SDS-PAGE (10% acrylamide gel). After the electrophoresis, samples were electroblotted (60 min, 2 mA/cm²) onto a PVDF membrane (ATTO). After the blotting, blocking was done by dipping this PVDF membrane into TBS-T solution (0.1% Tween 20-containing TBS) containing 5% skim milk for 1 hr. Next, this blocked PVDF membrane was washed with TBS-T for 5 min, and then dipped into a TBS-T solution containing Peroxidase-conjugated AffiniPure $F(ab')_2$ Fragment Goat Anti-Mouse IgG (H+L) (Jackson Immuno Research Laboratories) and 0.1% BSA for 1 hr. Thereafter, 5 min washing with a TBS-T solution was repeated 3 times and mouse IgG was then detected with ECL PLUS western blotting detection reagents kit (Amersham Biosciences) (FIG. 4). It has been disclosed that mouse IgG is present in inactivated HVJ envelope pellets receiving the above treatments with fusion proteins. Among fusion proteins used, the highest incorporation level of mouse IgG into the inactivated HVJ envelope was observed when ZZ-NPK1 was used.

Example 12

Preparation of Anti-NPC (Nuclear Pore Complex) Antibody-Containing Inactivated HVJ Envelope To 5 µl of a 25HAU/µl inactivated HVJ envelope (GenomONE™, Ishihara Sangyo Kaisha, Ltd., Japan) suspension was added 5 µl of 0.5 mg/ml ZZ-NPK1 solution and the resultant solution was mixed. To the mixture was added 1 µl of 2% Triton X-100 solution, and centrifuged immediately (at 4° C., 10,000 g, for 5 min) to remove supernatants. The resultant pellets were suspended in 5 µl of 0.25 mg/ml Anti-NPC antibody (SIGMA) solution. After standing on ice for 5 min, the mixture was centrifuged (4° C., 10,000 g, 5 min) and supernatants were removed. To the resulting Anti-NPC (Nuclear Pore Complex) antibody (Ab)-containing inactivated HVJ envelope was added 6.25 µl of PBS, and next 6.25 µl of 1 mg/ml protamine sulfate solution, to form a suspension.

Example 13

Inactivated HVJ Envelope-Mediated Introduction of Anti-NPC Ab into Cultured Cells HeLa S3 cells (furnished by courtesy of Professor Kaneda, Osaka University, Japan) were seeded at $1 \times 10^4$ cells/0.7 cm$^2$, and incubated in a carbon dioxide gas incubator overnight. To the resulting cultured cells was added 10 µl of Anti-NPC Ab-containing inactivated HVJ envelope suspension, obtained in the above Example 12, and the mixture was placed in a carbon dioxide gas incubator. Four hours later, the cells were washed twice with PBS, and fixed by treatment with a PBS solution containing 4% paraformaldehyde for 15 min. Next, the cells were washed twice with PBS, and then perfused in a PBS solution containing 0.2% Triton X-100 for 5 min. After the treatment, the cells were washed twice with PBS for 5 min, and then treated with a PBS solution containing 1% BSA for 10 min. Next, the cells were allowed to stand in a PBS solution containing 1% BSA and 4 µg/ml Alexa Fluor 488-labeled Goat Anti-Mouse IgG, F(ab')$_2$ fragment (Invitrogen) for 1 hr. After washing 3 times with PBS for 5 min at the final step, the cells were analyzed using confocal laser microscope FV300 (OLYMPUS, Japan) equipped with an Argon laser. For controls, the same treatments were repeated using a solution containing Anti-NPC Ab alone in place of the above-described Anti-NPC Ab-containing inactivated HVJ envelope suspension.

Figure 5:
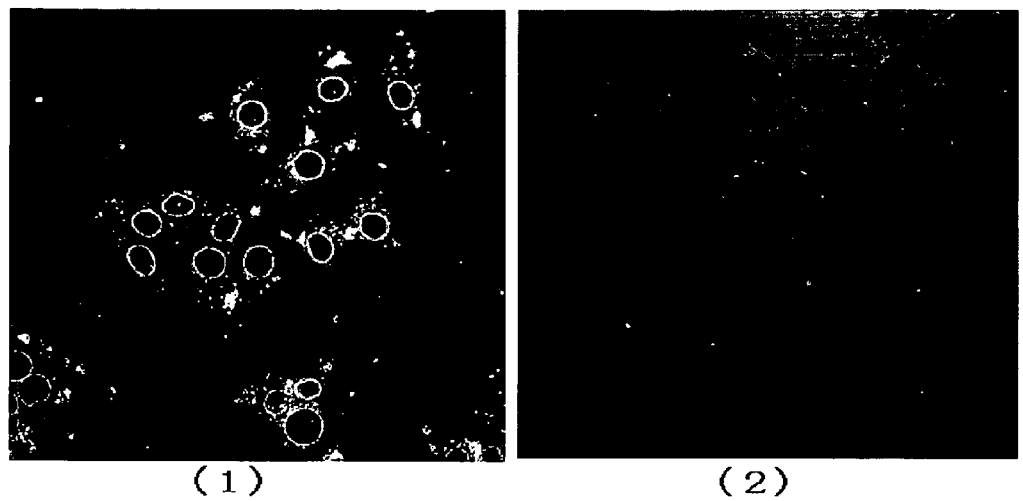
FIG. 5 shows photos for Anti-NPC (Nuclear Pore Complex) Ab, incorporated into HeLa S3 cell with inactivated HVJ envelope and, stained with Alexa 488-labeled goat Anti-Mouse IgG F(ab')$_2$ fragment. Cells receiving introduction of Anti-NPC Ab with ZZ-NPK1-containing inactivated HVJ envelopes (1). Cells receiving introduction with Anti-NPC Ab alone (2).
Figure 6:
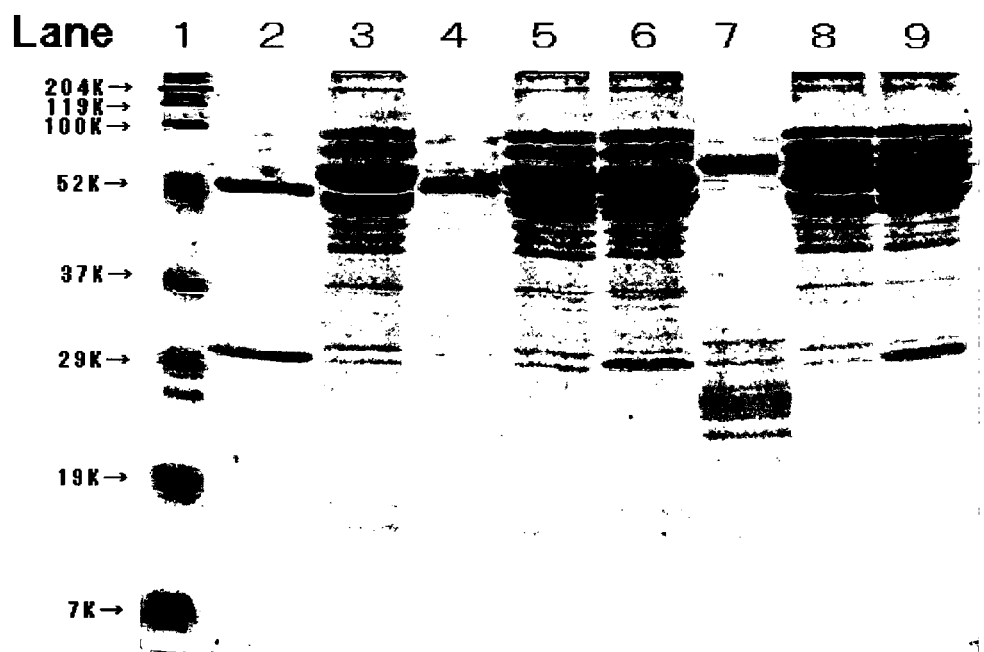
FIG. 6 shows SDS-PAGE patterns for inactivated HVJ envelopes within which G-NPK1 or GG-NPK1 made Rat IgG2b Ab be enclosed. Rat IgG2b Ab incorporated into inactivated HVJ envelopes containing the proteins of the present invention (G-NPK1: 6, GG-NPK1: 9). Molecular markers (lane 1). Rat IgG2b Ab alone (lane 2). Inactivated HVJ envelope alone (lane 3). G-NPK1 alone (lane 4). GG-NPK1 alone (lane 7). Inactivated HVJ envelopes containing the proteins of the present invention (G-NPK1: lane 5, GG-NPK1: lane 8).
Figure 7:
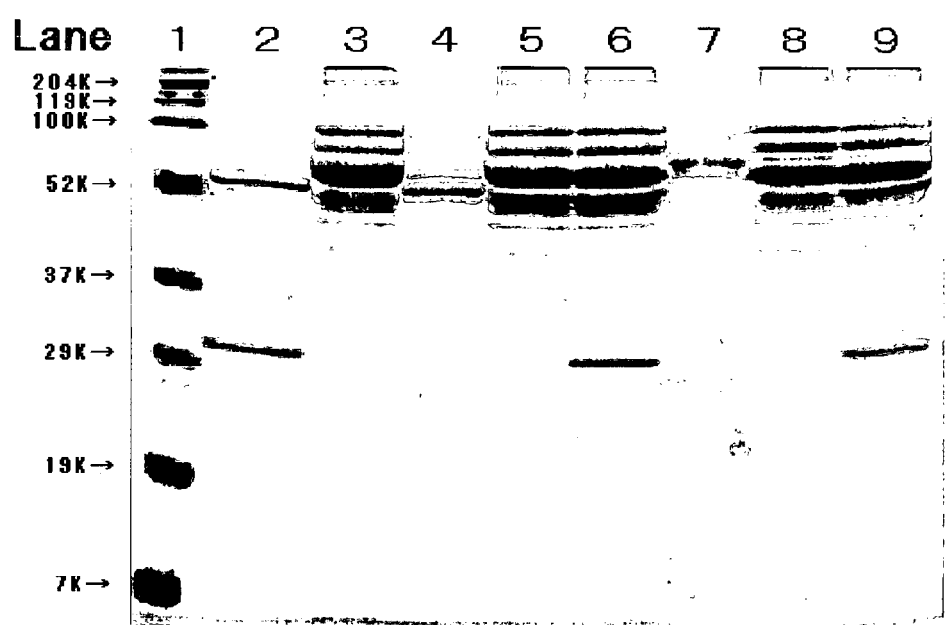
FIG. 7 shows SDS-PAGE patterns for inactivated HVJ envelopes within which L-NPK1 or LL-NPK1 made Rat IgG2b Ab be enclosed. Rat IgG2b Ab incorporated into inactivated HVJ envelopes containing the proteins of the present invention (L-NPK1: 6, LL-NPK1: 9). Molecular markers (lane 1). Rat IgG2b Ab alone (lane 2). Inactivated HVJ envelope alone (lane 3). L-NPK1 alone (lane 4). LL-NPK1 alone (lane 7). Inactivated HVJ envelopes containing the proteins of the present invention (L-NPK1: lane 5, LL-NPK1: lane 8).

While no incorporation of antibodies into cells was observed in case of Anti-NPC Ab alone, nuclear membranes were discriminated with labeled secondary antibodies in cells Anti-NPC Ab-transfected with ZZ-NPK1-containing inactivated HVJ envelopes (FIG. 5).

Example 14

Construction of Plasmids for Expressing Fusion Proteins Composed of Protein G C1 Region or its Tandem Repeat Dimer Protein and Partly Deficient Nucleocapsid Protein (NPK1)

PCR was performed using as a template pET28a (Novagen) in combination with primers, primer 12 (5'-GAAGCGGTTGATGCTGCTACCGCA-GAAAAAGTTTTCAAACAGTA CGCTAACAGCAT-GACTGGTGGACAG-3': SEQ ID NO: 34) and primer 13 (5'-AGTAGTGGTTTCGCCTTTCAAGGTTT-TACCATTCAGGATTAATT TGTAGGTCATGG-TATATCTCCTTCT-3': SEQ ID NO: 35). The PCR was done using Pyrobest DNA Polymerase (Takara), in 50 µl of reaction solution (a reaction buffer attached to Pyrobest DNA Polymerase, 200 µl each of dATP, dTTP, dCTP and dGTP, and 400 nM each of said primers) admixed with about 1 ng of template plasmid. The amplification was performed using GeneAmp PCR system 9700 (PE Applied Biosystems) set to repeat steps at 98° C. for 10 sec, at 58° C. for 30 sec and at 72° C. for 6 min, for a total of 30 cycles. The resultant DNA fragment was subjected to self-ligation to form pETG1 coding for an half (N-terminal side) of the Protein G C1 region.

Further, PCR was performed using as a template pETG1, in combination with primers, primer 14 (5'-GTTACT-GAAAAACCGGAAGTGATCGATGCGTCT-GAATTAACCCC GGCGGTGACCCTGAGATCCGGCT-GCTAA-3': SEQ ID NO: 36) and primer 15 (5'-GGTAAAGGTTTTAGTCGCATCGTCGTAGGTCCATTC ACCGTCAA CACCGTTGTCGTTAGCGTACT-GTTTGAA-3'; SEQ ID NO: 37). The PCR was done in the same fashion as above, followed by self-ligation, to obtain pETG2 coding for the full length Protein G C1 region.

Next, PCR was performed using as a template pETG2, in combination with primers, primer 16 (5'-ATGCGTCCG-GCGTAGA-3'; SEQ ID NO: 38) and primer 17 (5'-TAG-CAGTTGGAATTCGCGGTCACCGCCGGGGTTAA-3'; SEQ ID NO: 39).

The PCR was done using Ex Taq (Takara), in 50 µl of reaction solution (a reaction buffer attached to Ex Taq (Takara), 200 µM each of dATP, dTTP, dCTP and dGTP, and 400 nM each of said primers) admixed with about 1 ng of template plasmid. The amplification was performed using GeneAmp PCR system 9700 (PE Applied Biosystems) set to repeat steps at 94° C. for 30 sec, at 58° C. for 30 sec and at 72° C. for 1 min, for a total of 30 cycles. The resultant DNA fragment was digested with restriction enzymes, Xba I and EcoR I, and then inserted into the site derived by cleavage with Xba I and EcoR I from pET-ZZNPK1 to create plasmid pET-GNPK1 for expressing a fusion protein composed of Protein G C1 region and NPK1.

PCR was performed using as a template pETG2 in combination with primers, primer 18 (5'-AGGAGATAGAATTC-TACCTACAAATTAATCCTGAA-3'; SEQ ID NO: 40) and primer 17 (5'-AAGGTATGTCCTCCCTGT-3'; SEQ ID NO: 39). The PCR was done in the same fashion as above. The resultant DNA fragment was digested with restriction enzyme, EcoR I, and then inserted into the site derived by cleavage with EcoR I from pET-GNPK1 to create plasmid pET-GGNPK1 for expressing a fusion protein composed of the tandem repeat dimer of Protein G C1 region and NPK1.

Example 15

Construction of Plasmids for Expressing Fusion Proteins Composed of Protein L B1 Region or its Tandem Repeat Dimer Protein and Partly Deficient Nucleocapsid Protein (NPK1)

PCR was performed using as a template pET28a (Novagen) in combination with primers, primer 19 (5'-AAC-CTGATCTTTGCGAACGGCAGCACCCA-GACCGCGGAATTTAAA GGCACCTTTGAAAAAAG-CATGACTGGTGGACAG-3'; SEQ ID NO: 41) and primer 20 (5'-CGCTTTGATGGTCACTTCTTCTTCGC-TATCGGTTTCCGGGGTTTC CGGGGTTTCT-TCTTTCATGGTATATCTCCTTCT-3'; SEQ ID NO: 42). The PCR was done using Pyrobest DNA Polymerase (Takara), in 50 µl of reaction solution (a reaction buffer attached to Pyrobest DNA Polymerase, 200 μM each of dATP, dTTP, dCTP and dGTP, and 400 nM each of said primers) admixed with about 1 ng of template plasmid. The amplification was performed using GeneAmp PCR system 9700 (PE Applied Biosystems) set to repeat steps at 98° C. for 10 sec, at 58° C. for 30 sec and at 72° C. for 6 min, for a total of 30 cycles. The resultant DNA fragment was subjected to self-ligation to form pETL1 coding for an half (N-terminal side) of the Protein L B1 region.

Next, PCR was performed using as a template pETL1 in combination with primers, primer 21 (5'-TGAATATAC-CGTGGATGTGGCGGATAAAGGTTATACCCTGAA CATTAAATTTGCGGGTTTTTTGCTGAAAGGA-3'; SEQ ID NO: 43) and primer 22 (5'-CCGT-TATCTTTTTTCAGGGTATCCGCATACG-CATACGCTTCGC TGGTCGCTTTTTCAAAGGTACCTT-TAA-3'; SEQ ID NO: 44). The PCR was done in the same fashion as above, followed by self-ligation, to obtain pETL2 coding for the full length Protein L B1 region.

Further, PCR was performed using as a template pETL2, in combination with primers, primer 23 (5'-ATGCGTCCG-GCGTAGA-3'; SEQ ID NO: 45) and primer 24 (5'-TCCCCT-GTCGAATTCGCACCCGCAAATTTAATGT-3'; SEQ ID NO: 46).
The PCR was done using Ex Taq (Takara), in 50 μl of reaction solution (a reaction buffer attached to Ex Taq (Takara), 200 μm each of dATP, dTTP, dCTP and dGTP, and 400 nM each of said primers) admixed with about 1 ng of template plasmid. The amplification was performed using GeneAmp PCR system 9700 (PE Applied Biosystems) set to repeat steps at 94° C. for 30 sec, at 58° C. for 30 sec and at 72° C. for 1 min, for a total of 30 cycles. The resultant DNA fragment was digested with restriction enzymes, Xba I and EcoR I, and then inserted into the site derived by cleavage with Xba I and EcoR I from pET-ZZNPK1 to create plasmid pET-LNPK1 for expressing a fusion protein composed of Protein L B1 region and NPK1.

PCR was also performed using as a template pETL2 in combination with primers, primer 25 (5'-AGGAGATA-GAATTCTAAAGAAGAAACCCCGGAAAC-3'; SEQ ID NO: 47) and primer 24 (5'-AAGGTATGTCCTCCCTGT-3'; SEQ ID NO: 46). The PCR was done in the same fashion as above. The resultant DNA fragment was digested with restriction enzyme, EcoR I, and then inserted into the site derived by cleavage with EcoR I from pET-LNPK1 to create plasmid pET-LLNPK1 for expressing a fusion protein composed of the tandem repeat dimer of Protein L B1 region and NPK1.

Example 16

Figure 8:
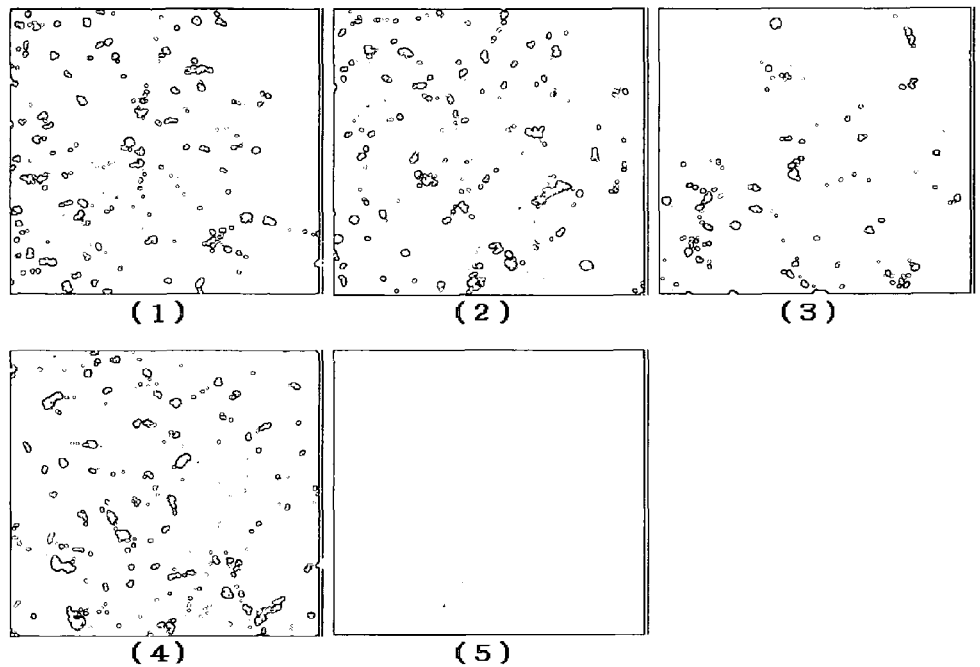
FIG. 8 show photos for Rat IgG2b Ab, incorporated into HeLa S3 cells with inactivated HVJ envelope and, stained with Alexa 488-labeled chicken anti-Rat IgG Ab. Cells receiving introduction of Rat IgG2b Ab with inactivated HVJ envelopes containing the proteins of the present invention [G-NPK1: (1), GG-NPK1: (2), L-NPK1: (3), LL-NPK1: (4)]. Cells receiving introduction with rat IgG2b Ab alone (5).

Preparation of Fusion Proteins G-NPK1, GG-NPK1, L-NPK1 and LL-NPK1 Composed of Protein G C1 Region, or Protein L B1 Region, and Partly Deficient Nucleocapsid Protein Fusion proteins G-NPK1, GG-NPK1, L-NPK1 and LL-NPK1 were inducibly expressed in *E. coli* expression systems utilizing T7 RNA polymerase. *E. coli* Rosetta (DE3) (Novagen) was transformed with pET-GNPK1 and pET-GGNPK1, obtained in the above Example 14, and pET-LNPK1 and pET-LLNPK1, obtained in the above Example 15, and treated in the same fashion as in Example 10 to give target fusion proteins G-NPK1, GG-NPK1, L-NPK1 and LL-NPK1, respectively, provided that, for eluents upon the affinity purification of G-NPK1 and GG-NPK1, 0.1M glycine-HCl (pH2.7) was used in place of 0.5M acetic acid (pH3.4).

Example 17

Fusion Protein G-NPK1, GG-NPK1, L-NPK1 or LL-NPK1-Mediated Preparation of Rat IgG2b-Containing Inactivated HVJ Envelope To 10 μl of a 25HAU/μl inactivated HVJ envelope (GenomONE™, Ishihara Sangyo Kaisha, Ltd., Japan) suspension was added 10 μl of G-NPK1, GG-NPK1, L-NPK1 or LL-NPK1 (all obtained in Example 16) solution (adjusted to ½ mg/ml) and the resultant solution was mixed. Next, to the mixture was added 2 μl of 2% Triton X-100 solution, and centrifuged immediately (at 4° C., 10,000 g, for 5 min) to remove supernatants. The resulting G-NPK1, GG-NPK1, L-NPK1 or LL-NPK1-containing inactivated HVJ envelopes were suspended in 5 μl of antibody solution (1 mg/ml Rat IgG2b (R&D systems)) and then allowed to stand on ice for 5 min. The suspension was centrifuged (at 4° C., 10,000 g, for 5 min) and supernatants were removed. To the resultant pellets was gently added 20 μl of PBS, the mixture was recentrifuged (4° C., 10,000 g, 5 min), and supernatants were removed. To the resultant pellets was added 10 μl of PBS to form a suspension. To the above suspension was also added 10 μl of 2×sample buffer and the mixture was boiled for 5 min. The resulting mixture was applied to SDS-PAGE (10% acrylamide gel), and CBB staining was done after the electrophoresis (FIGS. 6 and 7). It has been disclosed that rat IgG2b is present in inactivated HVJ envelope pellets receiving the above treatment.

Example 18

Preparation of Rat IgG2b-Containing Inactivated HVJ Envelope

To 10 μl of a 25HAU/μl inactivated HVJ envelope (GenomONE™, Ishihara Sangyo Kaisha, Ltd., Japan) suspension was added 10 μl of G-NPK1, GG-NPK1, L-NPK1 or LL-NPK1 (all obtained in Example 16) solution (adjusted to ½ mg/ml) and the resultant solution was mixed. To the mixture was added 2 μl of 2% Triton X-100 solution, and centrifuged immediately (at 4° C., 10,000 g, for 5 min) to remove supernatants. The resultant G-NPK1, GG-NPK1, L-NPK1 or LL-NPK1-containing inactivated HVJ envelopes were suspended in 5 μl of antibody solution (rat IgG2b (R&D systems), 1 mg/ml).

After standing on ice for 5 min, the mixture was centrifuged (4° C., 10,000 g, 5 min) and supernatants were removed. To the resulting rat IgG2b-containing inactivated HVJ envelopes was added 12.5 μl of PBS, and further 12.5 μl of 1 mg/ml protamine sulfate solution to form a suspension.

Example 19

Inactivated HVJ Envelope-Mediated Introduction of Rat IgG2b into Cultured Cells HeLa S3 cells (furnished by courtesy of Professor Kaneda, Osaka University, Japan) were seeded at $1\times10^4$ cells/0.7 $cm^2$, and incubated in a carbon dioxide gas incubator (5% $CO_2$, 37° C.) overnight. To the resulting cultured cells was added 10 μl of rat IgG2b-containing inactivated HVJ envelope suspension, obtained in the above Example 18, and the mixture was placed in a carbon dioxide gas incubator. Four hours later, the cells were washed twice with PBS, and fixed by treatment with a PBS solution containing 4% paraformaldehyde for 15 min. Next, the cells were washed twice with PBS, and then perfused in a PBS solution containing 0.2% Triton X-100 for 5 min. After the treatment, the cells were washed twice with PBS for 5 min, and then treated with a PBS solution containing 1% BSA for 10 min. Next, the cells were allowed to stand in a PBS solution containing 1% BSA and 4 µg/ml Alexa Fluor 488-labeled chicken Anti-rat IgG (Invitrogen) for 1 hr at room temperature. After washing 3 times with PBS for 5 min at the final step, the cells were analyzed using confocal laser microscope FV300 (OLYMPUS, Japan) equipped with an Argon laser (FIG. 8). It has been verified that rat IgG2b antibodies are present homogeneously within cytoplasms transfected with rat IgG2b Ab-containing inactivated HVJ envelopes.

Example 20

Fusion Protein G-NPK1, GG-NPK1, L-NPK1 or LL-NPK1-Mediated Preparation of Anti-NPC (Nuclear Pore Complex) Antibody-Containing Inactivated HVJ Envelope To 10 µl of a 25HAU/µl inactivated HVJ envelope (GenomONE™, Ishihara Sangyo Kaisha, Ltd., Japan) suspension was added 10 µl of G-NPK1, GG-NPK1, L-NPK1 or LL-NPK1 (all obtained in Example 16) solution (adjusted to ½ mg/ml) and the resultant solution was mixed. Next, to the mixture was added 2 µl of 2% Triton X-100 solution, and centrifuged immediately (at 4° C., 10,000 g, for 5 min) to remove supernatants. The resulting G-NPK1, GG-NPK1, L-NPK1 or LL-NPK1-containing inactivated HVJ envelopes were suspended in 5 µl of antibody solution (Anti-NPC Ab, 1 mg/ml). After standing on ice for 5 min, the suspension was centrifuged (4° C., 10,000 g, 5 min) and supernatants were removed. To the resulting Anti-NPC Ab-containing inactivated HVJ envelopes was added 12.5 µl of PBS, and further 12.5 µl of 1 mg/ml protamine sulfate solution to form a suspension.

Example 21

Figure 9:
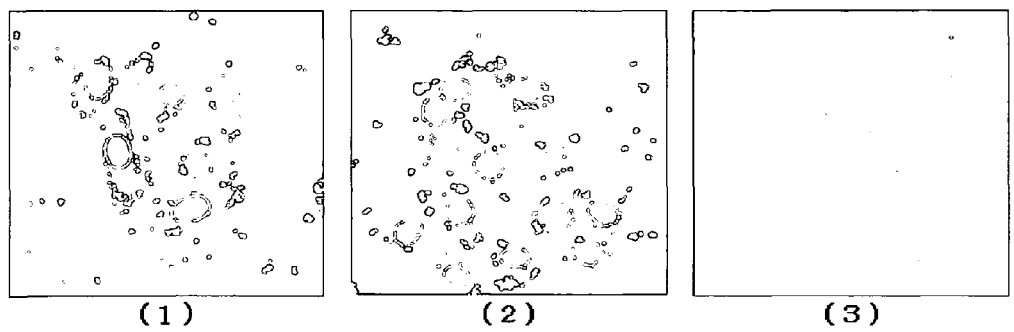
FIG. 9 shows the detection, with Alexa 488-labeled goat anti-mouse IgG F(ab')$_2$ fragments, of anti-NPC (Nuclear Pore Complex) antibodies introduced into HeLa S3 cells with inactivated HVJ envelopes. Cells treated by G-NPK1- or GG-NPK1-containing inactivated HVJ envelope-mediated introduction of anti-NPC Ab [(1): G-NPK1, (2): GG-NPK1]. (3): Cells treated by introduction of anti-NPC Ab alone.

Inactivated HVJ Envelope-Mediated Introduction of Anti-NPC Antibodies into Cultured Cells Tests for introducing Anti-NPC (Nuclear Pore Complex) Ab into cultured cells were conducted using Anti-NPC Ab-containing inactivated HVJ envelopes, obtained in Example 20, in the same manner as in Example 13. In cytoplasms transfected with Anti-NPC Ab-containing inactivated HVJ envelopes, nuclear membranes were discriminated with labeled secondary antibodies [FIG. 9(1) and (2)]. It has been disclosed that Anti-NPC antibodies incorporated into cells retain the property of recognizing nucleic membranes.

INDUSTRIAL APPLICABILITY

In accordance with the present invention, use of proteins containing a envelope viral component-compatible polypeptide, and envelope viruses or inactivated envelope viruses in combination with said proteins, enables proteins, antibodies, and other foreign substances (non-self substances) to be incorporated into one or more cells without damaging their properties, functions and structures, and such intracellular delivery techniques are time and quantity controllable and facilitate efficient introduction of foreign substances into cells. The present invention provides targeting techniques for a wide variety of cells including various adhesive and suspension cells and primarily cultured cells and applicable to animals (in vivo), as well as techniques which can adapt, combinations of molecules to be intracellularly introduced with targets thereof, toward diverse applications.

Thus, applications of the present invention facilitate in vivo and in vitro function analysis in unknown genes, in vivo and in vitro function analysis in targetted genes, all aspects of gene therapy including clinical studies and clinical trials, studies to evaluate the onset mechanisms of diseases and to prevent the disease onset, DDS (Drug Delivery System) studies and uses, function examinations of novel useful materials and new drug candidates and application studies thereof, and applications to Drug Discovery. In more specific embodiments, the present invention allows the development and research of antineoplastic actions, cytotoxic actions and control actions such as gene expression.

While the present invention has been described specifically in detail with reference to certain embodiments and examples thereof, it would be apparent that it is possible to practice it in other forms. In light of the disclosure, it will be understood that various modifications and variations are within the spirit and scope of the appended claims.

<Sequence Listing Free Text>
SEQ ID NO:3, Modified antigen binding amino acid sequence derived from B domain of Protein A (*Staphylococcus aureus*)
SEQ ID NO:4, Modified antigen binding amino acid sequence derived from B domain of Protein A (*Staphylococcus aureus*)
SEQ ID NO:5, Fusion protein includes antibody binding amino acid sequence and Sendai virus nucleocapsid protein (ZZ-NP)
SEQ ID NO:6, Fusion protein includes antibody binding amino acid sequence and Sendai virus nucleocapsid protein (ZZ-NP)
SEQ ID NO:7, Oligonucleotide to act as a primer for PCR
SEQ ID NO:8, Oligonucleotide to act as a primer for PCR
SEQ ID NO:9, Oligonucleotide to act as a primer for reverse transcription
SEQ ID NO:10, Oligonucleotide to act as a primer for PCR
SEQ ID NO:11, Oligonucleotide to act as a primer for PCR
SEQ ID NO:12, Fusion protein includes antibody binding amino acid sequence and Sendai virus nucleocapsid protein (ZZ-NPK1)
SEQ ID NO:13, Fusion protein includes antibody binding amino acid sequence and Sendai virus nucleocapsid protein (ZZ-NPK1)
SEQ ID NO:14, Fusion protein includes antibody binding amino acid sequence and Sendai virus nucleocapsid protein (ZZ-NPK2)
SEQ ID NO:15, Fusion protein includes antibody binding amino acid sequence and Sendai virus nucleocapsid protein (ZZ-NPK2)
SEQ ID NO:16, Fusion protein includes antibody binding amino acid sequence and Sendai virus nucleocapsid protein (ZZ-NPK3)
SEQ ID NO:17, Fusion protein includes antibody binding amino acid sequence and Sendai virus nucleocapsid protein (ZZ-NPK3)
SEQ ID NO:18, Fusion protein includes antibody binding amino acid sequence and Sendai virus nucleocapsid protein (ZZ-NPK4)
SEQ ID NO:19, Fusion protein includes antibody binding amino acid sequence and Sendai virus nucleocapsid protein (ZZ-NPK4)

SEQ ID NO:20, Oligonucleotide to act as a primer for PCR
SEQ ID NO:21, Oligonucleotide to act as a primer for PCR
SEQ ID NO:22, Oligonucleotide to act as a primer for PCR
SEQ ID NO:23, Oligonucleotide to act as a primer for PCR
SEQ ID NO:24, Oligonucleotide to act as a primer for PCR
SEQ ID NO:25, Oligonucleotide to act as a primer for PCR
SEQ ID NO:26, Sendai virus nucleocapsid protein (NPK1)
SEQ ID NO:27, Sendai virus nucleocapsid protein (NPK1)
SEQ ID NO:28, Sendai virus nucleocapsid protein (NPK2)
SEQ ID NO:29, Sendai virus nucleocapsid protein (NPK2)
SEQ ID NO:30, Sendai virus nucleocapsid protein (NPK3)
SEQ ID NO:31, Sendai virus nucleocapsid protein (NPK3)
SEQ ID NO:32, Sendai virus nucleocapsid protein (NPK4)
SEQ ID NO:33, Sendai virus nucleocapsid protein (NPK4)
SEQ ID NO:34, Oligonucleotide to act as a primer for PCR
SEQ ID NO:35, Oligonucleotide to act as a primer for PCR
SEQ ID NO:36, Oligonucleotide to act as a primer for PCR
SEQ ID NO:37, Oligonucleotide to act as a primer for PCR
SEQ ID NO:38, Oligonucleotide to act as a primer for PCR
SEQ ID NO:39, Oligonucleotide to act as a primer for PCR
SEQ ID NO:40, Oligonucleotide to act as a primer for PCR
SEQ ID NO:41, Oligonucleotide to act as a primer for PCR
SEQ ID NO:42, Oligonucleotide to act as a primer for PCR
SEQ ID NO:43, Oligonucleotide to act as a primer for PCR
SEQ ID NO:44, Oligonucleotide to act as a primer for FCR
SEQ ID NO:45, Oligonucleotide to act as a primer for PCR
SEQ ID NO:46, Oligonucleotide to act as a primer for PCR
SEQ ID NO:47, Oligonucleotide to act as a primer for PCR
SEQ ID NO:48, Antigen binding amino acid sequence derived from C1 domain of Protein G (*Streptococcus* G148)
SEQ ID NO:49, Antigen binding amino acid sequence derived from C1 domain of Protein G (*Streptococcus* G148)
SEQ ID NO:50, Antigen binding amino acid sequence derived from B1 domain of Protein L (*Peptostreptococcus magnus*)
SEQ ID NO:51, Antigen binding amino acid sequence derived from B1 domain of Protein L (*Peptostreptococcus magnus*)
SEQ ID NO:52, Fusion protein includes antibody binding amino acid sequence and Sendai virus nucleocapsid protein (G-NPK1)
SEQ ID NO:53, Fusion protein includes antibody binding amino acid sequence and Sendai virus nucleocapsid protein (G-NPK1)
SEQ ID NO:54, Fusion protein includes antibody binding amino acid sequence and Sendai virus nucleocapsid protein (GG-NPK1)
SEQ ID NO:55, Fusion protein includes antibody binding amino acid sequence and Sendai virus nucleocapsid protein (GG-NPK1)
SEQ ID NO:56, Fusion protein includes antibody binding amino acid sequence and Sendai virus nucleocapsid protein (L-NPK1)
SEQ ID NO:57, Fusion protein includes antibody binding amino acid sequence and Sendai virus nucleocapsid protein (L-NPK1)
SEQ ID NO:58, Fusion protein includes antibody binding amino acid sequence and Sendai virus nucleocapsid protein (LL-NPK1)
SEQ ID NO:59, Fusion protein includes antibody binding amino acid sequence and Sendai virus nucleocapsid protein (LL-NPK1)

What is claimed is:

1. A method for introducing one or more foreign substances into a cell with an envelope virus or inactivated envelope virus, which comprises the steps of
   (1) mixing an envelope virus or inactivated envelope virus with a protein comprising (a) a polypeptide having an affinity for one or more envelope viral components in combination with (b) a polypeptide capable of binding to one or more foreign substances to be introduced into a cell,
   (2) subjecting the mixture from the above step (1) to a treatment affecting the permeability of envelopes,
   (3) mixing the product from the above step (2) with one or more foreign substances, and
   (4) contacting the foreign substance-containing envelope virus or inactivated envelope virus from the above step (3) with one or more cells.

2. A method for introducing one or more foreign substances into a cell with an envelope virus or inactivated envelope virus, which comprises the steps of
   (1) mixing one or more foreign substances with a protein to form a complex, said protein comprising (a) a polypeptide having an affinity for one or more envelope viral components in combination with (b) a polypeptide capable of binding to one or more foreign substances to be introduced into a cell,
   (2) mixing the complex from the above step (1) with an envelope virus or inactivated envelope virus,
   (3) subjecting the mixture from the above step (2) to a treatment affecting the permeability of envelopes, and
   (4) contacting the foreign substance-containing envelope virus or inactivated envelope virus from the above step (3) with one or more cells.

3. The process according to claim 1, wherein the protein comprising said polypeptide (a) in combination with the polypeptide (b) is a fusion protein.

4. The process according to claim 1, wherein said foreign substance is an antibody.

5. The process according to claim 1, wherein said polypeptide (a) is a polypeptide having an affinity for one or more components existing in the inner space of an envelope.

6. The process according to claim 1, wherein said polypeptide (a) is
   (1) a polypeptide of an amino acid sequence of SEQ ID NO: 2, or
   (2) a peptide fragment selected from the group consisting of SEQ ID NOs: 27, 29, 31 and 33.

7. The process according to claim 1, wherein said polypeptide (b) is an antibody binding polypeptide.

8. The process according to claim 7, wherein said antibody binding polypeptide is a polypeptide that can bind to an antibody Fc region or kappa (K) light chain.

9. The process according to claim 7, wherein said antibody binding polypeptide is an amino acid sequence selected from the group consisting of SEQ ID NOs: 4, 49 and 51.

10. The process according to claim 2, wherein the protein comprising said polypeptide (a) in combination with the polypeptide (b) is a fusion protein.

11. The process according to claim 2, wherein said foreign substance is an antibody.

12. The process according to claim 2, wherein said polypeptide (a) is a polypeptide having an affinity for one or more components existing in the inner space of an envelope.

13. The process according to claim 2, wherein said polypeptide (a) is
   (1) a polypeptide of an amino acid sequence of SEQ ID NO: 2, or
   (2) a peptide fragment selected from the group consisting of SEQ ID NOs: 27, 29, 31 and 33.

14. The process according to claim 2, wherein said polypeptide (b) is an antibody binding polypeptide.

15. The process according to claim 14, wherein said antibody binding polypeptide is a polypeptide that can bind to an antibody Fc region or kappa (K) light chain.

16. The process according to claim 14, wherein said antibody binding polypeptide is an amino acid sequence selected from the group consisting of SEQ ID NOs: 4, 49 and 51.

* * * * *

SEQUENCE LISTING

```
<160> NUMBER OF SEQ ID NOS: 59

<210> SEQ ID NO 1
<211> LENGTH: 1575
<212> TYPE: DNA
<213> ORGANISM: Sendai virus
<220> FEATURE:
<221> NAME/KEY: CDS
<222> LOCATION: (1)..(1575)
<223> OTHER INFORMATION:

<400> SEQUENCE: 1 atg gcc ggg ttg ttg agc acc ttc gat aca ttt agc tct agg agg agc      48
Met Ala Gly Leu Leu Ser Thr Phe Asp Thr Phe Ser Ser Arg Arg Ser
1               5                   10                  15 gaa agt att aat aag tcg gga gga ggt gct gtt atc ccc ggc cag agg      96
Glu Ser Ile Asn Lys Ser Gly Gly Gly Ala Val Ile Pro Gly Gln Arg
                20                  25                  30 agc aca gtc tca gtg ttc gta cta ggc cca agt gtg act gat gat gca     144
Ser Thr Val Ser Val Phe Val Leu Gly Pro Ser Val Thr Asp Asp Ala
            35                  40                  45 gac aag tta ttc att gca act acc ttc cta gct cac tca ttg gac aca     192
Asp Lys Leu Phe Ile Ala Thr Thr Phe Leu Ala His Ser Leu Asp Thr
        50                  55                  60 gat aag cag cac tct cag aga gga ggg ttc ctc gtc tct ctg ctt gcc     240
Asp Lys Gln His Ser Gln Arg Gly Gly Phe Leu Val Ser Leu Leu Ala
65                  70                  75                  80 atg gct tac agt agt cca gaa ttg tac ttg aca aca aac gga gta aac     288
Met Ala Tyr Ser Ser Pro Glu Leu Tyr Leu Thr Thr Asn Gly Val Asn
                85                  90                  95
```

-continued

| | | |
|---|---|---|
| gcc gat gtc aaa tat gtg atc tac aac ata gag aaa gac cct aag agg<br>Ala Asp Val Lys Tyr Val Ile Tyr Asn Ile Glu Lys Asp Pro Lys Arg<br>100                          105                     110 | | 336 |
| acg aag aca gac gga ttc att gtg aag acg aga gat atg gaa tat gag<br>Thr Lys Thr Asp Gly Phe Ile Val Lys Thr Arg Asp Met Glu Tyr Glu<br>              115                       120                       125 | | 384 |
| agg acc aca gaa tgg ctg ttt gga cct atg gtc aac aag agc cca ctc<br>Arg Thr Thr Glu Trp Leu Phe Gly Pro Met Val Asn Lys Ser Pro Leu<br>130                          135                       140 | | 432 |
| ttc cag ggt caa cgg gat gct gca gac cct gac aca ctc ctt caa atc<br>Phe Gln Gly Gln Arg Asp Ala Ala Asp Pro Asp Thr Leu Leu Gln Ile<br>145                          150                       155                     160 | | 480 |
| tat ggg tat cct gca tgc cta gga gca ata att gtc caa gtc tgg att<br>Tyr Gly Tyr Pro Ala Cys Leu Gly Ala Ile Ile Val Gln Val Trp Ile<br>                    165                       170                       175 | | 528 |
| gtg ctg gtg aag gcc atc aca agc agc gcc ggc tta agg aaa ggg ttc<br>Val Leu Val Lys Ala Ile Thr Ser Ser Ala Gly Leu Arg Lys Gly Phe<br>                    180                       185                       190 | | 576 |
| ttc aac agg tta gag gcg ttc aga caa gac ggc acc gtg aaa ggt gcc<br>Phe Asn Arg Leu Glu Ala Phe Arg Gln Asp Gly Thr Val Lys Gly Ala<br>              195                       200                       205 | | 624 |
| tta gtt ttc act ggg gag aca gtt gag ggg ata ggc tcg gtt atg aga<br>Leu Val Phe Thr Gly Glu Thr Val Glu Gly Ile Gly Ser Val Met Arg<br>210                          215                       220 | | 672 |
| tct cag caa agc ctt gta tct ctc atg gtt gag acc ctt gtg act atg<br>Ser Gln Gln Ser Leu Val Ser Leu Met Val Glu Thr Leu Val Thr Met<br>225                          230                       235                     240 | | 720 |
| aat act gca aga tct gat ctc acc aca tta gag aag aac atc cag atc<br>Asn Thr Ala Arg Ser Asp Leu Thr Thr Leu Glu Lys Asn Ile Gln Ile<br>                    245                       250                       255 | | 768 |
| gtt ggg aac tac atc cga gat gca ggg ctg gct tcc ttc atg aac act<br>Val Gly Asn Tyr Ile Arg Asp Ala Gly Leu Ala Ser Phe Met Asn Thr<br>              260                       265                       270 | | 816 |
| att aaa tat ggg gtg gag aca aag atg gca gct cta acg ttg tca aac<br>Ile Lys Tyr Gly Val Glu Thr Lys Met Ala Ala Leu Thr Leu Ser Asn<br>                    275                       280                       285 | | 864 |
| ctg agg ccc gat att aat aag ctt aga agc ctc ata gac acc tac ctg<br>Leu Arg Pro Asp Ile Asn Lys Leu Arg Ser Leu Ile Asp Thr Tyr Leu<br>290                          295                       300 | | 912 |
| tca aaa ggc ccc aga gct ccc ttt atc tgt atc ctc aag gac cct gtt<br>Ser Lys Gly Pro Arg Ala Pro Phe Ile Cys Ile Leu Lys Asp Pro Val<br>305                          310                       315                     320 | | 960 |
| cat ggt gaa ttt gct cca ggc aat tat cct gca cta tgg agt tac gcc<br>His Gly Glu Phe Ala Pro Gly Asn Tyr Pro Ala Leu Trp Ser Tyr Ala<br>                    325                       330                       335 | | 1008 |
| atg gga gtc gcc gtc gta cag aac aag gca atg cag cag tac gtc aca<br>Met Gly Val Ala Val Val Gln Asn Lys Ala Met Gln Gln Tyr Val Thr<br>              340                       345                       350 | | 1056 |
| ggg agg aca tac ctt gat atg gaa atg ttc tta cta gga caa gcc gtg<br>Gly Arg Thr Tyr Leu Asp Met Glu Met Phe Leu Leu Gly Gln Ala Val<br>                    355                       360                       365 | | 1104 |
| gca aag gat gct gaa tcg aag atc agc agt gcc ttg gaa gat gag tta<br>Ala Lys Asp Ala Glu Ser Lys Ile Ser Ser Ala Leu Glu Asp Glu Leu<br>370                          375                       380 | | 1152 |
| gga gtg acg gat aca gcc aag ggg agg ctc aga cat cat ctg gca aac<br>Gly Val Thr Asp Thr Ala Lys Gly Arg Leu Arg His His Leu Ala Asn<br>385                          390                       395                     400 | | 1200 |
| ttg tcc ggt ggg gat ggt gct tac cac aaa cca aca ggc ggt ggt gca<br>Leu Ser Gly Gly Asp Gly Ala Tyr His Lys Pro Thr Gly Gly Gly Ala<br>                    405                       410                       415 | | 1248 |

```
att gag gta gct cta gac aat gcc gat atc gac cta gaa aca aaa gct    1296
Ile Glu Val Ala Leu Asp Asn Ala Asp Ile Asp Leu Glu Thr Lys Ala
        420                 425                 430 cat gcg gac cag gac gct agg ggt tgg ggt gga gat agt ggt gaa aga    1344
His Ala Asp Gln Asp Ala Arg Gly Trp Gly Gly Asp Ser Gly Glu Arg
            435                 440                 445 tgg gca cgt cag gtg agt ggt ggc cac ttt gtc aca cta cat ggg gct    1392
Trp Ala Arg Gln Val Ser Gly Gly His Phe Val Thr Leu His Gly Ala
450                 455                 460 gaa cgg tta gag gag gaa acc aat gat gag gat gta tca gac ata gag    1440
Glu Arg Leu Glu Glu Glu Thr Asn Asp Glu Asp Val Ser Asp Ile Glu
465                 470                 475                 480 aga aga ata gcc atg aga ctc gca gag aga cgg caa gag gat tct gca    1488
Arg Arg Ile Ala Met Arg Leu Ala Glu Arg Arg Gln Glu Asp Ser Ala
                485                 490                 495 acc cat gga gat gaa ggc cgc aat aac ggt gtc gat cac gac gaa gat    1536
Thr His Gly Asp Glu Gly Arg Asn Asn Gly Val Asp His Asp Glu Asp
            500                 505                 510 gac gat gcc gca gca gta gct ggg gta gga gga atc tag                1575
Asp Asp Ala Ala Ala Val Ala Gly Val Gly Gly Ile
        515                 520

<210> SEQ ID NO 2
<211> LENGTH: 524
<212> TYPE: PRT
<213> ORGANISM: Sendai virus

<400> SEQUENCE: 2

Met Ala Gly Leu Leu Ser Thr Phe Asp Thr Phe Ser Ser Arg Arg Ser
1               5                   10                  15

Glu Ser Ile Asn Lys Ser Gly Gly Gly Ala Val Ile Pro Gly Gln Arg
            20                  25                  30

Ser Thr Val Ser Val Phe Val Leu Gly Pro Ser Val Thr Asp Asp Ala
        35                  40                  45

Asp Lys Leu Phe Ile Ala Thr Thr Phe Leu Ala His Ser Leu Asp Thr
    50                  55                  60

Asp Lys Gln His Ser Gln Arg Gly Gly Phe Leu Val Ser Leu Leu Ala
65                  70                  75                  80

Met Ala Tyr Ser Ser Pro Glu Leu Tyr Leu Thr Thr Asn Gly Val Asn
                85                  90                  95

Ala Asp Val Lys Tyr Val Ile Tyr Asn Ile Glu Lys Asp Pro Lys Arg
            100                 105                 110

Thr Lys Thr Asp Gly Phe Ile Val Lys Thr Arg Asp Met Glu Tyr Glu
        115                 120                 125

Arg Thr Thr Glu Trp Leu Phe Gly Pro Met Val Asn Lys Ser Pro Leu
    130                 135                 140

Phe Gln Gly Gln Arg Asp Ala Ala Asp Pro Asp Thr Leu Leu Gln Ile
145                 150                 155                 160

Tyr Gly Tyr Pro Ala Cys Leu Gly Ala Ile Ile Val Gln Val Trp Ile
                165                 170                 175

Val Leu Val Lys Ala Ile Thr Ser Ser Ala Gly Leu Arg Lys Gly Phe
            180                 185                 190

Phe Asn Arg Leu Glu Ala Phe Arg Gln Asp Gly Thr Val Lys Gly Ala
        195                 200                 205

Leu Val Phe Thr Gly Glu Thr Val Glu Gly Ile Gly Ser Val Met Arg
    210                 215                 220

Ser Gln Gln Ser Leu Val Ser Leu Met Val Glu Thr Leu Val Thr Met
```

```
                225                 230                 235                 240
Asn Thr Ala Arg Ser Asp Leu Thr Thr Leu Glu Lys Asn Ile Gln Ile
                    245                 250                 255
Val Gly Asn Tyr Ile Arg Asp Ala Gly Leu Ala Ser Phe Met Asn Thr
                260                 265                 270
Ile Lys Tyr Gly Val Glu Thr Lys Met Ala Ala Leu Thr Leu Ser Asn
            275                 280                 285
Leu Arg Pro Asp Ile Asn Lys Leu Arg Ser Leu Ile Asp Thr Tyr Leu
        290                 295                 300
Ser Lys Gly Pro Arg Ala Pro Phe Ile Cys Ile Leu Lys Asp Pro Val
305                 310                 315                 320
His Gly Glu Phe Ala Pro Gly Asn Tyr Pro Ala Leu Trp Ser Tyr Ala
                325                 330                 335
Met Gly Val Ala Val Gln Asn Lys Ala Met Gln Gln Tyr Val Thr
                340                 345                 350
Gly Arg Thr Tyr Leu Asp Met Glu Met Phe Leu Leu Gly Gln Ala Val
        355                 360                 365
Ala Lys Asp Ala Glu Ser Lys Ile Ser Ser Ala Leu Glu Asp Glu Leu
    370                 375                 380
Gly Val Thr Asp Thr Ala Lys Gly Arg Leu Arg His Leu Ala Asn
385                 390                 395                 400
Leu Ser Gly Gly Asp Gly Ala Tyr His Lys Pro Thr Gly Gly Ala
                405                 410                 415
Ile Glu Val Ala Leu Asp Asn Ala Asp Ile Asp Leu Glu Thr Lys Ala
                420                 425                 430
His Ala Asp Gln Asp Ala Arg Gly Trp Gly Gly Asp Ser Gly Glu Arg
            435                 440                 445
Trp Ala Arg Gln Val Ser Gly Gly His Phe Val Thr Leu His Gly Ala
        450                 455                 460
Glu Arg Leu Glu Glu Thr Asn Asp Glu Asp Val Ser Asp Ile Glu
465                 470                 475                 480
Arg Arg Ile Ala Met Arg Leu Ala Glu Arg Gln Glu Asp Ser Ala
                485                 490                 495
Thr His Gly Asp Glu Gly Arg Asn Asn Gly Val Asp His Asp Glu Asp
            500                 505                 510
Asp Asp Ala Ala Ala Val Ala Gly Val Gly Gly Ile
            515                 520

<210> SEQ ID NO 3
<211> LENGTH: 174
<212> TYPE: DNA
<213> ORGANISM: Artificial
<220> FEATURE:
<223> OTHER INFORMATION: Modified antigen binding amino acid sequence
      derived from B domain of

```
Ser Leu Lys Asp Asp Pro Ser Gln Ser Ala Asn Leu Leu Ala Glu Ala
        35                  40                  45 aaa aag cta aat gat gct cag gcg ccg aaa                              174
Lys Lys Leu Asn Asp Ala Gln Ala Pro Lys
        50                  55

<210> SEQ ID NO 4
<211> LENGTH: 58
<212> TYPE: PRT
<213> ORGANISM: Artificial
<220> FEATURE:
<223> OTHER INFORMATION: Modified antigen binding amino acid sequence
      derived from B domain of Protein A (Staphylococcus aureus)

<400> SEQUENCE: 4

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
        50                  55

<210> SEQ ID NO 5
<211> LENGTH: 1977
<212> TYPE: DNA
<213> ORGANISM: Artificial
<220> FEATURE:
<223> OTHER INFORMATION: Fusion protein includes antibody binding amino
      acid sequence and Sendai virus nucleocapsid protein
<220> FEATURE:
<221> NAME/KEY: CDS
<222> LOCATION: (1)..(1977)
<223> OTHER INFORMATION:

<400> SEQUENCE: 5 atg gaa cac gat gaa gcc gta gac aac aaa ttc aac aaa gaa caa caa     48
Met Glu His Asp Glu Ala Val Asp Asn Lys Phe Asn Lys Glu Gln Gln
1               5                   10                  15 aac gcg ttc tat gag atc tta cat tta cct aac tta aac gaa gaa caa     96
Asn Ala Phe Tyr Glu Ile Leu His Leu Pro Asn Leu Asn Glu Glu Gln
            20                  25                  30 cga aac gcc ttc atc caa agt tta aaa gat gac cca agc caa agc gct    144
Arg Asn Ala Phe Ile Gln Ser Leu Lys Asp Asp Pro Ser Gln Ser Ala
        35                  40                  45 aac ctt tta gca gaa gct aaa aag cta aat gat gct cag gcg ccg aaa    192
Asn Leu Leu Ala Glu Ala Lys Lys Leu Asn Asp Ala Gln Ala Pro Lys
    50                  55                  60 gta gac aac aaa ttc aac aaa gaa caa caa aac gcg ttc tat gag atc    240
Val Asp Asn Lys Phe Asn Lys Glu Gln Gln Asn Ala Phe Tyr Glu Ile
65                  70                  75                  80 tta cat tta cct aac tta aac gaa gaa caa cga aac gcc ttc atc caa    288
Leu His Leu Pro Asn Leu Asn Glu Glu Gln Arg Asn Ala Phe Ile Gln
                85                  90                  95 agt tta aaa gat gac cca agc caa agc gct aac ctt tta gca gaa gct    336
Ser Leu Lys Asp Asp Pro Ser Gln Ser Ala Asn Leu Leu Ala Glu Ala
            100                 105                 110 aaa aag cta aat gat gct cag gcg ccg aaa gta gac gcg aat tcg agc    384
Lys Lys Leu Asn Asp Ala Gln Ala Pro Lys Val Asp Ala Asn Ser Ser
        115                 120                 125 tcg gta ccc ggg gat ccg atg gcc ggg ttg ttg agc acc ttc gat aca    432
Ser Val Pro Gly Asp Pro Met Ala Gly Leu Leu Ser Thr Phe Asp Thr
    130                 135                 140
```

```
ttt agc tct agg agg agc gaa agt att aat aag tcg gga gga ggt gct    480
Phe Ser Ser Arg Arg Ser Glu Ser Ile Asn Lys Ser Gly Gly Gly Ala
145                 150                 155                 160 gtt atc ccc ggc cag agg agc aca gtc tca gtg ttc gta cta ggc cca    528
Val Ile Pro Gly Gln Arg Ser Thr Val Ser Val Phe Val Leu Gly Pro
                165                 170                 175 agt gtg act gat gat gca gac aag tta ttc att gca act acc ttc cta    576
Ser Val Thr Asp Asp Ala Asp Lys Leu Phe Ile Ala Thr Thr Phe Leu
            180                 185                 190 gct cac tca ttg gac aca gat aag cag cac tct cag aga gga ggg ttc    624
Ala His Ser Leu Asp Thr Asp Lys Gln His Ser Gln Arg Gly Gly Phe
        195                 200                 205 ctc gtc tct ctg ctt gcc atg gct tac agt agt cca gaa ttg tac ttg    672
Leu Val Ser Leu Leu Ala Met Ala Tyr Ser Ser Pro Glu Leu Tyr Leu
    210                 215                 220 aca aca aac gga gta aac gcc gat gtc aaa tat gtg atc tac aac ata    720
Thr Thr Asn Gly Val Asn Ala Asp Val Lys Tyr Val Ile Tyr Asn Ile
225                 230                 235                 240 gag aaa gac cct aag agg acg aag aca gac gga ttc att gtg aag acg    768
Glu Lys Asp Pro Lys Arg Thr Lys Thr Asp Gly Phe Ile Val Lys Thr
                245                 250                 255 aga gat atg gaa tat gag agg acc aca gaa tgg ctg ttt gga cct atg    816
Arg Asp Met Glu Tyr Glu Arg Thr Thr Glu Trp Leu Phe Gly Pro Met
            260                 265                 270 gtc aac aag agc cca ctc ttc cag ggt caa cgg gat gct gca gac cct    864
Val Asn Lys Ser Pro Leu Phe Gln Gly Gln Arg Asp Ala Ala Asp Pro
        275                 280                 285 gac aca ctc ctt caa atc tat ggg tat cct gca tgc cta gga gca ata    912
Asp Thr Leu Leu Gln Ile Tyr Gly Tyr Pro Ala Cys Leu Gly Ala Ile
    290                 295                 300 att gtc caa gtc tgg att gtg ctg gtg aag gcc atc aca agc agc gcc    960
Ile Val Gln Val Trp Ile Val Leu Val Lys Ala Ile Thr Ser Ser Ala
305                 310                 315                 320 ggc tta agg aaa ggg ttc ttc aac agg tta gag gcg ttc aga caa gac   1008
Gly Leu Arg Lys Gly Phe Phe Asn Arg Leu Glu Ala Phe Arg Gln Asp
                325                 330                 335 ggc acc gtg aaa ggt gcc tta gtt ttc act ggg gag aca gtt gag ggg   1056
Gly Thr Val Lys Gly Ala Leu Val Phe Thr Gly Glu Thr Val Glu Gly
            340                 345                 350 ata ggc tcg gtt atg aga tct cag caa agc ctt gta tct ctc atg gtt   1104
Ile Gly Ser Val Met Arg Ser Gln Gln Ser Leu Val Ser Leu Met Val
        355                 360                 365 gag acc ctt gtg act atg aat act gca aga tct gat ctc acc aca tta   1152
Glu Thr Leu Val Thr Met Asn Thr Ala Arg Ser Asp Leu Thr Thr Leu
    370                 375                 380 gag aag aac atc cag atc gtt ggg aac tac atc cga gat gca ggg ctg   1200
Glu Lys Asn Ile Gln Ile Val Gly Asn Tyr Ile Arg Asp Ala Gly Leu
385                 390                 395                 400 gct tcc ttc atg aac act att aaa tat ggg gtg gag aca aag atg gca   1248
Ala Ser Phe Met Asn Thr Ile Lys Tyr Gly Val Glu Thr Lys Met Ala
                405                 410                 415 gct cta acg ttg tca aac ctg agg ccc gat att aat aag ctt aga agc   1296
Ala Leu Thr Leu Ser Asn Leu Arg Pro Asp Ile Asn Lys Leu Arg Ser
            420                 425                 430 ctc ata gac acc tac ctg tca aaa ggc ccc aga gct ccc ttt atc tgt   1344
Leu Ile Asp Thr Tyr Leu Ser Lys Gly Pro Arg Ala Pro Phe Ile Cys
        435                 440                 445 atc ctc aag gac cct gtt cat ggt gaa ttt gct cca ggc aat tat cct   1392
Ile Leu Lys Asp Pro Val His Gly Glu Phe Ala Pro Gly Asn Tyr Pro
    450                 455                 460
```

```
gca cta tgg agt tac gcc atg gga gtc gcc gtc gta cag aac aag gca      1440
Ala Leu Trp Ser Tyr Ala Met Gly Val Ala Val Val Gln Asn Lys Ala
465                 470                 475                 480 atg cag cag tac gtc aca ggg agg aca tac ctt gat atg gaa atg ttc      1488
Met Gln Gln Tyr Val Thr Gly Arg Thr Tyr Leu Asp Met Glu Met Phe
                485                 490                 495 tta cta gga caa gcc gtg gca aag gat gct gaa tcg aag atc agc agt      1536
Leu Leu Gly Gln Ala Val Ala Lys Asp Ala Glu Ser Lys Ile Ser Ser
            500                 505                 510 gcc ttg gaa gat gag tta gga gtg acg gat aca gcc aag ggg agg ctc      1584
Ala Leu Glu Asp Glu Leu Gly Val Thr Asp Thr Ala Lys Gly Arg Leu
        515                 520                 525 aga cat cat ctg gca aac ttg tcc ggt ggg gat ggt gct tac cac aaa      1632
Arg His His Leu Ala Asn Leu Ser Gly Gly Asp Gly Ala Tyr His Lys
    530                 535                 540 cca aca ggc ggt ggt gca att gag gta gct cta gac aat gcc gat atc      1680
Pro Thr Gly Gly Gly Ala Ile Glu Val Ala Leu Asp Asn Ala Asp Ile
545                 550                 555                 560 gac cta gaa aca aaa gct cat gcg gac cag gac gct agg ggt tgg ggt      1728
Asp Leu Glu Thr Lys Ala His Ala Asp Gln Asp Ala Arg Gly Trp Gly
                565                 570                 575 gga gat agt ggt gaa aga tgg gca cgt cag gtg agt ggt ggc cac ttt      1776
Gly Asp Ser Gly Glu Arg Trp Ala Arg Gln Val Ser Gly Gly His Phe
            580                 585                 590 gtc aca cta cat ggg gct gaa cgg tta gag gag gaa acc aat gat gag      1824
Val Thr Leu His Gly Ala Glu Arg Leu Glu Glu Glu Thr Asn Asp Glu
        595                 600                 605 gat gta tca gac ata gag aga aga ata gcc atg aga ctc gca gag aga      1872
Asp Val Ser Asp Ile Glu Arg Arg Ile Ala Met Arg Leu Ala Glu Arg
    610                 615                 620 cgg caa gag gat tct gca acc cat gga gat gaa ggc cgc aat aac ggt      1920
Arg Gln Glu Asp Ser Ala Thr His Gly Asp Glu Gly Arg Asn Asn Gly
625                 630                 635                 640 gtc gat cac gac gaa gat gac gat gcc gca gca gta gct ggg gta gga      1968
Val Asp His Asp Glu Asp Asp Asp Ala Ala Ala Val Ala Gly Val Gly
                645                 650                 655 gga atc tag                                                          1977
Gly Ile <210> SEQ ID NO 6
<211> LENGTH: 658
<212> TYPE: PRT
<213> ORGANISM: Artificial
<220> FEATURE:
<223> OTHER INFORMATION: Fusion protein includes antibody binding amino
      acid sequence and Sendai virus nucleocapsid protein

<400> SEQUENCE: 6

Met Glu His Asp Glu Ala Val Asp Asn Lys Phe Asn L

```
Ser Leu Lys Asp Asp Pro Ser Gln Ser Ala Asn Leu Leu Ala Glu Ala
            100                 105                 110

Lys Lys Leu Asn Asp Ala Gln Ala Pro Lys Val Asp Ala Asn Ser Ser
        115                 120                 125

Ser Val Pro Gly Asp Pro Met Ala Gly Leu Leu Ser Thr Phe Asp Thr
    130                 135                 140

Phe Ser Ser Arg Arg Ser Glu Ser Ile Asn Lys Ser Gly Gly Gly Ala
145                 150                 155                 160

Val Ile Pro Gly Gln Arg Ser Thr Val Ser Val Phe Val Leu Gly Pro
                165                 170                 175

Ser Val Thr Asp Asp Ala Asp Lys Leu Phe Ile Ala Thr Thr Phe Leu
            180                 185                 190

Ala His Ser Leu Asp Thr Asp Lys Gln His Ser Gln Arg Gly Gly Phe
        195                 200                 205

Leu Val Ser Leu Leu Ala Met Ala Tyr Ser Ser Pro Glu Leu Tyr Leu
    210                 215                 220

Thr Thr Asn Gly Val Asn Ala Asp Val Lys Tyr Val Ile Tyr Asn Ile
225                 230                 235                 240

Glu Lys Asp Pro Lys Arg Thr Lys Thr Asp Gly Phe Ile Val Lys Thr
                245                 250                 255

Arg Asp Met Glu Tyr Glu Arg Thr Thr Glu Trp Leu Phe Gly Pro Met
            260                 265                 270

Val Asn Lys Ser Pro Leu Phe Gln Gly Gln Arg Asp Ala Ala Asp Pro
        275                 280                 285

Asp Thr Leu Leu Gln Ile Tyr Gly Tyr Pro Ala Cys Leu Gly Ala Ile
    290                 295                 300

Ile Val Gln Val Trp Ile Val Leu Val Lys Ala Ile Thr Ser Ser Ala
305                 310                 315                 320

Gly Leu Arg Lys Gly Phe Phe Asn Arg Leu Glu Ala Phe Arg Gln Asp
                325                 330                 335

Gly Thr Val Lys Gly Ala Leu Val Phe Thr Gly Glu Thr Val Glu Gly
            340                 345                 350

Ile Gly Ser Val Met Arg Ser Gln Gln Ser Leu Val Ser Leu Met Val
        355                 360                 365

Glu Thr Leu Val Thr Met Asn Thr Ala Arg Ser Asp Leu Thr Thr Leu
    370                 375                 380

Glu Lys Asn Ile Gln Ile Val Gly Asn Tyr Ile Arg Asp Ala Gly Leu
385                 390                 395                 400

Ala Ser Phe Met Asn Thr Ile Lys Tyr Gly Val Glu Thr Lys Met Ala
                405                 410                 415

Ala Leu Thr Leu Ser Asn Leu Arg Pro Asp Ile Asn Lys Leu Arg Ser
            420                 425                 430

Leu Ile Asp Thr Tyr Leu Ser Lys Gly Pro Arg Ala Pro Phe Ile Cys
        435                 440                 445

Ile Leu Lys Asp Pro Val His Gly Glu Phe Ala Pro Gly Asn Tyr Pro
450                 455                 460

Ala Leu Trp Ser Tyr Ala Met Gly Val Ala Val Gln Asn Lys Ala
465                 470                 475                 480

Met Gln Gln Tyr Val Thr Gly Arg Thr Tyr Leu Asp Met Glu Met Phe
                485                 490                 495

Leu Leu Gly Gln Ala Val Ala Lys Asp Ala Glu Ser Lys Ile Ser Ser
            500                 505                 510

Ala Leu Glu Asp Glu Leu Gly Val Thr Asp Thr Ala Lys Gly Arg Leu
```

-continued

```
                515                 520                 525

Arg His His Leu Ala Asn Leu Ser Gly Gly Asp Gly Ala Tyr His Lys
        530                 535                 540

Pro Thr Gly Gly Gly Ala Ile Glu Val Ala Leu Asp Asn Ala Asp Ile
545                 550                 555                 560

Asp Leu Glu Thr Lys Ala His Ala Asp Gln Asp Ala Arg Gly Trp Gly
                565                 570                 575

Gly Asp Ser Gly Glu Arg Trp Ala Arg Gln Val Ser Gly Gly His Phe
            580                 585                 590

Val Thr Leu His Gly Ala Glu Arg Leu Glu Glu Glu Thr Asn Asp Glu
        595                 600                 605

Asp Val Ser Asp Ile Glu Arg Arg Ile Ala Met Arg Leu Ala Glu Arg
    610                 615                 620

Arg Gln Glu Asp Ser Ala Thr His Gly Asp Glu Gly Arg Asn Asn Gly
625                 630                 635                 640

Val Asp His Asp Glu Asp Asp Ala Ala Ala Val Ala Gly Val Gly
                645                 650                 655

Gly Ile

<210> SEQ ID NO 7
<211> LENGTH: 35
<212> TYPE: DNA
<213> ORGANISM: Artificial
<220> FEATURE:
<223> OTHER INFORMATION: Oligonucleotide to act as a primer for PCR

<400> SEQUENCE: 7
gcaaatgcca tggaacacga tgaagccgta gacaa                             35

<210> SEQ ID NO 8
<211> LENGTH: 35
<212> TYPE: DNA
<213> ORGANISM: Artificial
<220> FEATURE:
<223> OTHER INFORMATION: Oligonucleotide to act as a primer for PCR

<400> SEQUENCE: 8
ggatcaccaa gcttttagct cgaattcgcg tctac                             35

<210> SEQ ID NO 9
<211> LENGTH: 25
<212> TYPE: DNA
<213> ORGANISM: Artificial
<220> FEATURE:
<223> OTHER INFORMATION: Oligonucleotide to act as a primer for reverse
      transcription

<400> SEQUENCE: 9
accaaacaag agaaaaaaca tgtat                                        25

<210> SEQ ID NO 10
<211> LENGTH: 35
<212> TYPE: DNA
<213> ORGANISM: Artificial
<220> FEATURE:
<223> OTHER INFORMATION: Oligonucleotide to act as a primer for PCR

<400> SEQUENCE: 10
tgccaaagga tccgatggcc gggttgttga gcacc                             35

<210> SEQ ID NO 11
<211> LENGTH: 35
```

-continued

<210> SEQ ID NO 11
<211> LENGTH: 35
<212> TYPE: DNA
<213> ORGANISM: Artificial
<220> FEATURE:
<223> OTHER INFORMATION: Oligonucleotide to act as a primer for PCR

<400> SEQUENCE: 11
gcctcgtctc gagctagatt cctcctaccc cagct                           35

<210> SEQ ID NO 12
<211> LENGTH: 1605
<212> TYPE: DNA
<213> ORGANISM: Artificial
<220> FEATURE:
<223> OTHER INFORMATION: Fusion protein includes antibody binding amino
      acid sequence and Sendai virus nucleocapsid protein (ZZ-NPK1)
<220> FEATURE:
<221> NAME/KEY: CDS
<222> LOCATION: (1)..(1605)
<223> OTHER INFORMATION:

<400> SEQUENCE: 12

```
atg gaa cac gat gaa gcc gta gac aac aaa ttc aac aaa gaa caa caa       48
Met Glu His Asp Glu Ala Val Asp Asn Lys Phe Asn Lys Glu Gln Gln
1               5                   10                  15 aac gcg ttc tat gag atc tta cat tta cct aac tta aac gaa gaa caa       96
Asn Ala Phe Tyr Glu Ile Leu His Leu Pro Asn Leu Asn Glu Glu Gln
            20                  25                  30 cga aac gcc ttc atc caa agt tta aaa gat gac cca agc caa agc gct      144
Arg Asn Ala Phe Ile Gln Ser Leu Lys Asp Asp Pro Ser Gln Ser Ala
        35                  40                  45 aac ctt tta gca gaa gct aaa aag cta aat gat gct cag gcg ccg aaa      192
Asn Leu Leu Ala Glu Ala Lys Lys Leu Asn Asp Ala Gln Ala Pro Lys
    50                  55                  60 gta gac aac aaa ttc aac aaa gaa caa caa aac gcg ttc tat gag atc      240
Val Asp Asn Lys Phe Asn Lys Glu Gln Gln Asn Ala Phe Tyr Glu Ile
65                  70                  75                  80 tta cat tta cct aac tta aac gaa gaa caa cga aac gcc ttc atc caa      288
Leu His Leu Pro Asn Leu Asn Glu Glu Gln Arg Asn Ala Phe Ile Gln
                85                  90                  95 agt tta aaa gat gac cca agc caa agc gct aac ctt tta gca gaa gct      336
Ser Leu Lys Asp Asp Pro Ser Gln Ser Ala Asn Leu Leu Ala Glu Ala
            100                 105                 110 aaa aag cta aat gat gct cag gcg ccg aaa gta gac gcg aat tcg agc      384
Lys Lys Leu Asn Asp Ala Gln Ala Pro Lys Val Asp Ala Asn Ser Ser
        115                 120                 125 tcg gta ccc ggg gat ccg atg gcc ggg ttg ttg agc acc ttc gat aca      432
Ser Val Pro Gly Asp Pro Met Ala Gly Leu Leu Ser Thr Phe Asp Thr
    130                 135                 140 ttt agc tct agg agg agc gaa agt att aat aag tcg gga gga ggt gct      480
Phe Ser Ser Arg Arg Ser Glu Ser Ile Asn Lys Ser Gly Gly Gly Ala
145                 150                 155                 160 gtt atc ccc ggc cag agg agc aca gtc tca gtg ttc gta cta ggc cca      528
Val Ile Pro Gly Gln Arg Ser Thr Val Ser Val Phe Val Leu Gly Pro
                165                 170                 175 agt gtg act gat gat gca gac aag tta ttc att gca act acc ttc cta      576
Ser Val Thr Asp Asp Ala Asp Lys Leu Phe Ile Ala Thr Thr Phe Leu
            180                 185                 190 gct cac tca ttg gac aca gat aag cag cac tct cag aga gga ggg ttc      624
Ala His Ser Leu Asp Thr Asp Lys Gln His Ser Gln Arg Gly Gly Phe
        195                 200                 205 ctc gtc tct ctg ctt gcc atg gct tac agt agt cca gaa ttg tac ttg      672
Leu Val Ser Leu Leu Ala Met Ala Tyr Ser Ser Pro Glu Leu Tyr Leu
    210                 215                 220
```

```
aca aca aac gga gta aac gcc gat gtc aaa tat gtg atc tac aac ata    720
Thr Thr Asn Gly Val Asn Ala Asp Val Lys Tyr Val Ile Tyr Asn Ile
225                 230                 235                 240 gag aaa gac cct aag agg acg aag aca gac gga ttc att gtg aag acg    768
Glu Lys Asp Pro Lys Arg Thr Lys Thr Asp Gly Phe Ile Val Lys Thr
            245                 250                 255 aga gat atg gaa tat gag agg acc aca gaa tgg ctg ttt gga cct atg    816
Arg Asp Met Glu Tyr Glu Arg Thr Thr Glu Trp Leu Phe Gly Pro Met
        260                 265                 270 gtc aac aag agc cca ctc ttc cag ggt caa cgg gat gct gca gac cct    864
Val Asn Lys Ser Pro Leu Phe Gln Gly Gln Arg Asp Ala Ala Asp Pro
    275                 280                 285 gac aca ctc ctt caa atc tat ggg tat cct gca tgc cta gga gca ata    912
Asp Thr Leu Leu Gln Ile Tyr Gly Tyr Pro Ala Cys Leu Gly Ala Ile
290                 295                 300 att gtc caa gtc tgg att gtg ctg gtg aag gcc atc aca agc agc gcc    960
Ile Val Gln Val Trp Ile Val Leu Val Lys Ala Ile Thr Ser Ser Ala
305                 310                 315                 320 ggc tta agg aaa ggg ttc ttc aac agg tta gag gcg ttc aga caa gac   1008
Gly Leu Arg Lys Gly Phe Phe Asn Arg Leu Glu Ala Phe Arg Gln Asp
            325                 330                 335 ggc acc gtg aaa ggt gcc tta gtt ttc act ggg gag aca gtt gag ggg   1056
Gly Thr Val Lys Gly Ala Leu Val Phe Thr Gly Glu Thr Val Glu Gly
        340                 345                 350 ata ggc tcg gtt atg aga tct cag caa agc ctt gta tct ctc atg gtt   1104
Ile Gly Ser Val Met Arg Ser Gln Gln Ser Leu Val Ser Leu Met Val
    355                 360                 365 gag acc ctt gtg act atg aat act gca aga tct gat ctc acc aca tta   1152
Glu Thr Leu Val Thr Met Asn Thr Ala Arg Ser Asp Leu Thr Thr Leu
370                 375                 380 gag aag aac atc cag atc gtt ggg aac tac atc cga gat gca ggg ctg   1200
Glu Lys Asn Ile Gln Ile Val Gly Asn Tyr Ile Arg Asp Ala Gly Leu
385                 390                 395                 400 gct tcc ttc atg aac act att aaa tat ggg gtg gag aca aag atg gca   1248
Ala Ser Phe Met Asn Thr Ile Lys Tyr Gly Val Glu Thr Lys Met Ala
            405                 410                 415 gct cta acg ttg tca aac ctg agg ccc gat att aat aag ctt aga agc   1296
Ala Leu Thr Leu Ser Asn Leu Arg Pro Asp Ile Asn Lys Leu Arg Ser
        420                 425                 430 ctc ata gac acc tac ctg tca aaa ggc ccc aga gct ccc ttt atc tgt   1344
Leu Ile Asp Thr Tyr Leu Ser Lys Gly Pro Arg Ala Pro Phe Ile Cys
    435                 440                 445 atc ctc aag gac cct gtt cat ggt gaa ttt gct cca ggc aat tat cct   1392
Ile Leu Lys Asp Pro Val His Gly Glu Phe Ala Pro Gly Asn Tyr Pro
450                 455                 460 gca cta tgg agt tac gcc atg gga gtc gcc gtc gta cag aac aag gca   1440
Ala Leu Trp Ser Tyr Ala Met Gly Val Ala Val Val Gln Asn Lys Ala
465                 470                 475                 480 atg cag cag tac gtc aca ggg agg aca tac ctt gat atg gaa atg ttc   1488
Met Gln Gln Tyr Val Thr Gly Arg Thr Tyr Leu Asp Met Glu Met Phe
            485                 490                 495 tta cta gga caa gcc gtg gca aag gat gct gaa tcg aag atc agc agt   1536
Leu Leu Gly Gln Ala Val Ala Lys Asp Ala Glu Ser Lys Ile Ser Ser
        500                 505                 510 gcc ttg gaa gat gag tta gga gtg acg gat aca gcc aag ggg agg ctc   1584
Ala Leu Glu Asp Glu Leu Gly Val Thr Asp Thr Ala Lys Gly Arg Leu
    515                 520                 525 aga cat cat ctg gca aac tag                                       1605
Arg His His Leu Ala Asn
        530
```

-continued

```
<210> SEQ ID NO 13
<211> LENGTH: 534
<212> TYPE: PRT
<213> ORGANISM: Artificial
<220> FEATURE:
<223> OTHER INFORMATION: Fusion protein includes antibody binding amino
      acid sequence and Sendai virus nucleocapsid protein (ZZ-NPK1)

<400> SEQUENCE

-continued

```
Glu Thr Leu Val Thr Met Asn Thr Ala Arg Ser Asp Leu Thr Thr Leu
    370                 375                 380

Glu Lys Asn Ile Gln Ile Val Gly Asn Tyr Ile Arg Asp Ala Gly Leu
385                 390                 395                 400

Ala Ser Phe Met Asn Thr Ile Lys Tyr Gly Val Glu Thr Lys Met Ala
            405                 410                 415

Ala Leu Thr Leu Ser Asn Leu Arg Pro Asp Ile Asn Lys Leu Arg Ser
        420                 425                 430

Leu Ile Asp Thr Tyr Leu Ser Lys Gly Pro Arg Ala Pro Phe Ile Cys
    435                 440                 445

Ile Leu Lys Asp Pro Val His Gly Glu Phe Ala Pro Gly Asn Tyr Pro
450                 455                 460

Ala Leu Trp Ser Tyr Ala Met Gly Val Ala Val Val Gln Asn Lys Ala
465                 470                 475                 480

Met Gln Gln Tyr Val Thr Gly Arg Thr Tyr Leu Asp Met Glu Met Phe
            485                 490                 495

Leu Leu Gly Gln Ala Val Ala Lys Asp Ala Glu Ser Lys Ile Ser Ser
        500                 505                 510

Ala Leu Glu Asp Glu Leu Gly Val Thr Asp Thr Ala Lys Gly Arg Leu
    515                 520                 525

Arg His His Leu Ala Asn
    530
```

<210> SEQ ID NO 14
<211> LENGTH: 1476
<212> TYPE: DNA
<213> ORGANISM: Artificial
<220> FEATURE:
<223> OTHER INFORMATION: Fusion protein includes antibody binding amino
      acid sequence and Sendai virus nucleocapsid protein (ZZ

|     |     |     |     |     |     |     |     |     |     |     |     |     |     |     |     |     |
|---|---|---|---|---|---|---|---|---|---|---|---|---|---|---|---|---|
| tcg | gta | ccc | ggg | gat | ccg | atg | gcc | ggg | ttg | ttg | agc | acc | ttc | gat | aca | 432 |
| Ser | Val | Pro | Gly | Asp | Pro | Met | Ala | Gly | Leu | Leu | Ser | Thr | Phe | Asp | Thr | |
| 130 | | | | 135 | | | | | 140 | | | | | | | |
| ttt | agc | tct | agg | agg | agc | gaa | agt | att | aat | aag | tcg | gga | gga | ggt | gct | 480 |
| Phe | Ser | Ser | Arg | Arg | Ser | Glu | Ser | Ile | Asn | Lys | Ser | Gly | Gly | Gly | Ala | |
| 145 | | | | | 150 | | | | | 155 | | | | | 160 | |
| gtt | atc | ccc | ggc | cag | agg | agc | aca | gtc | tca | gtg | ttc | gta | cta | ggc | cca | 528 |
| Val | Ile | Pro | Gly | Gln | Arg | Ser | Thr | Val | Ser | Val | Phe | Val | Leu | Gly | Pro | |
| | | | | 165 | | | | | 170 | | | | | 175 | | |
| agt | gtg | act | gat | gat | gca | gac | aag | tta | ttc | att | gca | act | acc | ttc | cta | 576 |
| Ser | Val | Thr | Asp | Asp | Ala | Asp | Lys | Leu | Phe | Ile | Ala | Thr | Thr | Phe | Leu | |
| | | | 180 | | | | | 185 | | | | | 190 | | | |
| gct | cac | tca | ttg | gac | aca | gat | aag | cag | cac | tct | cag | aga | gga | ggg | ttc | 624 |
| Ala | His | Ser | Leu | Asp | Thr | Asp | Lys | Gln | His | Ser | Gln | Arg | Gly | Gly | Phe | |
| | | 195 | | | | | 200 | | | | | 205 | | | | |
| ctc | gtc | tct | ctg | ctt | gcc | atg | gct | tac | agt | agt | cca | gaa | ttg | tac | ttg | 672 |
| Leu | Val | Ser | Leu | Leu | Ala | Met | Ala | Tyr | Ser | Ser | Pro | Glu | Leu | Tyr | Leu | |
| | 210 | | | | | 215 | | | | | 220 | | | | | |
| aca | aca | aac | gga | gta | aac | gcc | gat | gtc | aaa | tat | gtg | atc | tac | aac | ata | 720 |
| Thr | Thr | Asn | Gly | Val | Asn | Ala | Asp | Val | Lys | Tyr | Val | Ile | Tyr | Asn | Ile | |
| 225 | | | | 230 | | | | | 235 | | | | | 240 | | |
| gag | aaa | gac | cct | aag | agg | acg | aag | aca | gac | gga | ttc | att | gtg | aag | acg | 768 |
| Glu | Lys | Asp | Pro | Lys | Arg | Thr | Lys | Thr | Asp | Gly | Phe | Ile | Val | Lys | Thr | |
| | | | 245 | | | | | 250 | | | | | 255 | | | |
| aga | gat | atg | gaa | tat | gag | agg | acc | aca | gaa | tgg | ctg | ttt | gga | cct | atg | 816 |
| Arg | Asp | Met | Glu | Tyr | Glu | Arg | Thr | Thr | Glu | Trp | Leu | Phe | Gly | Pro | Met | |
| | | 260 | | | | | 265 | | | | | 270 | | | | |
| gtc | aac | aag | agc | cca | ctc | ttc | cag | ggt | caa | cgg | gat | gct | gca | gac | cct | 864 |
| Val | Asn | Lys | Ser | Pro | Leu | Phe | Gln | Gly | Gln | Arg | Asp | Ala | Ala | Asp | Pro | |
| | | 275 | | | | | 280 | | | | | 285 | | | | |
| gac | aca | ctc | ctt | caa | atc | tat | ggg | tat | cct | gca | tgc | cta | gga | gca | ata | 912 |
| Asp | Thr | Leu | Leu | Gln | Ile | Tyr | Gly | Tyr | Pro | Ala | Cys | Leu | Gly | Ala | Ile | |
| | 290 | | | | | 295 | | | | | 300 | | | | | |
| att | gtc | caa | gtc | tgg | att | gtg | ctg | gtg | aag | gcc | atc | aca | agc | agc | gcc | 960 |
| Ile | Val | Gln | Val | Trp | Ile | Val | Leu | Val | Lys | Ala | Ile | Thr | Ser | Ser | Ala | |
| 305 | | | | 310 | | | | | 315 | | | | | 320 | | |
| ggc | tta | agg | aaa | ggg | ttc | ttc | aac | agg | tta | gag | gcg | ttc | aga | caa | gac | 1008 |
| Gly | Leu | Arg | Lys | Gly | Phe | Phe | Asn | Arg | Leu | Glu | Ala | Phe | Arg | Gln | Asp | |
| | | | 325 | | | | | 330 | | | | | 335 | | | |
| ggc | acc | gtg | aaa | ggt | gcc | tta | gtt | ttc | act | ggg | gag | aca | gtt | gag | ggg | 1056 |
| Gly | Thr | Val | Lys | Gly | Ala | Leu | Val | Phe | Thr | Gly | Glu | Thr | Val | Glu | Gly | |
| | | | 340 | | | | | 345 | | | | | 350 | | | |
| ata | ggc | tcg | gtt | atg | aga | tct | cag | caa | agc | ctt | gta | tct | ctc | atg | gtt | 1104 |
| Ile | Gly | Ser | Val | Met | Arg | Ser | Gln | Gln | Ser | Leu | Val | Ser | Leu | Met | Val | |
| | | 355 | | | | | 360 | | | | | 365 | | | | |
| gag | acc | ctt | gtg | act | atg | aat | act | gca | aga | tct | gat | ctc | acc | aca | tta | 1152 |
| Glu | Thr | Leu | Val | Thr | Met | Asn | Thr | Ala | Arg | Ser | Asp | Leu | Thr | Thr | Leu | |
| | 370 | | | | | 375 | | | | | 380 | | | | | |
| gag | aag | aac | atc | cag | atc | gtt | ggg | aac | tac | atc | cga | gat | gca | ggg | ctg | 1200 |
| Glu | Lys | Asn | Ile | Gln | Ile | Val | Gly | Asn | Tyr | Ile | Arg | Asp | Ala | Gly | Leu | |
| 385 | | | | 390 | | | | | 395 | | | | | 400 | | |
| gct | tcc | ttc | atg | aac | act | att | aaa | tat | ggg | gtg | gag | aca | aag | atg | gca | 1248 |
| Ala | Ser | Phe | Met | Asn | Thr | Ile | Lys | Tyr | Gly | Val | Glu | Thr | Lys | Met | Ala | |
| | | | 405 | | | | | 410 | | | | | 415 | | | |
| gct | cta | acg | ttg | tca | aac | ctg | agg | ccc | gat | att | aat | aag | ctt | aga | agc | 1296 |
| Ala | Leu | Thr | Leu | Ser | Asn | Leu | Arg | Pro | Asp | Ile | Asn | Lys | Leu | Arg | Ser | |
| | | | 420 | | | | | 425 | | | | | 430 | | | |
| ctc | ata | gac | acc | tac | ctg | tca | aaa | ggc | ccc | aga | gct | ccc | ttt | atc | tgt | 1344 |
| Leu | Ile | Asp | Thr | Tyr | Leu | Ser | Lys | Gly | Pro | Arg | Ala | Pro | Phe | Ile | Cys | |
| | | 435 | | | | | 440 | | | | | 445 | | | | |

| | | | | | | | | | | | | |
|---|---|---|---|---|---|---|---|---|---|---|---|---|
| atc | ctc | aag | gac | cct | gtt | cat | ggt | gaa | ttt | gct | cca | ggc | aat | tat | cct | 1392 |
| Ile | Leu | Lys | Asp | Pro | Val | His | Gly | Glu | Phe | Ala | Pro | Gly | Asn | Tyr | Pro | |
| | 450 | | | | 455 | | | | | 460 | | | | | | |
| gca | cta | tgg | agt | tac | gcc | atg | gga | gtc | gcc | gtc | gta | cag | aac | aag | gca | 1440 |
| Ala | Leu | Trp | Ser | Tyr | Ala | Met | Gly | Val | Ala | Val | Val | Gln | Asn | Lys | Ala | |
| 465 | | | | | 470 | | | | | 475 | | | | | 480 | |
| atg | cag | cag | tac | gtc | aca | ggg | agg | aca | tac | ctt | tag | | | | | 1476 |
| Met | Gln | Gln | Tyr | Val | Thr | Gly | Arg | Thr | Tyr | Leu | | | | | | |
| | | | | 485 | | | | | 490 | | | | | | | |

<210> SEQ ID NO 15
<211> LENGTH: 491
<212> TYPE: PRT
<213> ORGANISM: Artificial
<220> FEATURE:
<223> OTHER INFORMATION: Fusion protein includes antibody binding amino
acid sequence and Sendai virus nucleocapsid protein (ZZ-NPK2)

<400> SEQUENCE: 15

```
Met Glu His Asp Glu Ala Val Asp Asn Lys Phe Asn Lys Glu Gln Gln
 1               5                  10                  15

Asn Ala Phe Tyr Glu Ile Leu His Leu Pro Asn Leu Asn Glu Glu Gln
            20                  25                  30

Arg Asn Ala Phe Ile Gln Ser Leu Lys Asp Asp Pro Ser Gln Ser Ala
        35                  40                  45

Asn Leu Leu Ala Glu Ala Lys Lys Leu Asn Asp Ala Gln Ala Pro Lys
50                  55                  60

Val Asp Asn Lys Phe Asn Lys Glu Gln Gln Asn Ala Phe Tyr Glu Ile
65                  70                  75                  80

Leu His Leu Pro Asn Leu Asn Glu Glu Gln Arg Asn Ala Phe Ile Gln
                85                  90                  95

Ser Leu Lys Asp Asp Pro Ser Gln Ser Ala Asn Leu Leu Ala Glu Ala
            100                 105                 110

Lys Lys Leu Asn Asp Ala Gln Ala Pro Lys Val Asp Ala Asn Ser Ser
        115                 120                 125

Ser Val Pro Gly Asp Pro Met Ala Gly Leu Leu Ser Thr Phe Asp Thr
130                 135                 140

Phe Ser Ser Arg Arg Ser Glu Ser Ile Asn Lys Ser Gly Gly Gly Ala
145                 150                 155                 160

Val Ile Pro Gly Gln Arg Ser Thr Val Ser Val Phe Val Leu Gly Pro
                165                 170                 175

Ser Val Thr Asp Asp Ala Asp Lys Leu Phe Ile Ala Thr Thr Phe Leu
            180                 185                 190

Ala His Ser Leu Asp Thr Asp Lys Gln His Ser Gln Arg Gly Gly Phe
        195                 200                 205

Leu Val Ser Leu Leu Ala Met Ala Tyr Ser Ser Pro Glu Leu Tyr Leu
210                 215                 220

Thr Thr Asn Gly Val Asn Ala Asp Val Lys Tyr Val Ile Tyr Asn Ile
225                 230                 235                 240

Glu Lys Asp Pro Lys Arg Thr Lys Thr Asp Gly Phe Ile Val Lys Thr
                245                 250                 255

Arg Asp Met Glu Tyr Glu Arg Thr Thr Glu Trp Leu Phe Gly Pro Met
            260                 265                 270

Val Asn Lys Ser Pro Leu Phe Gln Gly Gln Arg Asp Ala Ala Asp Pro
        275                 280                 285

Asp Thr Leu Leu Gln Ile Tyr Gly Tyr Pro Ala Cys Leu Gly Ala Ile
290                 295                 300
```

```
Ile Val Gln Val Trp Ile Val Leu Val Lys Ala Ile Thr Ser Ser Ala
305                 310                 315                 320

Gly Leu Arg Lys Gly Phe Phe Asn Arg Leu Glu Ala Phe Arg Gln Asp
                325                 330                 335

Gly Thr Val Lys Gly Ala Leu Val Phe Thr Gly Glu Thr Val Glu Gly
            340                 345                 350

Ile Gly Ser Val Met Arg Ser Gln Gln Ser Leu Val Ser Leu Met Val
        355                 360                 365

Glu Thr Leu Val Thr Met Asn Thr Ala Arg Ser Asp Leu Thr Thr Leu
370                 375                 380

Glu Lys Asn Ile Gln Ile Val Gly Asn Tyr Ile Arg Asp Ala Gly Leu
385                 390                 395                 400

Ala Ser Phe Met Asn Thr Ile Lys Tyr Gly Val Glu Thr Lys Met Ala
                405                 410                 415

Ala Leu Thr Leu Ser Asn Leu Arg Pro Asp Ile Asn Lys Leu Arg Ser
            420                 425                 430

Leu Ile Asp Thr Tyr Leu Ser Lys Gly Pro Arg Ala Pro Phe Ile Cys
        435                 440                 445

Ile Leu Lys Asp Pro Val His Gly Glu Phe Ala Pro Gly Asn Tyr Pro
450                 455                 460

Ala Leu Trp Ser Tyr Ala Met Gly Val Ala Val Val Gln Asn Lys Ala
465                 470                 475                 480

Met Gln Gln Tyr Val Thr Gly Arg Thr Tyr Leu
                485                 490

<210> SEQ ID NO 16
<211> LENGTH: 1176
<212> TYPE: DNA
<213> ORGANISM: Artificial
<220> FEATURE:
<223> OTHER INFORMATION: Fusion protein includes antibody binding amino
      acid sequence and Sendai virus nucleocapsid protein (ZZ-NPK3)
<220> FEATURE:
<221> NAME/KEY: CDS
<222> LOCATION: (1)..(1176)
<223> OTHER INFORMATION:

<400> SEQUENCE: 16 atg gaa cac gat gaa gcc gta gac aac aaa ttc aac aaa gaa caa caa      48
Met Glu His Asp Glu Ala Val Asp Asn Lys Phe Asn Lys Glu Gln Gln
1               5                   10                  15 aac gcg ttc tat gag atc tta cat tta cct aac tta aac gaa gaa caa      96
Asn Ala Phe Tyr Glu Ile Leu His Leu Pro Asn Leu Asn Glu Glu Gln
            20                  25                  30 cga aac gcc ttc atc caa agt tta aaa gat gac cca agc caa agc gct     144
Arg Asn Ala Phe Ile Gln Ser Leu Lys Asp Asp Pro Ser Gln Ser Ala
        35                  40                  45 aac ctt tta gca gaa gct aaa aag cta aat gat gct cag gcg ccg aaa     192
Asn Leu Leu Ala Glu Ala Lys Lys Leu Asn Asp Ala Gln Ala Pro Lys
    50                  55                  60 gta gac aac aaa ttc aac aaa gaa caa caa aac gcg ttc tat gag atc     240
Val Asp Asn Lys Phe Asn Lys Glu Gln Gln Asn Ala Phe Tyr Glu Ile
65                  70                  75                  80 tta cat tta cct aac tta aac gaa gaa caa cga aac gcc ttc atc caa     288
Leu His Leu Pro Asn Leu Asn Glu Glu Gln Arg Asn Ala Phe Ile Gln
                85                  90                  95 agt tta aaa gat gac cca agc caa agc gct aac ctt tta gca gaa gct     336
Ser Leu Lys Asp Asp Pro Ser Gln Ser Ala Asn Leu Leu Ala Glu Ala
            100                 105                 110 aaa aag cta aat gat gct cag gcg ccg aaa gta gac gcg aat tcg agc     384
```

```
                Lys Lys Leu Asn Asp Ala Gln Ala Pro Lys Val Asp Ala Asn Ser Ser
                    115                 120                 125 tcg gta ccc ggg gat ccg atg gcc ggg ttg ttg agc acc ttc gat aca         432
Ser Val Pro Gly Asp Pro Met Ala Gly Leu Leu Ser Thr Phe Asp Thr
    130                 135                 140 ttt agc tct agg agg agc gaa agt att aat aag tcg gga gga ggt gct         480
Phe Ser Ser Arg Arg Ser Glu Ser Ile Asn Lys Ser Gly Gly Gly Ala
145                 150                 155                 160 gtt atc ccc ggc cag agg agc aca gtc tca gtg ttc gta cta ggc cca         528
Val Ile Pro Gly Gln Arg Ser Thr Val Ser Val Phe Val Leu Gly Pro
                165                 170                 175 agt gtg act gat gat gca gac aag tta ttc att gca act acc ttc cta         576
Ser Val Thr Asp Asp Ala Asp Lys Leu Phe Ile Ala Thr Thr Phe Leu
            180                 185                 190 gct cac tca ttg gac aca gat aag cag cac tct cag aga gga ggg ttc         624
Ala His Ser Leu Asp Thr Asp Lys Gln His Ser Gln Arg Gly Gly Phe
        195                 200                 205 ctc gtc tct ctg ctt gcc atg gct tac agt agt cca gaa ttg tac ttg         672
Leu Val Ser Leu Leu Ala Met Ala Tyr Ser Ser Pro Glu Leu Tyr Leu
    210                 215                 220 aca aca aac gga gta aac gcc gat gtc aaa tat gtg atc tac aac ata         720
Thr Thr Asn Gly Val Asn Ala Asp Val Lys Tyr Val Ile Tyr Asn Ile
225                 230                 235                 240 gag aaa gac cct aag agg acg aag aca gac gga ttc att gtg aag acg         768
Glu Lys Asp Pro Lys Arg Thr Lys Thr Asp Gly Phe Ile Val Lys Thr
                245                 250                 255 aga gat atg gaa tat gag agg acc aca gaa tgg ctg ttt gga cct atg         816
Arg Asp Met Glu Tyr Glu Arg Thr Thr Glu Trp Leu Phe Gly Pro Met
            260                 265                 270 gtc aac aag agc cca ctc ttc cag ggt caa cgg gat gct gca gac cct         864
Val Asn Lys Ser Pro Leu Phe Gln Gly Gln Arg Asp Ala Ala Asp Pro
        275                 280                 285 gac aca ctc ctt caa atc tat ggg tat cct gca tgc cta gga gca ata         912
Asp Thr Leu Leu Gln Ile Tyr Gly Tyr Pro Ala Cys Leu Gly Ala Ile
    290                 295                 300 att gtc caa gtc tgg att gtg ctg gtg aag gcc atc aca agc agc gcc         960
Ile Val Gln Val Trp Ile Val Leu Val Lys Ala Ile Thr Ser Ser Ala
305                 310                 315                 320 ggc tta agg aaa ggg ttc ttc aac agg tta gag gcg ttc aga caa gac        1008
Gly Leu Arg Lys Gly Phe Phe Asn Arg Leu Glu Ala Phe Arg Gln Asp
                325                 330                 335 ggc acc gtg aaa ggt gcc tta gtt ttc act ggg gag aca gtt gag ggg        1056
Gly Thr Val Lys Gly Ala Leu Val Phe Thr Gly Glu Thr Val Glu Gly
            340                 345                 350 ata ggc tcg gtt atg aga tct cag caa agc ctt gta tct ctc atg gtt        1104
Ile Gly Ser Val Met Arg Ser Gln Gln Ser Leu Val Ser Leu Met Val
        355                 360                 365 gag acc ctt gtg act atg aat act gca aga tct gat ctc acc aca tta        1152
Glu Thr Leu Val Thr Met Asn Thr Ala Arg Ser Asp Leu Thr Thr Leu
    370                 375                 380 gag aag aac atc cag ata gtt tag                                        1176
Glu Lys Asn Ile Gln Ile Val
385                 390

<210> SEQ ID NO 17
<211> LENGTH: 391
<212> TYPE: PRT
<213> ORGANISM: Artificial
<220> FEATURE:
<223> OTHER INFORMATION: Fusion protein includes antibody binding amino
      acid sequence and Sendai virus nucleocapsid protein (ZZ-NPK3)
```

<400> SEQUENCE: 17

```
Met Glu His Asp Glu Ala Val Asp Asn Lys Phe Asn Lys Glu Gln Gln
 1               5                  10                  15

Asn Ala Phe Tyr Glu Ile Leu His Leu Pro Asn Leu Asn Glu Glu Gln
            20                  25                  30

Arg Asn Ala Phe Ile Gln Ser Leu Lys Asp Asp Pro Ser Gln Ser Ala
        35                  40                  45

Asn Leu Leu Ala Glu Ala Lys Lys Leu Asn Asp Ala Gln Ala Pro Lys
50                  55                  60

Val Asp Asn Lys Phe Asn Lys Glu Gln Gln Asn Ala Phe Tyr Glu Ile
65                  70                  75                  80

Leu His Leu Pro Asn Leu Asn Glu Glu Gln Arg Asn Ala Phe Ile Gln
                85                  90                  95

Ser Leu Lys Asp Asp Pro Ser Gln Ser Ala Asn Leu Leu Ala Glu Ala
            100                 105                 110

Lys Lys Leu Asn Asp Ala Gln Ala Pro Lys Val Asp Ala Asn Ser Ser
        115                 120                 125

Ser Val Pro Gly Asp Pro Met Ala Gly Leu Leu Ser Thr Phe Asp Thr
130                 135                 140

Phe Ser Ser Arg Arg Ser Glu Ser Ile Asn Lys Ser Gly Gly Gly Ala
145                 150                 155                 160

Val Ile Pro Gly Gln Arg Ser Thr Val Ser Val Phe Val Leu Gly Pro
                165                 170                 175

Ser Val Thr Asp Asp Ala Asp Lys Leu Phe Ile Ala Thr Thr Phe Leu
            180                 185                 190

Ala His Ser Leu Asp Thr Asp Lys Gln His Ser Gln Arg Gly Gly Phe
        195                 200                 205

Leu Val Ser Leu Leu Ala Met Ala Tyr Ser Ser Pro Glu Leu Tyr Leu
210                 215                 220

Thr Thr Asn Gly Val Asn Ala Asp Val Lys Tyr Val Ile Tyr Asn Ile
225                 230                 235                 240

Glu Lys Asp Pro Lys Arg Thr Lys Thr Asp Gly Phe Ile Val Lys Thr
                245                 250                 255

Arg Asp Met Glu Tyr Glu Arg Thr Thr Glu Trp Leu Phe Gly Pro Met
            260                 265                 270

Val Asn Lys Ser Pro Leu Phe Gln Gly Gln Arg Asp Ala Ala Asp Pro
        275                 280                 285

Asp Thr Leu Leu Gln Ile Tyr Gly Tyr Pro Ala Cys Leu Gly Ala Ile
290                 295                 300

Ile Val Gln Val Trp Ile Val Leu Val Lys Ala Ile Thr Ser Ser Ala
305                 310                 315                 320

Gly Leu Arg Lys Gly Phe Phe Asn Arg Leu Glu Ala Phe Arg Gln Asp
                325                 330                 335

Gly Thr Val Lys Gly Ala Leu Val Phe Thr Gly Glu Thr Val Glu Gly
            340                 345                 350

Ile Gly Ser Val Met Arg Ser Gln Gln Ser Leu Val Ser Leu Met Val
        355                 360                 365

Glu Thr Leu Val Thr Met Asn Thr Ala Arg Ser Asp Leu Thr Thr Leu
370                 375                 380

Glu Lys Asn Ile Gln Ile Val
385                 390
```

<210> SEQ ID NO 18
<211> LENGTH: 834

-continued

```
<212> TYPE: DNA
<213> ORGANISM: Artificial
<220> FEATURE:
<223> OTHER INFORMATION: Fusion protein includes antibody binding amino
      acid sequence and Sendai virus nucleocapsid protein (ZZ-NPK4)
<220> FEATURE:
<221> NAME/KEY: CDS
<222> LOCATION: (1)..(834)
<223> OTHER INFORMATION:

<400> SEQUENCE: 18 atg gaa cac gat gaa gcc gta gac aac aaa ttc aac aaa gaa caa caa        48
Met Glu His Asp Glu Ala Val Asp Asn Lys Phe Asn Lys Glu Gln Gln
1               5                   10                  15 aac gcg ttc tat gag atc tta cat tta cct aac tta aac gaa gaa caa        96
Asn Ala Phe Tyr Glu Ile Leu His Leu Pro Asn Leu Asn Glu Glu Gln
            20                  25                  30 cga aac gcc ttc atc caa agt tta aaa gat gac cca agc caa agc gct       144
Arg Asn Ala Phe Ile Gln Ser Leu Lys Asp Asp Pro Ser Gln Ser Ala
        35                  40                  45 aac ctt tta gca gaa gct aaa aag cta aat gat gct cag gcg ccg aaa       192
Asn Leu Leu Ala Glu Ala Lys Lys Leu Asn Asp Ala Gln Ala Pro Lys
    50                  55                  60 gta gac aac aaa ttc aac aaa gaa caa caa aac gcg ttc tat gag atc       240
Val Asp Asn Lys Phe Asn Lys Glu Gln Gln Asn Ala Phe Tyr Glu Ile
65                  70                  75                  80 tta cat tta cct aac tta aac gaa gaa caa cga aac gcc ttc atc caa       288
Leu His Leu Pro Asn Leu Asn Glu Glu Gln Arg Asn Ala Phe Ile Gln
                85                  90                  95 agt tta aaa gat gac cca agc caa agc gct aac ctt tta gca gaa gct       336
Ser Leu Lys Asp Asp Pro Ser Gln Ser Ala Asn Leu Leu Ala Glu Ala
            100                 105                 110 aaa aag cta aat gat gct cag gcg ccg aaa gta gac gcg aat tcg agc       384
Lys Lys Leu Asn Asp Ala Gln Ala Pro Lys Val Asp Ala Asn Ser Ser
        115                 120                 125 tcg gta ccc ggg gat ccg ggg aac tac atc cga gat gca ggg ctg gct       432
Ser Val Pro Gly Asp Pro Gly Asn Tyr Ile Arg Asp Ala Gly Leu Ala
    130                 135                 140 tcc ttc atg aac act att aaa tat ggg gtg gag aca aag atg gca gct       480
Ser Phe Met Asn Thr Ile Lys Tyr Gly Val Glu Thr Lys Met Ala Ala
145                 150                 155                 160 cta acg ttg tca aac ctg agg ccc gat att aat aag ctt aga agc ctc       528
Leu Thr Leu Ser Asn Leu Arg Pro Asp Ile Asn Lys Leu Arg Ser Leu
                165                 170                 175 ata gac acc tac ctg tca aaa ggc ccc aga gct ccc ttt atc tgt atc       576
Ile Asp Thr Tyr Leu Ser Lys Gly Pro Arg Ala Pro Phe Ile Cys Ile
            180                 185                 190 ctc aag gac cct gtt cat ggt gaa ttt gct cca ggc aat tat cct gca       624
Leu Lys Asp Pro Val His Gly Glu Phe Ala Pro Gly Asn Tyr Pro Ala
        195                 200                 205 cta tgg agt tac gcc atg gga gtc gcc gtc gta cag aac aag gca atg       672
Leu Trp Ser Tyr Ala Met Gly Val Ala Val Gln Asn Lys Ala Met
    210                 215                 220 cag cag tac gtc aca ggg agg aca tac ctt gat atg gaa atg ttc tta       720
Gln Gln Tyr Val Thr Gly Arg Thr Tyr Leu Asp Met Glu Met Phe Leu
225                 230                 235                 240 cta gga caa gcc gtg gca aag gat gct gaa tcg aag atc agc agt gcc       768
Leu Gly Gln Ala Val Ala Lys Asp Ala Glu Ser Lys Ile Ser Ser Ala
                245                 250                 255 ttg gaa gat gag tta gga gtg acg gat aca gcc aag ggg agg ctc aga       816
Leu Glu Asp Glu Leu Gly Val Thr Asp Thr Ala Lys Gly Arg Leu Arg
            260                 265                 270
```

```
cat cat ctg gca aac tag                                            834
His His Leu Ala Asn
        275

<210> SEQ ID NO 19
<211> LENGTH: 277
<212> TYPE: PRT
<213> ORGANISM: Artificial
<220> FEATURE:
<223> OTHER INFORMATION: Fusion protein includes antibody binding amino
      acid sequence and Sendai virus nucleocapsid protein (ZZ-NPK4)

<400> SEQUENCE: 19

Met Glu His Asp Glu Ala Val Asp Asn Lys Phe Asn Lys Glu Gln Gln
1               5                   10                  15

Asn Ala Phe Tyr Glu Ile Leu His Leu Pro Asn Leu Asn Glu Glu Gln
            20                  25                  30

Arg Asn Ala Phe Ile Gln Ser Leu Lys Asp Asp Pro Ser Gln Ser Ala
        35                  40                  45

Asn Leu Leu Ala Glu Ala Lys Lys Leu Asn Asp Ala Gln Ala Pro Lys
50                  55                  60

Val Asp Asn Lys Phe Asn Lys Glu Gln Gln Asn Ala Phe Tyr Glu Ile
65                  70                  75                  80

Leu His Leu Pro Asn Leu Asn Glu Glu Gln Arg Asn Ala Phe Ile Gln
                85                  90                  95

Ser Leu Lys Asp Asp Pro Ser Gln Ser Ala Asn Leu Leu Ala Glu Ala
            100                 105                 110

Lys Lys Leu Asn Asp Ala Gln Ala Pro Lys Val Asp Ala Asn Ser Ser
        115                 120                 125

Ser Val Pro Gly Asp Pro Gly Asn Tyr Ile Arg Asp Ala Gly Leu Ala
130                 135                 140

Ser Phe Met Asn Thr Ile Lys Tyr Gly Val Glu Thr Lys Met Ala Ala
145                 150                 155                 160

Leu Thr Leu Ser Asn Leu Arg Pro Asp Ile Asn Lys Leu Arg Ser Leu
                165                 170                 175

Ile Asp Thr Tyr Leu Ser Lys Gly Pro Arg Ala Pro Phe Ile Cys Ile
            180                 185                 190

Leu Lys Asp Pro Val His Gly Glu Phe Ala Pro Gly Asn Tyr Pro Ala
        195                 200                 205

Leu Trp Ser Tyr Ala Met Gly Val Ala Val Val Gln Asn Lys Ala Met
210                 215                 220

Gln Gln Tyr Val Thr Gly Arg Thr Tyr Leu Asp Met Glu Met Phe Leu
225                 230                 235                 240

Leu Gly Gln Ala Val Ala Lys Asp Ala Glu Ser Lys Ile Ser Ser Ala
                245                 250                 255

Leu Glu Asp Glu Leu Gly Val Thr Asp Thr Ala Lys Gly Arg Leu Arg
            260                 265                 270

His His Leu Ala Asn
        275

<210> SEQ ID NO 20
<211> LENGTH: 18
<212> TYPE: DNA
<213> ORGANISM: Artificial
<220> FEATURE:
<223> OTHER INFORMATION: Oligonucleotide to act as a primer for PCR

<400> SEQUENCE: 20
tagctcgagc accaccac                                                 18
```

-continued

```
<210> SEQ ID NO 21
<211> LENGTH: 18
<212> TYPE: DNA
<213> ORGANISM: Artificial
<220> FEATURE:
<223> OTHER INFORMATION: Oligonucleotide to act as a primer for PCR

<400> SEQUENCE: 21
gtttgccaga tgatgtct                                                      18

<210> SEQ ID NO 22
<211> LENGTH: 18
<212> TYPE: DNA
<213> ORGANISM: Artificial
<220> FEATURE:
<223> OTHER INFORMATION: Oligonucleotide to act as a primer for PCR

<400> SEQUENCE: 22
aaggtatgtc ctccctgt                                                      18

<210> SEQ ID NO 23
<211> LENGTH: 18
<212> TYPE: DNA
<213> ORGANISM: Artificial
<220> FEATURE:
<223> OTHER INFORMATION: Oligonucleotide to act as a primer for PCR

<400> SEQUENCE: 23
aactatctgg atgttctt                                                      18

<210> SEQ ID NO 24
<211> LENGTH: 27
<212> TYPE: DNA
<213> ORGANISM: Artificial
<220> FEATURE:
<223> OTHER INFORMATION: Oligonucleotide to act as a primer for PCR

<400> SEQUENCE: 24
cggatccccg ggtaccgagc tcgaatt                                            27

<210> SEQ ID NO 25
<211> LENGTH: 22
<212> TYPE: DNA
<213> ORGANISM: Artificial
<220> FEATURE:
<223> OTHER INFORMATION: Oligonucleotide to act as a primer for PCR

<400> SEQUENCE: 25
gggaactaca tccgagatgc ag                                                 22

<210> SEQ ID NO 26
<211> LENGTH: 1203
<212> TYPE: DNA
<213> ORGANISM: Artificial
<220> FEATURE:
<223> OTHER INFORMATION: Sendai virus nucleocapsid protein (NPK1)
<220> FEATURE:
<221> NAME/KEY: CDS
<222> LOCATION: (1)..(1203)
<223> OTHER INFORMATION:

<400> SEQUENCE: 26 atg gcc ggg ttg ttg agc acc ttc gat aca ttt agc tct agg agg agc         48
Met Ala Gly Leu Leu Ser Thr Phe Asp Thr Phe Ser Ser Arg Arg Ser
1               5                   10                  15 gaa agt att aat aag tcg gga gga ggt gct gtt atc ccc ggc cag agg         96
```

-continued

| | | |
|---|---|---|
| Glu Ser Ile Asn Lys Ser Gly Gly Ala Val Ile Pro Gly Gln Arg<br>20                 25                  30 | | |
| agc aca gtc tca gtg ttc gta cta ggc cca agt gtg act gat gat gca<br>Ser Thr Val Ser Val Phe Val Leu Gly Pro Ser Val Thr Asp Asp Ala<br>        35                40                45 | 144 | |
| gac aag tta ttc att gca act acc ttc cta gct cac tca ttg gac aca<br>Asp Lys Leu Phe Ile Ala Thr Thr Phe Leu Ala His Ser Leu Asp Thr<br>50                 55                60 | 192 | |
| gat aag cag cac tct cag aga gga ggg ttc ctc gtc tct ctg ctt gcc<br>Asp Lys Gln His Ser Gln Arg Gly Gly Phe Leu Val Ser Leu Leu Ala<br>65                 70               75               80 | 240 | |
| atg gct tac agt agt cca gaa ttg tac ttg aca aca aac gga gta aac<br>Met Ala Tyr Ser Ser Pro Glu Leu Tyr Leu Thr Thr Asn Gly Val Asn<br>              85                90                95 | 288 | |
| gcc gat gtc aaa tat gtg atc tac aac ata gag aaa gac cct aag agg<br>Ala Asp Val Lys Tyr Val Ile Tyr Asn Ile Glu Lys Asp Pro Lys Arg<br>        100                  105              110 | 336 | |
| acg aag aca gac gga ttc att gtg aag acg aga gat atg gaa tat gag<br>Thr Lys Thr Asp Gly Phe Ile Val Lys Thr Arg Asp Met Glu Tyr Glu<br>        115                  120              125 | 384 | |
| agg acc aca gaa tgg ctg ttt gga cct atg gtc aac aag agc cca ctc<br>Arg Thr Thr Glu Trp Leu Phe Gly Pro Met Val Asn Lys Ser Pro Leu<br>130                  135                140 | 432 | |
| ttc cag ggt caa cgg gat gct gca gac cct gac aca ctc ctt caa atc<br>Phe Gln Gly Gln Arg Asp Ala Ala Asp Pro Asp Thr Leu Leu Gln Ile<br>145                  150                155              160 | 480 | |
| tat ggg tat cct gca tgc cta gga gca ata att gtc caa gtc tgg att<br>Tyr Gly Tyr Pro Ala Cys Leu Gly Ala Ile Ile Val Gln Val Trp Ile<br>                  165                170              175 | 528 | |
| gtg ctg gtg aag gcc atc aca agc agc gcc ggc tta agg aaa ggg ttc<br>Val Leu Val Lys Ala Ile Thr Ser Ser Ala Gly Leu Arg Lys Gly Phe<br>        180                  185              190 | 576 | |
| ttc aac agg tta gag gcg ttc aga caa gac ggc acc gtg aaa ggt gcc<br>Phe Asn Arg Leu Glu Ala Phe Arg Gln Asp Gly Thr Val Lys Gly Ala<br>        195                  200              205 | 624 | |
| tta gtt ttc act ggg gag aca gtt gag ggg ata ggc tcg gtt atg aga<br>Leu Val Phe Thr Gly Glu Thr Val Glu Gly Ile Gly Ser Val Met Arg<br>210                  215                220 | 672 | |
| tct cag caa agc ctt gta tct ctc atg gtt gag acc ctt gtg act atg<br>Ser Gln Gln Ser Leu Val Ser Leu Met Val Glu Thr Leu Val Thr Met<br>225                  230                235              240 | 720 | |
| aat act gca aga tct gat ctc acc aca tta gag aag aac atc cag atc<br>Asn Thr Ala Arg Ser Asp Leu Thr Thr Leu Glu Lys Asn Ile Gln Ile<br>                  245                250              255 | 768 | |
| gtt ggg aac tac atc cga gat gca ggg ctg gct tcc ttc atg aac act<br>Val Gly Asn Tyr Ile Arg Asp Ala Gly Leu Ala Ser Phe Met Asn Thr<br>        260                  265              270 | 816 | |
| att aaa tat ggg gtg gag aca aag atg gca gct cta acg ttg tca aac<br>Ile Lys Tyr Gly Val Glu Thr Lys Met Ala Ala Leu Thr Leu Ser Asn<br>        275                  280              285 | 864 | |
| ctg agg ccc gat att aat aag ctt aga agc ctc ata gac acc tac ctg<br>Leu Arg Pro Asp Ile Asn Lys Leu Arg Ser Leu Ile Asp Thr Tyr Leu<br>290                  295                300 | 912 | |
| tca aaa ggc ccc aga gct ccc ttt atc tgt atc ctc aag gac cct gtt<br>Ser Lys Gly Pro Arg Ala Pro Phe Ile Cys Ile Leu Lys Asp Pro Val<br>305                  310                315              320 | 960 | |
| cat ggt gaa ttt gct cca ggc aat tat cct gca cta tgg agt tac gcc<br>His Gly Glu Phe Ala Pro Gly Asn Tyr Pro Ala Leu Trp Ser Tyr Ala<br>                  325                330              335 | 1008 | |
| atg gga gtc gcc gtc gta cag aac aag gca atg cag cag tac gtc aca | 1056 | |

```
                Met Gly Val Ala Val Gln Asn Lys Ala Met Gln Gln Tyr Val Thr
                    340                 345                 350 ggg agg aca tac ctt gat atg gaa atg ttc tta cta gga caa gcc gtg          1104
Gly Arg Thr Tyr Leu Asp Met Glu Met Phe Leu Leu Gly Gln Ala Val
        355                 360                 365 gca aag gat gct gaa tcg aag atc agc agt gcc ttg gaa gat gag tta          1152
Ala Lys Asp Ala Glu Ser Lys Ile Ser Ser Ala Leu Glu Asp Glu Leu
370                 375                 380 gga gtg acg gat aca gcc aag ggg agg ctc aga cat cat ctg gca aac          1200
Gly Val Thr Asp Thr Ala Lys Gly Arg Leu Arg His His Leu Ala Asn
385                 390                 395                 400 tag                                                                       1203

<210> SEQ ID NO 27
<211> LENGTH: 400
<212> TYPE: PRT
<213> ORGANISM: Artificial
<220> FEATURE:
<223> OTHER INFORMATION: Sendai virus nucleocapsid protein (NPK1)

<400> SEQUENCE: 27

Met Ala Gly Leu Leu Ser Thr Phe Asp Thr Phe Ser Ser Arg Arg Ser
1               5                   10                  15

Glu Ser Ile Asn Lys Ser Gly Gly Ala Val Ile Pro Gly Gln Arg
            20                  25                  30

Ser Thr Val Ser Val Phe Val Leu Gly Pro Ser Val Thr Asp Asp Ala
        35                  40                  45

Asp Lys Leu Phe Ile Ala Thr Thr Phe Leu Ala His Ser Leu Asp Thr
    50                  55                  60

Asp Lys Gln His Ser Gln Arg Gly Gly Phe Leu Val Ser Leu Leu Ala
65                  70                  75                  80

Met Ala Tyr Ser Ser Pro Glu Leu Tyr Leu Thr Thr Asn Gly Val Asn
                85                  90                  95

Ala Asp Val Lys Tyr Val Ile Tyr Asn Ile Glu Lys Asp Pro Lys Arg
            100                 105                 110

Thr Lys Thr Asp Gly Phe Ile Val Lys Thr Arg Asp Met Glu Tyr Glu
        115                 120                 125

Arg Thr Thr Glu Trp Leu Phe Gly Pro Met Val Asn Lys Ser Pro Leu
    130                 135                 140

Phe Gln Gly Gln Arg Asp Ala Ala Asp Pro Asp Thr Leu Leu Gln Ile
145                 150                 155                 160

Tyr Gly Tyr Pro Ala Cys Leu Gly Ala Ile Ile Val Gln Val Trp Ile
                165                 170                 175

Val Leu Val Lys Ala Ile Thr Ser Ser Ala Gly Leu Arg Lys Gly Phe
            180                 185                 190

Phe Asn Arg Leu Glu Ala Phe Arg Gln Asp Gly Thr Val Lys Gly Ala
        195                 200                 205

Leu Val Phe Thr Gly Glu Thr Val Glu Gly Ile Gly Ser Val Met Arg
    210                 215                 220

Ser Gln Gln Ser Leu Val Ser Leu Met Val Glu Thr Leu Val Thr Met
225                 230                 235                 240

Asn Thr Ala Arg Ser Asp Leu Thr Thr Leu Glu Lys Asn Ile Gln Ile
                245                 250                 255

Val Gly Asn Tyr Ile Arg Asp Ala Gly Leu Ala Ser Phe Met Asn Thr
            260                 265                 270

Ile Lys Tyr Gly Val Glu Thr Lys Met Ala Ala Leu Thr Leu Ser Asn
        275                 280                 285
```

```
Leu Arg Pro Asp Ile Asn Lys Leu Arg Ser Leu Ile Asp Thr Tyr Leu
        290                 295                 300

Ser Lys Gly Pro Arg Ala Pro Phe Ile Cys Ile Leu Lys Asp Pro Val
305                 310                 315                 320

His Gly Glu Phe Ala Pro Gly Asn Tyr Pro Ala Leu Trp Ser Tyr Ala
            325                 330                 335

Met Gly Val Ala Val Val Gln Asn Lys Ala Met Gln Gln Tyr Val Thr
        340                 345                 350

Gly Arg Thr Tyr Leu Asp Met Glu Met Phe Leu Leu Gly Gln Ala Val
            355                 360                 365

Ala Lys Asp Ala Glu Ser Lys Ile Ser Ser Ala Leu Glu Asp Glu Leu
        370                 375                 380

Gly Val Thr Asp Thr Ala Lys Gly Arg Leu Arg His His Leu Ala Asn
385                 390                 395                 400

<210> SEQ ID NO 28
<211> LENGTH: 1074
<212> TYPE: DNA
<213> ORGANISM: Artificial
<220> FEATURE:
<223> OTHER INFORMATION: Sendai virus nucleocapsid protein (NPK2)
<220> FEATURE:
<221> NAME/KEY: CDS
<222> LOCATION: (1)..(1074)
<223> OTHER INFORMATION:

<400> SEQUENCE: 28 atg gcc ggg ttg ttg agc acc ttc gat aca ttt agc tct agg agg agc      48
Met Ala Gly Leu Leu Ser Thr Phe Asp Thr Phe Ser Ser Arg Arg Ser
1               5                   10                  15 gaa agt att aat aag tcg gga gga ggt gct gtt atc ccc ggc cag agg      96
Glu Ser Ile Asn Lys Ser Gly Gly Gly Ala Val Ile Pro Gly Gln Arg
            20                  25                  30 agc aca gtc tca gtg ttc gta cta ggc cca agt gtg act gat gat gca    144
Ser Thr Val Ser Val Phe Val Leu Gly Pro Ser Val Thr Asp Asp Ala
        35                  40                  45 gac aag tta ttc att gca act acc ttc cta gct cac tca ttg gac aca    192
Asp Lys Leu Phe Ile Ala Thr Thr Phe Leu Ala His Ser Leu Asp Thr
50                  55                  60 gat aag cag cac tct cag aga gga ggg ttc ctc gtc tct ctg ctt gcc    240
Asp Lys Gln His Ser Gln Arg Gly Gly Phe Leu Val Ser Leu Leu Ala
65                  70                  75                  80 atg gct tac agt agt cca gaa ttg tac ttg aca aca aac gga gta aac    288
Met Ala Tyr Ser Ser Pro Glu Leu Tyr Leu Thr Thr Asn Gly Val Asn
                85                  90                  95 gcc gat gtc aaa tat gtg atc tac aac ata gag aaa gac cct aag agg    336
Ala Asp Val Lys Tyr Val Ile Tyr Asn Ile Glu Lys Asp Pro Lys Arg
            100                 105                 110 acg aag aca gac gga ttc att gtg aag acg aga gat atg gaa tat gag    384
Thr Lys Thr Asp Gly Phe Ile Val Lys Thr Arg Asp Met Glu Tyr Glu
        115                 120                 125 agg acc aca gaa tgg ctg ttt gga cct atg gtc aac aag agc cca ctc    432
Arg Thr Thr Glu Trp Leu Phe Gly Pro Met Val Asn Lys Ser Pro Leu
    130                 135                 140 ttc cag ggt caa cgg gat gct gca gac cct gac aca ctc ctt caa atc    480
Phe Gln Gly Gln Arg Asp Ala Ala Asp Pro Asp Thr Leu Leu Gln Ile
145                 150                 155                 160 tat ggg tat cct gca tgc cta gga gca ata att gtc caa gtc tgg att    528
Tyr Gly Tyr Pro Ala Cys Leu Gly Ala Ile Ile Val Gln Val Trp Ile
                165                 170                 175
```

```
gtg ctg gtg aag gcc atc aca agc agc gcc ggc tta agg aaa ggg ttc       576
Val Leu Val Lys Ala Ile Thr Ser Ser Ala Gly Leu Arg Lys Gly Phe
            180                 185                 190 ttc aac agg tta gag gcg ttc aga caa gac ggc acc gtg aaa ggt gcc       624
Phe Asn Arg Leu Glu Ala Phe Arg Gln Asp Gly Thr Val Lys Gly Ala
        195                 200                 205 tta gtt ttc act ggg gag aca gtt gag ggg ata ggc tcg gtt atg aga       672
Leu Val Phe Thr Gly Glu Thr Val Glu Gly Ile Gly Ser Val Met Arg
    210                 215                 220 tct cag caa agc ctt gta tct ctc atg gtt gag acc ctt gtg act atg       720
Ser Gln Gln Ser Leu Val Ser Leu Met Val Glu Thr Leu Val Thr Met
225                 230                 235                 240 aat act gca aga tct gat ctc acc aca tta gag aag aac atc cag atc       768
Asn Thr Ala Arg Ser Asp Leu Thr Thr Leu Glu Lys Asn Ile Gln Ile
                245                 250                 255 gtt ggg aac tac atc cga gat gca ggg ctg gct tcc ttc atg aac act       816
Val Gly Asn Tyr Ile Arg Asp Ala Gly Leu Ala Ser Phe Met Asn Thr
            260                 265                 270 att aaa tat ggg gtg gag aca aag atg gca gct cta acg ttg tca aac       864
Ile Lys Tyr Gly Val Glu Thr Lys Met Ala Ala Leu Thr Leu Ser Asn
        275                 280                 285 ctg agg ccc gat att aat aag ctt aga agc ctc ata gac acc tac ctg       912
Leu Arg Pro Asp Ile Asn Lys Leu Arg Ser Leu Ile Asp Thr Tyr Leu
    290                 295                 300 tca aaa ggc ccc aga gct ccc ttt atc tgt atc ctc aag gac cct gtt       960
Ser Lys Gly Pro Arg Ala Pro Phe Ile Cys Ile Leu Lys Asp Pro Val
305                 310                 315                 320 cat ggt gaa ttt gct cca ggc aat tat cct gca cta tgg agt tac gcc      1008
His Gly Glu Phe Ala Pro Gly Asn Tyr Pro Ala Leu Trp Ser Tyr Ala
                325                 330                 335 atg gga gtc gcc gtc gta cag aac aag gca atg cag cag tac gtc aca      1056
Met Gly Val Ala Val Val Gln Asn Lys Ala Met Gln Gln Tyr Val Thr
            340                 345                 350 ggg agg aca tac ctt tag                                              1074
Gly Arg Thr Tyr Leu
        355

<210> SEQ ID NO 29
<211> LENGTH: 357
<212> TYPE: PRT
<213> ORGANISM: Artificial
<220> FEATURE:
<223> OTHER INFORMATION: Sendai virus nucleocapsid protein (NPK2)

<400> SEQUENCE: 29

Met Ala Gly Leu Leu Ser Thr Phe Asp Thr Phe Ser Ser Arg Arg Ser
1               5                   10                  15

Glu Ser Ile Asn Lys Ser Gly Gly Gly Ala Val Ile Pro Gly Gln Arg
            20                  25                  30

Ser Thr Val Ser Val Phe Val Leu Gly Pro Ser Val Thr Asp Asp Ala
        35                  40                  45

Asp Lys Leu Phe Ile Ala Thr Thr Phe Leu Ala His Ser Leu Asp Thr
    50                  55                  60

Asp Lys Gln His Ser Gln Arg Gly Gly Phe Leu Val Ser Leu Leu Ala
65                  70                  75                  80

Met Ala Tyr Ser Ser Pro Glu Leu Tyr Leu Thr Thr Asn Gly Val Asn
                85                  90                  95

Ala Asp Val Lys Tyr Val Ile Tyr Asn Ile Glu Lys Asp Pro Lys Arg
            100                 105                 110

Thr Lys Thr Asp Gly Phe Ile Val Lys Thr Arg Asp Met Glu Tyr Glu
```

```
                    115                 120                 125
Arg Thr Thr Glu Trp Leu Phe Gly Pro Met Val Asn Lys Ser Pro Leu
    130                 135                 140

Phe Gln Gly Gln Arg Asp Ala Ala Asp Pro Asp Thr Leu Leu Gln Ile
145                 150                 155                 160

Tyr Gly Tyr Pro Ala Cys Leu Gly Ala Ile Ile Val Gln Val Trp Ile
                165                 170                 175

Val Leu Val Lys Ala Ile Thr Ser Ser Ala Gly Leu Arg Lys Gly Phe
            180                 185                 190

Phe Asn Arg Leu Glu Ala Phe Arg Gln Asp Gly Thr Val Lys Gly Ala
        195                 200                 205

Leu Val Phe Thr Gly Glu Thr Val Glu Gly Ile Gly Ser Val Met Arg
    210                 215                 220

Ser Gln Gln Ser Leu Val Ser Leu Met Val Glu Thr Leu Val Thr Met
225                 230                 235                 240

Asn Thr Ala Arg Ser Asp Leu Thr Thr Leu Glu Lys Asn Ile Gln Ile
                245                 250                 255

Val Gly Asn Tyr Ile Arg Asp Ala Gly Leu Ala Ser Phe Met Asn Thr
            260                 265                 270

Ile Lys Tyr Gly Val Glu Thr Lys Met Ala Ala Leu Thr Leu Ser Asn
        275                 280                 285

Leu Arg Pro Asp Ile Asn Lys Leu Arg Ser Leu Ile Asp Thr Tyr Leu
    290                 295                 300

Ser Lys Gly Pro Arg Ala Pro Phe Ile Cys Ile Leu Lys Asp Pro Val
305                 310                 315                 320

His Gly Glu Phe Ala Pro Gly Asn Tyr Pro Ala Leu Trp Ser Tyr Ala
                325                 330                 335

Met Gly Val Ala Val Gln Asn Lys Ala Met Gln Gln Tyr Val Thr
            340                 345                 350

Gly Arg Thr Tyr Leu
        355

<210> SEQ ID NO 30
<211> LENGTH: 774
<212> TYPE: DNA
<213> ORGANISM: Artificial
<220> FEATURE:
<223> OTHER INFORMATION: Sendai virus nucleocapsid protein (NPK3)
<220> FEATURE:
<221> NAME/KEY: CDS
<222> LOCATION: (1)..(774)
<223> OTHER INFORMATION:

<400> SEQUENCE: 30 atg gcc ggg ttg ttg agc acc ttc gat aca ttt agc tct agg agg agc     48
Met Ala Gly Leu Leu Ser Thr Phe Asp Thr Phe Ser Ser Arg Arg Ser
1               5                   10                  15 gaa agt att aat aag tcg gga gga ggt gct gtt atc ccc ggc cag agg     96
Glu Ser Ile Asn Lys Ser Gly Gly Gly Ala Val Ile Pro Gly Gln Arg
            20                  25                  30 agc aca gtc tca gtg ttc gta cta ggc cca agt gtg act gat gat gca    144
Ser Thr Val Ser Val Phe Val Leu Gly Pro Ser Val Thr Asp Asp Ala
        35                  40                  45 gac aag tta ttc att gca act acc ttc cta gct cac tca ttg gac aca    192
Asp Lys Leu Phe Ile Ala Thr Thr Phe Leu Ala His Ser Leu Asp Thr
    50                  55                  60 gat aag cag cac tct cag aga gga ggg ttc ctc gtc tct ctg ctt gcc    240
Asp Lys Gln His Ser Gln Arg Gly Gly Phe Leu Val Ser Leu Leu Ala
65                  70                  75                  80
```

-continued

| | | |
|---|---|---|
| atg gct tac agt agt cca gaa ttg tac ttg aca aca aac gga gta aac<br>Met Ala Tyr Ser Ser Pro Glu Leu Tyr Leu Thr Thr Asn Gly Val Asn<br>                85                    90                    95 | | 288 |
| gcc gat gtc aaa tat gtg atc tac aac ata gag aaa gac cct aag agg<br>Ala Asp Val Lys Tyr Val Ile Tyr Asn Ile Glu Lys Asp Pro Lys Arg<br>            100                    105                  110 | | 336 |
| acg aag aca gac gga ttc att gtg aag acg aga gat atg gaa tat gag<br>Thr Lys Thr Asp Gly Phe Ile Val Lys Thr Arg Asp Met Glu Tyr Glu<br>            115                    120                  125 | | 384 |
| agg acc aca gaa tgg ctg ttt gga cct atg gtc aac aag agc cca ctc<br>Arg Thr Thr Glu Trp Leu Phe Gly Pro Met Val Asn Lys Ser Pro Leu<br>130                    135                    140 | | 432 |
| ttc cag ggt caa cgg gat gct gca gac cct gac aca ctc ctt caa atc<br>Phe Gln Gly Gln Arg Asp Ala Ala Asp Pro Asp Thr Leu Leu Gln Ile<br>145                    150                    155                  160 | | 480 |
| tat ggg tat cct gca tgc cta gga gca ata att gtc caa gtc tgg att<br>Tyr Gly Tyr Pro Ala Cys Leu Gly Ala Ile Ile Val Gln Val Trp Ile<br>                  165                    170                  175 | | 528 |
| gtg ctg gtg aag gcc atc aca agc agc gcc ggc tta agg aaa ggg ttc<br>Val Leu Val Lys Ala Ile Thr Ser Ser Ala Gly Leu Arg Lys Gly Phe<br>            180                    185                  190 | | 576 |
| ttc aac agg tta gag gcg ttc aga caa gac ggc acc gtg aaa ggt gcc<br>Phe Asn Arg Leu Glu Ala Phe Arg Gln Asp Gly Thr Val Lys Gly Ala<br>                  195                    200                  205 | | 624 |
| tta gtt ttc act ggg gag aca gtt gag ggg ata ggc tcg gtt atg aga<br>Leu Val Phe Thr Gly Glu Thr Val Glu Gly Ile Gly Ser Val Met Arg<br>            210                    215                  220 | | 672 |
| tct cag caa agc ctt gta tct ctc atg gtt gag acc ctt gtg act atg<br>Ser Gln Gln Ser Leu Val Ser Leu Met Val Glu Thr Leu Val Thr Met<br>225                    230                    235                  240 | | 720 |
| aat act gca aga tct gat ctc acc aca tta gag aag aac atc cag ata<br>Asn Thr Ala Arg Ser Asp Leu Thr Thr Leu Glu Lys Asn Ile Gln Ile<br>                  245                    250                  255 | | 768 |
| gtt tag<br>Val | | 774 |

<210> SEQ ID NO 31
<211> LENGTH: 257
<212> TYPE: PRT
<213> ORGANISM: Artificial
<220> FEATURE:
<223> OTHER INFORMATION: Sendai virus nucleocapsid protein (NPK3)

<400> SEQUENCE: 31

Met Ala Gly Leu Leu Ser Thr Phe Asp Thr Phe Ser Ser Arg Arg Ser
1               5                   10                  15

Glu Ser Ile Asn Lys Ser Gly Gly Gly Ala Val Ile Pro Gly Gln Arg
            20                  25                  30

Ser Thr Val Ser Val Phe Val Leu Gly Pro Ser Val Thr Asp Asp Ala
        35                  40                  45

Asp Lys Leu Phe Ile Ala Thr Thr Phe Leu Ala His Ser Leu Asp Thr
    50                  55                  60

Asp Lys Gln His Ser Gln Arg Gly Gly Phe Leu Val Ser Leu Leu Ala
65                  70                  75                  80

Met Ala Tyr Ser Ser Pro Glu Leu Tyr Leu Thr Thr Asn Gly Val Asn
                85                  90                  95

Ala Asp Val Lys Tyr Val Ile Tyr Asn Ile Glu Lys Asp Pro Lys Arg
            100                 105                 110

Thr Lys Thr Asp Gly Phe Ile Val Lys Thr Arg Asp Met Glu Tyr Glu

```
              115                 120                 125
Arg Thr Thr Glu Trp Leu Phe Gly Pro Met Val Asn Lys Ser Pro Leu
130                 135                 140

Phe Gln Gly Gln Arg Asp Ala Ala Asp Pro Asp Thr Leu Leu Gln Ile
145                 150                 155                 160

Tyr Gly Tyr Pro Ala Cys Leu Gly Ala Ile Ile Val Gln Val Trp Ile
                165                 170                 175

Val Leu Val Lys Ala Ile Thr Ser Ser Ala Gly Leu Arg Lys Gly Phe
            180                 185                 190

Phe Asn Arg Leu Glu Ala Phe Arg Gln Asp Gly Thr Val Lys Gly Ala
        195                 200                 205

Leu Val Phe Thr Gly Glu Thr Val Glu Gly Ile Gly Ser Val Met Arg
    210                 215                 220

Ser Gln Gln Ser Leu Val Ser Leu Met Val Glu Thr Leu Val Thr Met
225                 230                 235                 240

Asn Thr Ala Arg Ser Asp Leu Thr Thr Leu Glu Lys Asn Ile Gln Ile
                245                 250                 255

Val

<210> SEQ ID NO 32
<211> LENGTH: 432
<212> TYPE: DNA
<213> ORGANISM: Artificial
<220> FEATURE:
<223> OTHER INFORMATION: Sendai virus nucleocapsid protein (NPK4)
<220> FEATURE:
<221> NAME/KEY: CDS
<222> LOCATION: (1)..(432)
<223> OTHER INFORMATION:

<400> SEQUENCE: 32 ggg aac tac atc cga gat gca ggg ctg gct tcc ttc atg aac act att    48
Gly Asn Tyr Ile Arg Asp Ala Gly Leu Ala Ser Phe Met Asn Thr Ile
1               5                   10                  15 aaa tat ggg gtg gag aca aag atg gca gct cta acg ttg tca aac ctg    96
Lys Tyr Gly Val Glu Thr Lys Met Ala Ala Leu Thr Leu Ser Asn Leu
            20                  25                  30 agg ccc gat att aat aag ctt aga agc ctc ata gac acc tac ctg tca   144
Arg Pro Asp Ile Asn Lys Leu Arg Ser Leu Ile Asp Thr Tyr Leu Ser
        35                  40                  45 aaa ggc ccc aga gct ccc ttt atc tgt atc ctc aag gac cct gtt cat   192
Lys Gly Pro Arg Ala Pro Phe Ile Cys Ile Leu Lys Asp Pro Val His
    50                  55                  60 ggt gaa ttt gct cca ggc aat tat cct gca cta tgg agt tac gcc atg   240
Gly Glu Phe Ala Pro Gly Asn Tyr Pro Ala Leu Trp Ser Tyr Ala Met
65                  70                  75                  80 gga gtc gcc gtc gta cag aac aag gca atg cag cag tac gtc aca ggg   288
Gly Val Ala Val Val Gln Asn Lys Ala Met Gln Gln Tyr Val Thr Gly
                85                  90                  95 aga aca tac ctt gat atg gaa atg ttc tta cta gga caa gcc gtg gca   336
Arg Thr Tyr Leu Asp Met Glu Met Phe Leu Leu Gly Gln Ala Val Ala
            100                 105                 110 aag gat gct gaa tcg aag atc agc agt gcc ttg gaa gat gag tta gga   384
Lys Asp Ala Glu Ser Lys Ile Ser Ser Ala Leu Glu Asp Glu Leu Gly
        115                 120                 125 gtg acg gat aca gcc aag ggg agg ctc aga cat cat ctg gca aac tag   432
Val Thr Asp Thr Ala Lys Gly Arg Leu Arg His His Leu Ala Asn
    130                 135                 140

<210> SEQ ID NO 33
```

```
<211> LENGTH: 143
<212> TYPE: PRT
<213> ORGANISM: Artificial
<220> FEATURE:
<223> OTHER INFORMATION: Sendai virus nucleocapsid protein (NPK4)

<400> SEQUENCE: 33

Gly Asn Tyr Ile Arg Asp Ala Gly Leu Ala Ser Phe Met Asn Thr Ile
1               5                   10                  15

Lys Tyr Gly Val Glu Thr Lys Met Ala Ala Leu Thr Leu Ser Asn Leu
            20                  25                  30

Arg Pro Asp Ile Asn Lys Leu Arg Ser Leu Ile Asp Thr Tyr Leu Ser
        35                  40                  45

Lys Gly Pro Arg Ala Pro Phe Ile Cys Ile Leu Lys Asp Pro Val His
    50                  55                  60

Gly Glu Phe Ala Pro Gly Asn Tyr Pro Ala Leu Trp Ser Tyr Ala Met
65                  70                  75                  80

Gly Val Ala Val Gln Asn Lys Ala Met Gln Gln Tyr Val Thr Gly
                85                  90                  95

Arg Thr Tyr Leu Asp Met Glu Met Phe Leu Leu Gly Gln Ala Val Ala
            100                 105                 110

Lys Asp Ala Glu Ser Lys Ile Ser Ser Ala Leu Glu Asp Glu Leu Gly
        115                 120                 125

Val Thr Asp Thr Ala Lys Gly Arg Leu Arg His His Leu Ala Asn
    130                 135                 140

<210> SEQ ID NO 34
<211> LENGTH: 69
<212> TYPE: DNA
<213> ORGANISM: Artificial
<220> FEATURE:
<223> OTHER INFORMATION: Oligonucleotide to act as a primer for PCR

<400> SEQUENCE: 34
gaagcggttg atgctgctac cgcagaaaaa gttttcaaac agtacgctaa cagcatgact      60
ggtggacag                                                              69

<210> SEQ ID NO 35
<211> LENGTH: 69
<212> TYPE: DNA
<213> ORGANISM: Artificial
<220> FEATURE:
<223> OTHER INFORMATION: Oligonucleotide to act as a primer for PCR

<400> SEQUENCE: 35
agtagtggtt tcgcctttca aggttttacc attcaggatt aatttgtagg tcatggtata      60
tctccttct                                                              69

<210> SEQ ID NO 36
<211> LENGTH: 72
<212> TYPE: DNA
<213> ORGANISM: Artificial
<220> FEATURE:
<223> OTHER INFORMATION: Oligonucleotide to act as a primer for PCR

<400> SEQUENCE: 36
gttactgaaa aaccggaagt gatcgatgcg tctgaattaa ccccggcggt gaccctgaga      60
tccggctgct aa                                                          72

<210> SEQ ID NO 37
<211> LENGTH: 72
```

```
<212> TYPE: DNA
<213> ORGANISM: Artificial
<220> FEATURE:
<223> OTHER INFORMATION: Oligonucleotide to act as a primer for PCR

<400> SEQUENCE: 37
ggtaaaggtt ttagtcgcat cgtcgtaggt ccattcaccg tcaacaccgt tgtcgttagc    60
gtactgtttg aa                                                       72

<210> SEQ ID NO 38
<211> LENGTH: 16
<212> TYPE: DNA
<213> ORGANISM: Artificial
<220> FEATURE:
<223> OTHER INFORMATION: Oligonucleotide to act as a primer for PCR

<400> SEQUENCE: 38
atgcgtccgg cgtaga                                                   16

<210> SEQ ID NO 39
<211> LENGTH: 35
<212> TYPE: DNA
<213> ORGANISM: Artificial
<220> FEATURE:
<223> OTHER INFORMATION: Oligonucleotide to act as a primer for PCR

<400> SEQUENCE: 39
tagcagttgg aattcgcggt caccgccggg gttaa                              35

<210> SEQ ID NO 40
<211> LENGTH: 35
<212> TYPE: DNA
<213> ORGANISM: Artificial
<220> FEATURE:
<223> OTHER INFORMATION: Oligonucleotide to act as a primer for PCR

<400> SEQUENCE: 40
aggagataga attctaccta caaattaatc ctgaa                              35

<210> SEQ ID NO 41
<211> LENGTH: 78
<212> TYPE: DNA
<213> ORGANISM: Artificial
<220> FEATURE:
<223> OTHER INFORMATION: Oligonucleotide to act as a primer for PCR

<400> SEQUENCE: 41
aacctgatct ttgcgaacgg cagcacccag accgcggaat ttaaaggcac ctttgaaaaa    60
agcatgactg gtggacag                                                 78

<210> SEQ ID NO 42
<211> LENGTH: 78
<212> TYPE: DNA
<213> ORGANISM: Artificial
<220> FEATURE:
<223> OTHER INFORMATION: Oligonucleotide to act as a primer for PCR

<400> SEQUENCE: 42
cgctttgatg gtcacttctt cttcgctatc ggtttccggg gtttccgggg tttcttcttt    60
catggtatat ctccttct                                                 78

<210> SEQ ID NO 43
<211> LENGTH: 73
<212> TYPE: DNA
<213> ORGANISM: Artificial
```

```
-continued

<220> FEATURE:
<223> OTHER INFORMATION: Oligonucleotide to act as a primer for PCR

<400> SEQUENCE: 43
tgaatatacc gtggatgtgg cggataaagg ttatacccctg aacattaaat ttgcgggttt        60
tttgctgaaa gga                                                            73

<210> SEQ ID NO 44
<211> LENGTH: 70
<212> TYPE: DNA
<213> ORGANISM: Artificial
<220> FEATURE:
<223> OTHER INFORMATION: Oligonucleotide to act as a primer for PCR

<400> SEQUENCE: 44
ccgttatctt ttttcagggt atccgcatac gcatacgctt cgctggtcgc ttttttcaaag        60 gtacctttaa                                                                70

<210> SEQ ID NO 45
<211> LENGTH: 16
<212> TYPE: DNA
<213> ORGANISM: Artificial
<220> FEATURE:
<223> OTHER INFORMATION: Oligonucleotide to act as a primer for PCR

<400> SEQUENCE: 45
atgcgtccgg cgtaga                                                         16

<210> SEQ ID NO 46
<211> LENGTH: 34
<212> TYPE: DNA
<213> ORGANISM: Artificial
<220> FEATURE:
<223> OTHER INFORMATION: Oligonucleotide to act as a primer for PCR

<400> SEQUENCE: 46 tccctgtcg aattcgcacc cgcaaattta atgt                                      34

<210> SEQ ID NO 47
<211> LENGTH: 35
<212> TYPE: DNA
<213> ORGANISM: Artificial
<220> FEATURE:
<223> OTHER INFORMATION: Oligonucleotide to act as a primer for PCR

<400> SEQUENCE: 47
aggagataga attctaaaga agaaaccccg gaaac                                    35

<210> SEQ ID NO 48
<211> LENGTH: 210
<212> TYPE: DNA
<213> ORGANISM: Artificial
<220> FEATURE:
<223> OTHER INFORMATION: Antigen binding amino acid sequence derived
      from C1 domain of Protein G (Streptococcus G148)
<220> FEATURE:
<221> NAME/KEY: CDS
<222> LOCATION: (1)..(210)
<223> OTHER INFORMATION:

<400> SEQUENCE: 48 acc tac aaa tta atc ctg aat ggt aaa acc ttg aaa ggc gaa acc act            48
Thr Tyr Lys Leu Ile Leu Asn Gly Lys Thr Leu Lys Gly Glu Thr Thr
1               5                   10                  15 act gaa gcg gtt gat gct gct acc gca gaa aaa gtt ttc aaa cag tac            96
Thr Glu Ala Val Asp Ala Ala Thr Ala Glu Lys Val Phe Lys Gln Tyr
```

```
                    20                  25                  30
gct aac gac aac ggt gtt gac ggt gaa tgg acc tac gac gat gcg act    144
Ala Asn Asp Asn Gly Val Asp Gly Glu Trp Thr Tyr Asp Asp Ala Thr
         35                  40                  45 aaa acc ttt acc gtt act gaa aaa ccg gaa gtg atc gat gcg tct gaa    192
Lys Thr Phe Thr Val Thr Glu Lys Pro Glu Val Ile Asp Ala Ser Glu
 50                  55                  60 tta acc ccg gcg gtg acc                                            210
Leu Thr Pro Ala Val Thr
 65                  70
```

<210> SEQ ID NO 49
<211> LENGTH: 70
<212> TYPE: PRT
<213> ORGANISM: Artificial
<220> FEATURE:
<223> OTHER INFORMATION: Antigen binding amino acid sequence derived
      from C1 domain of Protein G (Streptococcus G148)

<400> SEQUENCE: 49

```
Thr Tyr Lys Leu Ile Leu Asn Gly Lys Thr Leu Lys Gly Glu Thr Thr
 1               5                  10                  15

Thr Glu Ala Val Asp Ala Ala Thr Ala Glu Lys Val Phe Lys Gln Tyr
             20                  25                  30

Ala Asn Asp Asn Gly Val Asp Gly Glu Trp Thr Tyr Asp Asp Ala Thr
         35                  40                  45

Lys Thr Phe Thr Val Thr Glu Lys Pro Glu Val Ile Asp Ala Ser Glu
 50                  55                  60

Leu Thr Pro Ala Val Thr
 65                  70
```

<210> SEQ ID NO 50
<211> LENGTH: 228
<212> TYPE: DNA
<213> ORGANISM: Artificial
<220> FEATURE:
<223> OTHER INFORMATION: Antigen binding amino acid sequence derived
      from B1 domain of Protein L (Peptostreptococcus magnus)
<220> FEATURE:
<221> NAME/KEY: CDS
<222> LOCATION: (1)..(228)
<223> OTHER INFORMATION:

<400> SEQUENCE: 50

```
aaa gaa gaa acc ccg gaa acc ccg gaa acc gat agc gaa gaa gaa gtg    48
Lys Glu Glu Thr Pro Glu Thr Pro Glu Thr Asp Ser Glu Glu Glu Val
 1               5                  10                  15 acc atc aaa gcg aac ctg atc ttt gcg aac ggc agc acc cag acc gcg    96
Thr Ile Lys Ala Asn Leu Ile Phe Ala Asn Gly Ser Thr Gln Thr Ala
             20                  25                  30 gaa ttt aaa ggt acc ttt gaa aaa gcg acc agc gaa gcg tat gcg tat    144
Glu Phe Lys Gly Thr Phe Glu Lys Ala Thr Ser Glu Ala Tyr Ala Tyr
         35                  40                  45 gcg gat acc ctg aaa aaa gat aac ggt gaa tat acc gtg gat gtg gcg    192
Ala Asp Thr Leu Lys Lys Asp Asn Gly Glu Tyr Thr Val Asp Val Ala
 50                  55                  60 gat aaa ggt tat acc ctg aac att aaa ttt gcg ggt                    228
Asp Lys Gly Tyr Thr Leu Asn Ile Lys Phe Ala Gly
 65                  70                  75
```

<210> SEQ ID NO 51
<211> LENGTH: 76
<212> TYPE: PRT
<213> ORGANISM: Artificial

<220> FEATURE:
<223> OTHER INFORMATION: Antigen binding amino acid sequence derived
      from B1 domain of Protein L (Peptostreptococcus magnus)

<400> SEQUENCE: 51

Lys Glu Glu Thr Pro Glu Thr Pro Glu Thr Asp Ser Glu Glu Val
1               5                   10                  15

Thr Ile Lys Ala Asn Leu Ile Phe Ala Asn Gly Ser Thr Gln Thr Ala
            20                  25                  30

Glu Phe Lys Gly Thr Phe Glu Lys Ala Thr Ser Glu Ala Tyr Ala Tyr
        35                  40                  45

Ala Asp Thr Leu Lys Lys Asp Asn Gly Glu Tyr Thr Val Asp Val Ala
50                  55                  60

Asp Lys Gly Tyr Thr Leu Asn Ile Lys Phe Ala Gly
65                  70                  75

<210> SEQ ID NO 52
<211> LENGTH: 1446
<212> TYPE: DNA
<213> ORGANISM: Artificial
<220> FEATURE:
<223> OTHER INFORMATION: Fusion protein includes antibody binding amino
      acid sequence and Sendai virus nucleocapsid protein (G-NPK1)
<220> FEATURE:
<221> NAME/KEY: CDS
<222> LOCATION: (1)..(1446)
<223> OTHER INFORMATION:

<400> SEQUENCE: 52 atg acc tac aaa tta atc ctg aat ggt aaa acc ttg aaa ggc gaa acc    48
Met Thr Tyr Lys Leu Ile Leu Asn Gly Lys Thr Leu Lys Gly Glu Thr
1               5                   10                  15 act act gaa gcg gtt gat gct gct acc gca gaa aaa gtt ttc aaa cag    96
Thr Thr Glu Ala Val Asp Ala Ala Thr Ala Glu Lys Val Phe Lys Gln
            20                  25                  30 tac gct aac gac aac ggt gtt gac ggt gaa tgg acc tac gac gat gcg   144
Tyr Ala Asn Asp Asn Gly Val Asp Gly Glu Trp Thr Tyr Asp Asp Ala
        35                  40                  45 act aaa acc ttt acc gtt act gaa aaa ccg gaa gtg atc gat gcg tct   192
Thr Lys Thr Phe Thr Val Thr Glu Lys Pro Glu Val Ile Asp Ala Ser
50                  55                  60 gaa tta acc ccg gcg gtg acc gcg aat tcg agc tcg gta ccc ggg gat   240
Glu Leu Thr Pro Ala Val Thr Ala Asn Ser Ser Ser Val Pro Gly Asp
65                  70                  75                  80 ccg atg gcc ggg ttg ttg agc acc ttc gat aca ttt agc tct agg agg   288
Pro Met Ala Gly Leu Leu Ser Thr Phe Asp Thr Phe Ser Ser Arg Arg
            85                  90                  95 agc gaa agt att aat aag tcg gga gga ggt gct gtt atc ccc ggc cag   336
Ser Glu Ser Ile Asn Lys Ser Gly Gly Gly Ala Val Ile Pro Gly Gln
        100                 105                 110 agg agc aca gtc tca gtg ttc gta cta ggc cca agt gtg act gat gat   384
Arg Ser Thr Val Ser Val Phe Val Leu Gly Pro Ser Val Thr Asp Asp
        115                 120                 125 gca gac aag tta ttc att gca act acc ttc cta gct cac tca ttg gac   432
Ala Asp Lys Leu Phe Ile Ala Thr Thr Phe Leu Ala His Ser Leu Asp
130                 135                 140 aca gat aag cag cac tct cag aga gga ggg ttc ctc gtc tct ctg ctt   480
Thr Asp Lys Gln His Ser Gln Arg Gly Gly Phe Leu Val Ser Leu Leu
145                 150                 155                 160 gcc atg gct tac agt agt cca gaa ttg tac ttg aca aca aac gga gta   528
Ala Met Ala Tyr Ser Ser Pro Glu Leu Tyr Leu Thr Thr Asn Gly Val
            165                 170                 175

| | | |
|---|---|---|
| aac gcc gat gtc aaa tat gtg atc tac aac ata gag aaa gac cct aag<br>Asn Ala Asp Val Lys Tyr Val Ile Tyr Asn Ile Glu Lys Asp Pro Lys<br>180 185 190 | | 576 |
| agg acg aag aca gac gga ttc att gtg aag acg aga gat atg gaa tat<br>Arg Thr Lys Thr Asp Gly Phe Ile Val Lys Thr Arg Asp Met Glu Tyr<br>195 200 205 | | 624 |
| gag agg acc aca gaa tgg ctg ttt gga cct atg gtc aac aag agc cca<br>Glu Arg Thr Thr Glu Trp Leu Phe Gly Pro Met Val Asn Lys Ser Pro<br>210 215 220 | | 672 |
| ctc ttc cag ggt caa cgg gat gct gca gac cct gac aca ctc ctt caa<br>Leu Phe Gln Gly Gln Arg Asp Ala Ala Asp Pro Asp Thr Leu Leu Gln<br>225 230 235 240 | | 720 |
| atc tat ggg tat cct gca tgc cta gga gca ata att gtc caa gtc tgg<br>Ile Tyr Gly Tyr Pro Ala Cys Leu Gly Ala Ile Ile Val Gln Val Trp<br>245 250 255 | | 768 |
| att gtg ctg gtg aag gcc atc aca agc agc gcc ggc tta agg aaa ggg<br>Ile Val Leu Val Lys Ala Ile Thr Ser Ser Ala Gly Leu Arg Lys Gly<br>260 265 270 | | 816 |
| ttc ttc aac agg tta gag gcg ttc aga caa gac ggc acc gtg aaa ggt<br>Phe Phe Asn Arg Leu Glu Ala Phe Arg Gln Asp Gly Thr Val Lys Gly<br>275 280 285 | | 864 |
| gcc tta gtt ttc act ggg gag aca gtt gag ggg ata ggc tcg gtt atg<br>Ala Leu Val Phe Thr Gly Glu Thr Val Glu Gly Ile Gly Ser Val Met<br>290 295 300 | | 912 |
| aga tct cag caa agc ctt gta tct ctc atg gtt gag acc ctt gtg act<br>Arg Ser Gln Gln Ser Leu Val Ser Leu Met Val Glu Thr Leu Val Thr<br>305 310 315 320 | | 960 |
| atg aat act gca aga tct gat ctc acc aca tta gag aag aac atc cag<br>Met Asn Thr Ala Arg Ser Asp Leu Thr Thr Leu Glu Lys Asn Ile Gln<br>325 330 335 | | 1008 |
| atc gtt ggg aac tac atc cga gat gca ggg ctg gct tcc ttc atg aac<br>Ile Val Gly Asn Tyr Ile Arg Asp Ala Gly Leu Ala Ser Phe Met Asn<br>340 345 350 | | 1056 |
| act att aaa tat ggg gtg gag aca aag atg gca gct cta acg ttg tca<br>Thr Ile Lys Tyr Gly Val Glu Thr Lys Met Ala Ala Leu Thr Leu Ser<br>355 360 365 | | 1104 |
| aac ctg agg ccc gat att aat aag ctt aga agc ctc ata gac acc tac<br>Asn Leu Arg Pro Asp Ile Asn Lys Leu Arg Ser Leu Ile Asp Thr Tyr<br>370 375 380 | | 1152 |
| ctg tca aaa ggc ccc aga gct ccc ttt atc tgt atc ctc aag gac cct<br>Leu Ser Lys Gly Pro Arg Ala Pro Phe Ile Cys Ile Leu Lys Asp Pro<br>385 390 395 400 | | 1200 |
| gtt cat ggt gaa ttt gct cca ggc aat tat cct gca cta tgg agt tac<br>Val His Gly Glu Phe Ala Pro Gly Asn Tyr Pro Ala Leu Trp Ser Tyr<br>405 410 415 | | 1248 |
| gcc atg gga gtc gcc gtc gta cag aac aag gca atg cag cag tac gtc<br>Ala Met Gly Val Ala Val Val Gln Asn Lys Ala Met Gln Gln Tyr Val<br>420 425 430 | | 1296 |
| aca ggg agg aca tac ctt gat atg gaa atg ttc tta cta gga caa gcc<br>Thr Gly Arg Thr Tyr Leu Asp Met Glu Met Phe Leu Leu Gly Gln Ala<br>435 440 445 | | 1344 |
| gtg gca aag gat gct gaa tcg aag atc agc agt gcc ttg gaa gat gag<br>Val Ala Lys Asp Ala Glu Ser Lys Ile Ser Ser Ala Leu Glu Asp Glu<br>450 455 460 | | 1392 |
| tta gga gtg acg gat aca gcc aag ggg agg ctc aga cat cat ctg gca<br>Leu Gly Val Thr Asp Thr Ala Lys Gly Arg Leu Arg His His Leu Ala<br>465 470 475 480 | | 1440 |
| aac tag<br>Asn | | 1446 |

```
<210> SEQ ID NO 53
<211> LENGTH: 481
<212> TYPE: PRT
<213> ORGANISM: Artificial
<220> FEATURE:
<223> OTHER INFORMATION: Fusion protein includes antibody binding amino
      acid sequence and Sendai virus nucleocapsid protein (G-NPK1)

<400> SEQUENCE: 53

Met Thr Tyr Lys Leu Ile Leu Asn G

```
                370                 375                 380
Leu Ser Lys Gly Pro Arg Ala Pro Phe Ile Cys Ile Leu Lys Asp Pro
385                 390                 395                 400

Val His Gly Glu Phe Ala Pro Gly Asn Tyr Pro Ala Leu Trp Ser Tyr
                405                 410                 415

Ala Met Gly Val Ala Val Val Gln Asn Lys Ala Met Gln Gln Tyr Val
                420                 425                 430

Thr Gly Arg Thr Tyr Leu Asp Met Glu Met Phe Leu Leu Gly Gln Ala
                435                 440                 445

Val Ala Lys Asp Ala Glu Ser Lys Ile Ser Ser Ala Leu Glu Asp Glu
450                 455                 460

Leu Gly Val Thr Asp Thr Ala Lys Gly Arg Leu Arg His His Leu Ala
465                 470                 475                 480

Asn

<210> SEQ ID NO 54
<211> LENGTH: 1665
<212> TYPE: DNA
<213> ORGANISM: Artificial
<220> FEATURE:
<223> OTHER INFORMATION: Fusion protein includes antibody binding amino
      acid sequence and Sendai virus nucleocapsid protein (GG-NPK1)
<220

-continued

| | | |
|---|---|---|
| gga gga ggt gct gtt atc ccc ggc cag agg agc aca gtc tca gtg ttc<br>Gly Gly Gly Ala Val Ile Pro Gly Gln Arg Ser Thr Val Ser Val Phe<br>180                        185                      190 | 576 |
| gta cta ggc cca agt gtg act gat gat gca gac aag tta ttc att gca<br>Val Leu Gly Pro Ser Val Thr Asp Asp Ala Asp Lys Leu Phe Ile Ala<br>195                        200                      205 | 624 |
| act acc ttc cta gct cac tca ttg gac aca gat aag cag cac tct cag<br>Thr Thr Phe Leu Ala His Ser Leu Asp Thr Asp Lys Gln His Ser Gln<br>210                        215                      220 | 672 |
| aga gga ggg ttc ctc gtc tct ctg ctt gcc atg gct tac agt agt cca<br>Arg Gly Gly Phe Leu Val Ser Leu Leu Ala Met Ala Tyr Ser Ser Pro<br>225                        230                      235                      240 | 720 |
| gaa ttg tac ttg aca aca aac gga gta aac gcc gat gtc aaa tat gtg<br>Glu Leu Tyr Leu Thr Thr Asn Gly Val Asn Ala Asp Val Lys Tyr Val<br>                      245                      250                      255 | 768 |
| atc tac aac ata gag aaa gac cct aag agg acg aag aca gac gga ttc<br>Ile Tyr Asn Ile Glu Lys Asp Pro Lys Arg Thr Lys Thr Asp Gly Phe<br>                260                      265                      270 | 816 |
| att gtg aag acg aga gat atg gaa tat gag agg acc aca gaa tgg ctg<br>Ile Val Lys Thr Arg Asp Met Glu Tyr Glu Arg Thr Thr Glu Trp Leu<br>                275                      280                      285 | 864 |
| ttt gga cct atg gtc aac aag agc cca ctc ttc cag ggt caa cgg gat<br>Phe Gly Pro Met Val Asn Lys Ser Pro Leu Phe Gln Gly Gln Arg Asp<br>290                        295                      300 | 912 |
| gct gca gac cct gac aca ctc ctt caa atc tat ggg tat cct gca tgc<br>Ala Ala Asp Pro Asp Thr Leu Leu Gln Ile Tyr Gly Tyr Pro Ala Cys<br>305                        310                      315                      320 | 960 |
| cta gga gca ata att gtc caa gtc tgg att gtg ctg gtg aag gcc atc<br>Leu Gly Ala Ile Ile Val Gln Val Trp Ile Val Leu Val Lys Ala Ile<br>                      325                      330                      335 | 1008 |
| aca agc agc gcc ggc tta agg aaa ggg ttc ttc aac agg tta gag gcg<br>Thr Ser Ser Ala Gly Leu Arg Lys Gly Phe Phe Asn Arg Leu Glu Ala<br>                      340                      345                      350 | 1056 |
| ttc aga caa gac ggc acc gtg aaa ggt gcc tta gtt ttc act ggg gag<br>Phe Arg Gln Asp Gly Thr Val Lys Gly Ala Leu Val Phe Thr Gly Glu<br>                355                      360                      365 | 1104 |
| aca gtt gag ggg ata ggc tcg gtt atg aga tct cag caa agc ctt gta<br>Thr Val Glu Gly Ile Gly Ser Val Met Arg Ser Gln Gln Ser Leu Val<br>370                        375                      380 | 1152 |
| tct ctc atg gtt gag acc ctt gtg act atg aat act gca aga tct gat<br>Ser Leu Met Val Glu Thr Leu Val Thr Met Asn Thr Ala Arg Ser Asp<br>385                        390                      395                      400 | 1200 |
| ctc acc aca tta gag aag aac atc cag atc gtt ggg aac tac atc cga<br>Leu Thr Thr Leu Glu Lys Asn Ile Gln Ile Val Gly Asn Tyr Ile Arg<br>                      405                      410                      415 | 1248 |
| gat gca ggg ctg gct tcc ttc atg aac act att aaa tat ggg gtg gag<br>Asp Ala Gly Leu Ala Ser Phe Met Asn Thr Ile Lys Tyr Gly Val Glu<br>                      420                      425                      430 | 1296 |
| aca aag atg gca gct cta acg ttg tca aac ctg agg ccc gat att aat<br>Thr Lys Met Ala Ala Leu Thr Leu Ser Asn Leu Arg Pro Asp Ile Asn<br>                435                      440                      445 | 1344 |
| aag ctt aga agc ctc ata gac acc tac ctg tca aaa ggc ccc aga gct<br>Lys Leu Arg Ser Leu Ile Asp Thr Tyr Leu Ser Lys Gly Pro Arg Ala<br>450                        455                      460 | 1392 |
| ccc ttt atc tgt atc ctc aag gac cct gtt cat ggt gaa ttt gct cca<br>Pro Phe Ile Cys Ile Leu Lys Asp Pro Val His Gly Glu Phe Ala Pro<br>465                        470                      475                      480 | 1440 |
| ggc aat tat cct gca cta tgg agt tac gcc atg gga gtc gcc gtc gta<br>Gly Asn Tyr Pro Ala Leu Trp Ser Tyr Ala Met Gly Val Ala Val Val<br>                      485                      490                      495 | 1488 |

-continued

```
cag aac aag gca atg cag cag tac gtc aca ggg agg aca tac ctt gat    1536
Gln Asn Lys Ala Met Gln Gln Tyr Val Thr Gly Arg Thr Tyr Leu Asp
            500                 505                 510 atg gaa atg ttc tta cta gga caa gcc gtg gca aag gat gct gaa tcg    1584
Met Glu Met Phe Leu Leu Gly Gln Ala Val Ala Lys Asp Ala Glu Ser
        515                 520                 525 aag atc agc agt gcc ttg gaa gat gag tta gga gtg acg gat aca gcc    1632
Lys Ile Ser Ser Ala Leu Glu Asp Glu Leu Gly Val Thr Asp Thr Ala
530                 535                 540 aag ggg agg ctc aga cat cat ctg gca aac tag                        1665
Lys Gly Arg Leu Arg His His Leu Ala Asn
545                 550
```

<210> SEQ ID NO 55
<211> LENGTH: 554
<212> TYPE: PRT
<213> ORGANISM: Artificial
<220> FEATURE:
<223> OTHER INFORMATION: Fusion protein includes antibody binding amino
      acid sequence and Sendai virus nucleocapsid protein (GG-NPK1)

<400> SEQUENCE: 55

```
Met Thr Tyr Lys Leu Ile Leu Asn Gly Lys Thr Leu Lys Gly Glu Thr
1               5                   10                  15

Thr Thr Glu Ala Val Asp Ala Ala Thr Ala Glu Lys Val Phe Lys Gln
            20                  25                  30

Tyr Ala Asn Asp Asn Gly Val Asp Gly Glu Trp Thr Tyr Asp Asp Ala
        35                  40                  45

Thr Lys Thr Phe Thr Val Thr Glu Lys Pro Glu Val Ile Asp Ala Ser
    50                  55                  60

Glu Leu Thr Pro Ala Val Thr Ala Asn Ser Thr Tyr Lys Leu Ile Leu
65                  70                  75                  80

Asn Gly Lys Thr Leu Lys Gly Glu Thr Thr Thr Glu Ala Val Asp Ala
                85                  90                  95

Ala Thr Ala Glu Lys Val Phe Lys Gln Tyr Ala Asn Asp Asn Gly Val
            100                 105                 110

Asp Gly Glu Trp Thr Tyr Asp Asp Ala Thr Lys Thr Phe Thr Val Thr
        115                 120                 125

Glu Lys Pro Glu Val Ile Asp Ala Ser Glu Leu Thr Pro Ala Val Thr
    130                 135                 140

Ala Asn Ser Ser Ser Val Pro Gly Asp Pro Met Ala Gly Leu Leu Ser
145                 150                 155                 160

Thr Phe Asp Thr Phe Ser Ser Arg Arg Ser Glu Ser Ile Asn Lys Ser
                165                 170                 175

Gly Gly Gly Ala Val Ile Pro Gly Gln Arg Ser Thr Val Ser Val Phe
            180                 185                 190

Val Leu Gly Pro Ser Val Thr Asp Asp Ala Asp Lys Leu Phe Ile Ala
        195                 200                 205

Thr Thr Phe Leu Ala His Ser Leu Asp Thr Asp Lys Gln His Ser Gln
    210                 215                 220

Arg Gly Gly Phe Leu Val Ser Leu Leu Ala Met Ala Tyr Ser Ser Pro
225                 230                 235                 240

Glu Leu Tyr Leu Thr Thr Asn Gly Val Asn Ala Asp Val Lys Tyr Val
                245                 250                 255

Ile Tyr Asn Ile Glu Lys Asp Pro Lys Arg Thr Lys Thr Asp Gly Phe
            260                 265                 270

Ile Val Lys Thr Arg Asp Met Glu Tyr Glu Arg Thr Thr Glu Trp Leu
```

```
                275                 280                 285
Phe Gly Pro Met Val Asn Lys Ser Pro Leu Phe Gln Gly Gln Arg Asp
290                 295                 300

Ala Ala Asp Pro Asp Thr Leu Leu Gln Ile Tyr Gly Tyr Pro Ala Cys
305                 310                 315                 320

Leu Gly Ala Ile Ile Val Gln Val Trp Ile Leu Val Lys Ala Ile
            325                 330                 335

Thr Ser Ser Ala Gly Leu Arg Lys Gly Phe Phe Asn Arg Leu Glu Ala
            340                 345                 350

Phe Arg Gln Asp Gly Thr Val Lys Gly Ala Leu Val Phe Thr Gly Glu
            355                 360                 365

Thr Val Glu Gly Ile Gly Ser Val Met Arg Ser Gln Gln Ser Leu Val
    370                 375                 380

Ser Leu Met Val Glu Thr Leu Val Thr Met Asn Thr Ala Arg Ser Asp
385                 390                 395                 400

Leu Thr Thr Leu Glu Lys Asn Ile Gln Ile Val Gly Asn Tyr Ile Arg
                405                 410                 415

Asp Ala Gly Leu Ala Ser Phe Met Asn Thr Ile Lys Tyr Gly Val Glu
            420                 425                 430

Thr Lys Met Ala Ala Leu Thr Leu Ser Asn Leu Arg Pro Asp Ile Asn
            435                 440                 445

Lys Leu Arg Ser Leu Ile Asp Thr Tyr Leu Ser Lys Gly Pro Arg Ala
450                 455                 460

Pro Phe Ile Cys Ile Leu Lys Asp Pro Val His Gly Glu Phe Ala Pro
465                 470                 475                 480

Gly Asn Tyr Pro Ala Leu Trp Ser Tyr Ala Met Gly Val Ala Val Val
                485                 490                 495

Gln Asn Lys Ala Met Gln Gln Tyr Val Thr Gly Arg Thr Tyr Leu Asp
            500                 505                 510

Met Glu Met Phe Leu Leu Gly Gln Ala Val Ala Lys Asp Ala Glu Ser
            515                 520                 525

Lys Ile Ser Ser Ala Leu Glu Asp Glu Leu Gly Val Thr Asp Thr Ala
530                 535                 540

Lys Gly Arg Leu Arg His His Leu Ala Asn
545                 550

<210> SEQ ID NO 56
<211> LENGTH: 1464
<212> TYPE: DNA
<213> ORGANISM: Artificial
<220> FEATURE:
<223> OTHER INFORMATION: Fusion protein includes antibody binding amino
      acid sequence and Sendai virus nucleocapsid protein (L-NPK1)
<220> FEATURE:
<221> NAME/KEY: CDS
<222> LOCATION: (1)..(1464)
<223> OTHER INFORMATION:

<400> SEQUENCE: 56 atg aaa gaa gaa acc ccg gaa acc ccg gaa acc gat agc gaa gaa gaa         48
Met Lys Glu Glu Thr Pro Glu Thr Pro Glu Thr Asp Ser Glu Glu Glu
1               5                   10                  15 gtg acc atc aaa gcg aac ctg atc ttt gcg aac ggc agc acc cag acc         96
Val Thr Ile Lys Ala Asn Leu Ile Phe Ala Asn Gly Ser Thr Gln Thr
                20                  25                  30 gcg gaa ttt aaa ggt acc ttt gaa aaa gcg acc agc gaa gcg tat gcg        144
Ala Glu Phe Lys Gly Thr Phe Glu Lys Ala Thr Ser Glu Ala Tyr Ala
            35                  40                  45
```

| | | | | | | | | | | | | | | | | |
|---|---|---|---|---|---|---|---|---|---|---|---|---|---|---|---|---|
| tat | gcg | gat | acc | ctg | aaa | aaa | gat | aac | ggt | gaa | tat | acc | gtg | gat | gtg | 192 |
| Tyr | Ala | Asp | Thr | Leu | Lys | Lys | Asp | Asn | Gly | Glu | Tyr | Thr | Val | Asp | Val | |
| | 50 | | | | 55 | | | | | 60 | | | | | | |

| | | | | | | | | | | | | | | | | |
|---|---|---|---|---|---|---|---|---|---|---|---|---|---|---|---|---|
| gcg | gat | aaa | ggt | tat | acc | ctg | aac | att | aaa | ttt | gcg | ggt | gcg | aat | tcg | 240 |
| Ala | Asp | Lys | Gly | Tyr | Thr | Leu | Asn | Ile | Lys | Phe | Ala | Gly | Ala | Asn | Ser | |
| 65 | | | | | 70 | | | | 75 | | | | | | 80 | |

| | | | | | | | | | | | | | | | | |
|---|---|---|---|---|---|---|---|---|---|---|---|---|---|---|---|---|
| agc | tcg | gta | ccc | ggg | gat | ccg | atg | gcc | ggg | ttg | ttg | agc | acc | ttc | gat | 288 |
| Ser | Ser | Val | Pro | Gly | Asp | Pro | Met | Ala | Gly | Leu | Leu | Ser | Thr | Phe | Asp | |
| | | | | 85 | | | | | 90 | | | | | 95 | | |

| | | | | | | | | | | | | | | | | |
|---|---|---|---|---|---|---|---|---|---|---|---|---|---|---|---|---|
| aca | ttt | agc | tct | agg | agg | agc | gaa | agt | att | aat | aag | tcg | gga | gga | ggt | 336 |
| Thr | Phe | Ser | Ser | Arg | Arg | Ser | Glu | Ser | Ile | Asn | Lys | Ser | Gly | Gly | Gly | |
| | | | | 100 | | | | | 105 | | | | | 110 | | |

| | | | | | | | | | | | | | | | | |
|---|---|---|---|---|---|---|---|---|---|---|---|---|---|---|---|---|
| gct | gtt | atc | ccc | ggc | cag | agg | agc | aca | gtc | tca | gtg | ttc | gta | cta | ggc | 384 |
| Ala | Val | Ile | Pro | Gly | Gln | Arg | Ser | Thr | Val | Ser | Val | Phe | Val | Leu | Gly | |
| | | 115 | | | | | 120 | | | | | 125 | | | | |

| | | | | | | | | | | | | | | | | |
|---|---|---|---|---|---|---|---|---|---|---|---|---|---|---|---|---|
| cca | agt | gtg | act | gat | gat | gca | gac | aag | tta | ttc | att | gca | act | acc | ttc | 432 |
| Pro | Ser | Val | Thr | Asp | Asp | Ala | Asp | Lys | Leu | Phe | Ile | Ala | Thr | Thr | Phe | |
| 130 | | | | | 135 | | | | | 140 | | | | | | |

| | | | | | | | | | | | | | | | | |
|---|---|---|---|---|---|---|---|---|---|---|---|---|---|---|---|---|
| cta | gct | cac | tca | ttg | gac | aca | gat | aag | cag | cac | tct | cag | aga | gga | ggg | 480 |
| Leu | Ala | His | Ser | Leu | Asp | Thr | Asp | Lys | Gln | His | Ser | Gln | Arg | Gly | Gly | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ttc | ctc | gtc | tct | ctg | ctt | gcc | atg | gct | tac | agt | agt | cca | gaa | ttg | tac | 528 |
| Phe | Leu | Val | Ser | Leu | Leu | Ala | Met | Ala | Tyr | Ser | Ser | Pro | Glu | Leu | Tyr | |
| | | | | 165 | | | | | 170 | | | | | 175 | | |

| | | | | | | | | | | | | | | | | |
|---|---|---|---|---|---|---|---|---|---|---|---|---|---|---|---|---|
| ttg | aca | aca | aac | gga | gta | aac | gcc | gat | gtc | aaa | tat | gtg | atc | tac | aac | 576 |
| Leu | Thr | Thr | Asn | Gly | Val | Asn | Ala | Asp | Val | Lys | Tyr | Val | Ile | Tyr | Asn | |
| | | | 180 | | | | | 185 | | | | | 190 | | | |

| | | | | | | | | | | | | | | | | |
|---|---|---|---|---|---|---|---|---|---|---|---|---|---|---|---|---|
| ata | gag | aaa | gac | cct | aag | agg | acg | aag | aca | gac | gga | ttc | att | gtg | aag | 624 |
| Ile | Glu | Lys | Asp | Pro | Lys | Arg | Thr | Lys | Thr | Asp | Gly | Phe | Ile | Val | Lys | |
| | | 195 | | | | | 200 | | | | | 205 | | | | |

| | | | | | | | | | | | | | | | | |
|---|---|---|---|---|---|---|---|---|---|---|---|---|---|---|---|---|
| acg | aga | gat | atg | gaa | tat | gag | agg | acc | aca | gaa | tgg | ctg | ttt | gga | cct | 672 |
| Thr | Arg | Asp | Met | Glu | Tyr | Glu | Arg | Thr | Thr | Glu | Trp | Leu | Phe | Gly | Pro | |
| 210 | | | | | 215 | | | | | 220 | | | | | | |

| | | | | | | | | | | | | | | | | |
|---|---|---|---|---|---|---|---|---|---|---|---|---|---|---|---|---|
| atg | gtc | aac | aag | agc | cca | ctc | ttc | cag | ggt | caa | cgg | gat | gct | gca | gac | 720 |
| Met | Val | Asn | Lys | Ser | Pro | Leu | Phe | Gln | Gly | Gln | Arg | Asp | Ala | Ala | Asp | |
| 225 | | | | 230 | | | | | 235 | | | | | 240 | | |

| | | | | | | | | | | | | | | | | |
|---|---|---|---|---|---|---|---|---|---|---|---|---|---|---|---|---|
| cct | gac | aca | ctc | ctt | caa | atc | tat | ggg | tat | cct | gca | tgc | cta | gga | gca | 768 |
| Pro | Asp | Thr | Leu | Leu | Gln | Ile | Tyr | Gly | Tyr | Pro | Ala | Cys | Leu | Gly | Ala | |
| | | | | 245 | | | | | 250 | | | | | 255 | | |

| | | | | | | | | | | | | | | | | |
|---|---|---|---|---|---|---|---|---|---|---|---|---|---|---|---|---|
| ata | att | gtc | caa | gtc | tgg | att | gtg | ctg | gtg | aag | gcc | atc | aca | agc | agc | 816 |
| Ile | Ile | Val | Gln | Val | Trp | Ile | Val | Leu | Val | Lys | Ala | Ile | Thr | Ser | Ser | |
| | | | 260 | | | | | 265 | | | | | 270 | | | |

| | | | | | | | | | | | | | | | | |
|---|---|---|---|---|---|---|---|---|---|---|---|---|---|---|---|---|
| gcc | ggc | tta | agg | aaa | ggg | ttc | ttc | aac | agg | tta | gag | gcg | ttc | aga | caa | 864 |
| Ala | Gly | Leu | Arg | Lys | Gly | Phe | Phe | Asn | Arg | Leu | Glu | Ala | Phe | Arg | Gln | |
| | | 275 | | | | | 280 | | | | | 285 | | | | |

| | | | | | | | | | | | | | | | | |
|---|---|---|---|---|---|---|---|---|---|---|---|---|---|---|---|---|
| gac | ggc | acc | gtg | aaa | ggt | gcc | tta | gtt | ttc | act | ggg | gag | aca | gtt | gag | 912 |
| Asp | Gly | Thr | Val | Lys | Gly | Ala | Leu | Val | Phe | Thr | Gly | Glu | Thr | Val | Glu | |
| | 290 | | | | | 295 | | | | | 300 | | | | | |

| | | | | | | | | | | | | | | | | |
|---|---|---|---|---|---|---|---|---|---|---|---|---|---|---|---|---|
| ggg | ata | ggc | tcg | gtt | atg | aga | tct | cag | caa | agc | ctt | gta | tct | ctc | atg | 960 |
| Gly | Ile | Gly | Ser | Val | Met | Arg | Ser | Gln | Gln | Ser | Leu | Val | Ser | Leu | Met | |
| 305 | | | | | 310 | | | | | 315 | | | | | 320 | |

| | | | | | | | | | | | | | | | | |
|---|---|---|---|---|---|---|---|---|---|---|---|---|---|---|---|---|
| gtt | gag | acc | ctt | gtg | act | atg | aat | act | gca | aga | tct | gat | ctc | acc | aca | 1008 |
| Val | Glu | Thr | Leu | Val | Thr | Met | Asn | Thr | Ala | Arg | Ser | Asp | Leu | Thr | Thr | |
| | | | | 325 | | | | | 330 | | | | | 335 | | |

| | | | | | | | | | | | | | | | | |
|---|---|---|---|---|---|---|---|---|---|---|---|---|---|---|---|---|
| tta | gag | aag | aac | atc | cag | atc | gtt | ggg | aac | tac | atc | cga | gat | gca | ggg | 1056 |
| Leu | Glu | Lys | Asn | Ile | Gln | Ile | Val | Gly | Asn | Tyr | Ile | Arg | Asp | Ala | Gly | |
| | | | 340 | | | | | 345 | | | | | 350 | | | |

| | | | | | | | | | | | | | | | | |
|---|---|---|---|---|---|---|---|---|---|---|---|---|---|---|---|---|
| ctg | gct | tcc | ttc | atg | aac | act | att | aaa | tat | ggg | gtg | gag | aca | aag | atg | 1104 |
| Leu | Ala | Ser | Phe | Met | Asn | Thr | Ile | Lys | Tyr | Gly | Val | Glu | Thr | Lys | Met | |
| | | 355 | | | | | 360 | | | | | 365 | | | | |

```
gca gct cta acg ttg tca aac ctg agg ccc gat att aat aag ctt aga       1152
Ala Ala Leu Thr Leu Ser Asn Leu Arg Pro Asp Ile Asn Lys Leu Arg
    370                 375                 380 agc ctc ata gac acc tac ctg tca aaa ggc ccc aga gct ccc ttt atc       1200
Ser Leu Ile Asp Thr Tyr Leu Ser Lys Gly Pro Arg Ala Pro Phe Ile
385                 390                 395                 400 tgt atc ctc aag gac cct gtt cat ggt gaa ttt gct cca ggc aat tat       1248
Cys Ile Leu Lys Asp Pro Val His Gly Glu Phe Ala Pro Gly Asn Tyr
                405                 410                 415 cct gca cta tgg agt tac gcc atg gga gtc gcc gtc gta cag aac aag       1296
Pro Ala Leu Trp Ser Tyr Ala Met Gly Val Ala Val Val Gln Asn Lys
            420                 425                 430 gca atg cag cag tac gtc aca ggg agg aca tac ctt gat atg gaa atg       1344
Ala Met Gln Gln Tyr Val Thr Gly Arg Thr Tyr Leu Asp Met Glu Met
        435                 440                 445 ttc tta cta gga caa gcc gtg gca aag gat gct gaa tcg aag atc agc       1392
Phe Leu Leu Gly Gln Ala Val Ala Lys Asp Ala Glu Ser Lys Ile Ser
    450                 455                 460 agt gcc ttg gaa gat gag tta gga gtg acg gat aca gcc aag ggg agg       1440
Ser Ala Leu Glu Asp Glu Leu Gly Val Thr Asp Thr Ala Lys Gly Arg
465                 470                 475                 480 ctc aga cat cat ctg gca aac tag                                       1464
Leu Arg His His Leu Ala Asn
                485

<210> SEQ ID NO 57
<211> LENGTH: 487
<212> TYPE: PRT
<213> ORGANISM: Artificial
<220> FEATURE:
<223> OTHER INFORMATION: Fusion protein includes antibody binding amino
      acid sequence and Sendai virus nucleocapsid protein (L-NPK1)

<400> SEQUENCE: 57

Met Lys Glu Glu Thr Pro Glu Thr Pro Glu Thr Asp Ser Glu Glu
1               5                   10                  15

Val Thr Ile Lys Ala Asn Leu Ile Phe Ala Asn Gly Ser Thr Gln Thr
            20                  25                  30

Ala Glu Phe Lys Gly Thr Phe Glu Lys Ala Thr Ser Glu Ala Tyr Ala
        35                  40                  45

Tyr Ala Asp Thr Leu Lys Lys Asp Asn Gly Glu Tyr Thr Val Asp Val
    50                  55                  60

Ala Asp Lys Gly Tyr Thr Leu Asn Ile Lys Phe Ala Gly Ala Asn Ser
65                  70                  75                  80

Ser Ser Val Pro Gly Asp Pro Met Ala Gly Leu Leu Ser Thr Phe Asp
                85                  90                  95

Thr Phe Ser Ser Arg Arg Ser Glu Ser Ile Asn Lys Ser Gly Gly Gly
                100                 105                 110

Ala Val Ile Pro Gly Gln Arg Ser Thr Val Ser Val Phe Val Leu Gly
            115                 120                 125

Pro Ser Val Thr Asp Asp Ala Asp Lys Leu Phe Ile Ala Thr Thr Phe
    130                 135                 140

Leu Ala His Ser Leu Asp Thr Asp Lys Gln His Ser Gln Arg Gly Gly
145                 150                 155                 160

Phe Leu Val Ser Leu Leu Ala Met Ala Tyr Ser Ser Pro Glu Leu Tyr
                165                 170                 175

Leu Thr Thr Asn Gly Val Asn Ala Asp Val Lys Tyr Val Ile Tyr Asn
                180                 185                 190

Ile Glu Lys Asp Pro Lys Arg Thr Lys Thr Asp Gly Phe Ile Val Lys
```

```
                195                 200                 205
Thr Arg Asp Met Glu Tyr Glu Arg Thr Thr Glu Trp Leu Phe Gly Pro
210                 215                 220

Met Val Asn Lys Ser Pro Leu Phe Gln Gly Gln Arg Asp Ala Ala Asp
225                 230                 235                 240

Pro Asp Thr Leu Leu Gln Ile Tyr Gly Tyr Pro Ala Cys Leu Gly Ala
                245                 250                 255

Ile Ile Val Gln Val Trp Ile Val Leu Val Lys Ala Ile Thr Ser Ser
                260                 265                 270

Ala Gly Leu Arg Lys Gly Phe Phe Asn Arg Leu Glu Ala Phe Arg Gln
                275                 280                 285

Asp Gly Thr Val Lys Gly Ala Leu Val Phe Thr Gly Glu Thr Val Glu
                290                 295                 300

Gly Ile Gly Ser Val Met Arg Ser Gln Gln Ser Leu Val Ser Leu Met
305                 310                 315                 320

Val Glu Thr Leu Val Thr Met Asn Thr Ala Arg Ser Asp Leu Thr Thr
                325                 330                 335

Leu Glu Lys Asn Ile Gln Ile Val Gly Asn Tyr Ile Arg Asp Ala Gly
                340                 345                 350

Leu Ala Ser Phe Met Asn Thr Ile Lys Tyr Gly Val Glu Thr Lys Met
                355                 360                 365

Ala Ala Leu Thr Leu Ser Asn Leu Arg Pro Asp Ile Asn Lys Leu Arg
370                 375                 380

Ser Leu Ile Asp Thr Tyr Leu Ser Lys Gly Pro Arg Ala Pro Phe Ile
385                 390                 395                 400

Cys Ile Leu Lys Asp Pro Val His Gly Glu Phe Ala Pro Gly Asn Tyr
                405                 410                 415

Pro Ala Leu Trp Ser Tyr Ala Met Gly Val Ala Val Gln Asn Lys
                420                 425                 430

Ala Met Gln Gln Tyr Val Thr Gly Arg Thr Tyr Leu Asp Met Glu Met
                435                 440                 445

Phe Leu Leu Gly Gln Ala Val Ala Lys Asp Ala Glu Ser Lys Ile Ser
450                 455                 460

Ser Ala Leu Glu Asp Glu Leu Gly Val Thr Asp Thr Ala Lys Gly Arg
465                 470                 475                 480

Leu Arg His His Leu Ala Asn
                485

<210> SEQ ID NO 58
<211> LENGTH: 1701
<212> TYPE: DNA
<213> ORGANISM: Artificial
<220> FEATURE:
<223> OTHER INFORMATION: Fusion protein includes antibody binding amino
      acid sequence and Sendai virus nucleocapsid protein (LL -continued

| | | | | | | | | | | | | | | |
|---|---|---|---|---|---|---|---|---|---|---|---|---|---|---|
| Ala | Glu | Phe | Lys | Gly | Thr | Phe | Glu | Lys | Ala | Thr | Ser | Glu | Ala | Tyr | Ala |
| | | 35 | | | | 40 | | | | 45 | | | | |

```
tat gcg gat acc ctg aaa aaa gat aac ggt gaa tat acc gtg gat gtg      192
Tyr Ala Asp Thr Leu Lys Lys Asp Asn Gly Glu Tyr Thr Val Asp Val
    50              55                  60 gcg gat aaa ggt tat acc ctg aac att aaa ttt gcg ggt gcg aat tct      240
Ala Asp Lys Gly Tyr Thr Leu Asn Ile Lys Phe Ala Gly Ala Asn Ser
65              70                  75                  80 aaa gaa gaa acc ccg gaa acc ccg gaa acc gat agc gaa gaa gaa gtg      288
Lys Glu Glu Thr Pro Glu Thr Pro Glu Thr Asp Ser Glu Glu Glu Val
                85                  90                  95 acc atc aaa gcg aac ctg atc ttt gcg aac ggc agc acc cag acc gcg      336
Thr Ile Lys Ala Asn Leu Ile Phe Ala Asn Gly Ser Thr Gln Thr Ala
            100                 105                 110 gaa ttt aaa ggt acc ttt gaa aaa gcg acc agc gaa gcg tat gcg tat      384
Glu Phe Lys Gly Thr Phe Glu Lys Ala Thr Ser Glu Ala Tyr Ala Tyr
        115                 120                 125 gcg gat acc ctg aaa aaa gat aac ggt gaa tat acc gtg gat gtg gcg      432
Ala Asp Thr Leu Lys Lys Asp Asn Gly Glu Tyr Thr Val Asp Val Ala
130                 135                 140 gat aaa ggt tat acc ctg aac att aaa ttt gcg ggt gcg aat tcg agc      480
Asp Lys Gly Tyr Thr Leu Asn Ile Lys Phe Ala Gly Ala Asn Ser Ser
145                 150                 155                 160 tcg gta ccc ggg gat ccg atg gcc ggg ttg ttg agc acc ttc gat aca      528
Ser Val Pro Gly Asp Pro Met Ala Gly Leu Leu Ser Thr Phe Asp Thr
                165                 170                 175 ttt agc tct agg agg agc gaa agt att aat aag tcg gga gga ggt gct      576
Phe Ser Ser Arg Arg Ser Glu Ser Ile Asn Lys Ser Gly Gly Gly Ala
            180                 185                 190 gtt atc ccc ggc cag agg agc aca gtc tca gtg ttc gta cta ggc cca      624
Val Ile Pro Gly Gln Arg Ser Thr Val Ser Val Phe Val Leu Gly Pro
        195                 200                 205 agt gtg act gat gat gca gac aag tta ttc att gca act acc ttc cta      672
Ser Val Thr Asp Asp Ala Asp Lys Leu Phe Ile Ala Thr Thr Phe Leu
210                 215                 220 gct cac tca ttg gac aca gat aag cag cac tct cag aga gga ggg ttc      720
Ala His Ser Leu Asp Thr Asp Lys Gln His Ser Gln Arg Gly Gly Phe
225                 230                 235                 240 ctc gtc tct ctg ctt gcc atg gct tac agt agt cca gaa ttg tac ttg      768
Leu Val Ser Leu Leu Ala Met Ala Tyr Ser Ser Pro Glu Leu Tyr Leu
                245                 250                 255 aca aca aac gga gta aac gcc gat gtc aaa tat gtg atc tac aac ata      816
Thr Thr Asn Gly Val Asn Ala Asp Val Lys Tyr Val Ile Tyr Asn Ile
            260                 265                 270 gag aaa gac cct aag agg acg aag aca gac gga ttc att gtg aag acg      864
Glu Lys Asp Pro Lys Arg Thr Lys Thr Asp Gly Phe Ile Val Lys Thr
        275                 280                 285 aga gat atg gaa tat gag agg acc aca gaa tgg ctg ttt gga cct atg      912
Arg Asp Met Glu Tyr Glu Arg Thr Thr Glu Trp Leu Phe Gly Pro Met
290                 295                 300 gtc aac aag agc cca ctc ttc cag ggt caa cgg gat gct gca gac cct      960
Val Asn Lys Ser Pro Leu Phe Gln Gly Gln Arg Asp Ala Ala Asp Pro
305                 310                 315                 320 gac aca ctc ctt caa atc tat ggg tat cct gca tgc cta gga gca ata     1008
Asp Thr Leu Leu Gln Ile Tyr Gly Tyr Pro Ala Cys Leu Gly Ala Ile
                325                 330                 335 att gtc caa gtc tgg att gtg ctg gtg aag gcc atc aca agc agc gcc     1056
Ile Val Gln Val Trp Ile Val Leu Val Lys Ala Ile Thr Ser Ser Ala
            340                 345                 350 ggc tta agg aaa ggg ttc ttc aac agg tta gag gcg ttc aga caa gac     1104
```

```
           Gly Leu Arg Lys Gly Phe Phe Asn Arg Leu Glu Ala Phe Arg Gln Asp
                       355                 360                 365 ggc acc gtg aaa ggt gcc tta gtt ttc act ggg gag aca gtt gag ggg          1152
Gly Thr Val Lys Gly Ala Leu Val Phe Thr Gly Glu Thr Val Glu Gly
        370                 375                 380 ata ggc tcg gtt atg aga tct cag caa agc ctt gta tct ctc atg gtt         1200
Ile Gly Ser Val Met Arg Ser Gln Gln Ser Leu Val Ser Leu Met Val
385                 390                 395                 400 gag acc ctt gtg act atg aat act gca aga tct gat ctc acc aca tta         1248
Glu Thr Leu Val Thr Met Asn Thr Ala Arg Ser Asp Leu Thr Thr Leu
            405                 410                 415 gag aag aac atc cag atc gtt ggg aac tac atc cga gat gca ggg ctg         1296
Glu Lys Asn Ile Gln Ile Val Gly Asn Tyr Ile Arg Asp Ala Gly Leu
        420                 425                 430 gct tcc ttc atg aac act att aaa tat ggg gtg gag aca aag atg gca         1344
Ala Ser Phe Met Asn Thr Ile Lys Tyr Gly Val Glu Thr Lys Met Ala
                435                 440                 445 gct cta acg ttg tca aac ctg agg ccc gat att aat aag ctt aga agc         1392
Ala Leu Thr Leu Ser Asn Leu Arg Pro Asp Ile Asn Lys Leu Arg Ser
450                 455                 460 ctc ata gac acc tac ctg tca aaa ggc ccc aga gct ccc ttt atc tgt         1440
Leu Ile Asp Thr Tyr Leu Ser Lys Gly Pro Arg Ala Pro Phe Ile Cys
465                 470                 475                 480 atc ctc aag gac cct gtt cat ggt gaa ttt gct cca ggc aat tat cct         1488
Ile Leu Lys Asp Pro Val His Gly Glu Phe Ala Pro Gly Asn Tyr Pro
            485                 490                 495 gca cta tgg agt tac gcc atg gga gtc gcc gtc gta cag aac aag gca         1536
Ala Leu Trp Ser Tyr Ala Met Gly Val Ala Val Val Gln Asn Lys Ala
        500                 505                 510 atg cag cag tac gtc aca ggg agg aca tac ctt gat atg gaa atg ttc         1584
Met Gln Gln Tyr Val Thr Gly Arg Thr Tyr Leu Asp Met Glu Met Phe
                515                 520                 525 tta cta gga caa gcc gtg gca aag gat gct gaa tcg aag atc agc agt         1632
Leu Leu Gly Gln Ala Val Ala Lys Asp Ala Glu Ser Lys Ile Ser Ser
530                 535                 540 gcc ttg gaa gat gag tta gga gtg acg gat aca gcc aag ggg agg ctc         1680
Ala Leu Glu Asp Glu Leu Gly Val Thr Asp Thr Ala Lys Gly Arg Leu
545                 550                 555                 560 aga cat cat ctg gca aac tag                                              1701
Arg His His Leu Ala Asn
            565

<210> SEQ ID NO 59
<211> LENGTH: 566
<212> TYPE: PRT
<213> ORGANISM: Artificial
<220> FEATURE:
<223> OTHER INFORMATION: Fusion protein includes antibody binding amino
      acid sequence and Sendai virus nucleocapsid protein (LL-NPK1)

<400> SEQUENCE: 59

Met Lys Glu Glu Thr Pro Glu Thr Pro Glu Thr Asp

```
Lys Glu Glu Thr Pro Glu Thr Pro Thr Asp Ser Glu Glu Val
                85              90              95

Thr Ile Lys Ala Asn Leu Ile Phe Ala Asn Gly Ser Thr Gln Thr Ala
            100             105             110

Glu Phe Lys Gly Thr Phe Glu Lys Ala Thr Ser Glu Ala Tyr Ala Tyr
            115             120             125

Ala Asp Thr Leu Lys Lys Asp Asn Gly Glu Tyr Thr Val Asp Val Ala
130             135             140

Asp Lys Gly Tyr Thr Leu Asn Ile Lys Phe Ala Gly Ala Asn Ser Ser
145             150             155             160

Ser Val Pro Gly Asp Pro Met Ala Gly Leu Leu Ser Thr Phe Asp Thr
                165             170             175

Phe Ser Ser Arg Arg Ser Glu Ser Ile Asn Lys Ser Gly Gly Gly Ala
                180             185             190

Val Ile Pro Gly Gln Arg Ser Thr Val Ser Val Phe Val Leu Gly Pro
            195             200             205

Ser Val Thr Asp Asp Ala Asp Lys Leu Phe Ile Ala Thr Thr Phe Leu
        210             215             220

Ala His Ser Leu Asp Thr Asp Lys Gln His Ser Gln Arg Gly Gly Phe
225             230             235             240

Leu Val Ser Leu Leu Ala Met Ala Tyr Ser Ser Pro Glu Leu Tyr Leu
                245             250             255

Thr Thr Asn Gly Val Asn Ala Asp Val Lys Tyr Val Ile Tyr Asn Ile
                260             265             270

Glu Lys Asp Pro Lys Arg Thr Lys Thr Asp Gly Phe Ile Val Lys Thr
            275             280             285

Arg Asp Met Glu Tyr Glu Arg Thr Thr Glu Trp Leu Phe Gly Pro Met
        290             295             300

Val Asn Lys Ser Pro Leu Phe Gln Gly Gln Arg Asp Ala Ala Asp Pro
305             310             315             320

Asp Thr Leu Leu Gln Ile Tyr Gly Tyr Pro Ala Cys Leu Gly Ala Ile
                325             330             335

Ile Val Gln Val Trp Ile Val Leu Val Lys Ala Ile Thr Ser Ser Ala
                340             345             350

Gly Leu Arg Lys Gly Phe Phe Asn Arg Leu Glu Ala Phe Arg Gln Asp
            355             360             365

Gly Thr Val Lys Gly Ala Leu Val Phe Thr Gly Glu Thr Val Glu Gly
        370             375             380

Ile Gly Ser Val Met Arg Ser Gln Gln Ser Leu Val Ser Leu Met Val
385             390             395             400

Glu Thr Leu Val Thr Met Asn Thr Ala Arg Ser Asp Leu Thr Thr Leu
                405             410             415

Glu Lys Asn Ile Gln Ile Val Gly Asn Tyr Ile Arg Asp Ala Gly Leu
            420             425             430

Ala Ser Phe Met Asn Thr Ile Lys Tyr Gly Val Glu Thr Lys Met Ala
            435             440             445

Ala Leu Thr Leu Ser Asn Leu Arg Pro Asp Ile Asn Lys Leu Arg Ser
        450             455             460

Leu Ile Asp Thr Tyr Leu Ser Lys Gly Pro Arg Ala Pro Phe Ile Cys
465             470             475             480

Ile Leu Lys Asp Pro Val His Gly Glu Phe Ala Pro Gly Asn Tyr Pro
                485             490             495

Ala Leu Trp Ser Tyr Ala Met Gly Val Ala Val Val Gln Asn Lys Ala
```

-continued

```
                500                 505                 510
Met Gln Gln Tyr Val Thr Gly Arg Thr Tyr Leu Asp Met Glu Met Phe
            515                 520                 525

Leu Leu Gly Gln Ala Val Ala Lys Asp Ala Glu Ser Lys Ile Ser Ser
            530                 535                 540

Ala Leu Glu Asp Glu Leu Gly Val Thr Asp Thr Ala Lys Gly Arg Leu
545                 550                 555                 560

Arg His His Leu Ala Asn
                565
```